(12) United States Patent
Nitzan et al.

(10) Patent No.: US 12,179,010 B2
(45) Date of Patent: *Dec. 31, 2024

(54) SYSTEMS AND METHODS FOR REDUCING PRESSURE AT AN OUTFLOW OF A DUCT

(71) Applicant: White Swell Medical Ltd, Kibbutz Shefayim (IL)

(72) Inventors: Yaacov Nitzan, Hertzelia (IL); Menashe Yacoby, Ramat Gan (IL); Sagi Raz, Tel-Aviv (IL); Shani Chen, Givatayim (IL); Or Inbar, Tel-Aviv (IL)

(73) Assignee: White Swell Medical Ltd, Kibbutz Shefayim (IL)

( * ) Notice: Subject to any disclaimer, the term of this patent is extended or adjusted under 35 U.S.C. 154(b) by 0 days.

This patent is subject to a terminal disclaimer.

(21) Appl. No.: 18/368,225

(22) Filed: Sep. 14, 2023

(65) Prior Publication Data

US 2024/0058595 A1 Feb. 22, 2024

Related U.S. Application Data

(63) Continuation of application No. 17/141,937, filed on Jan. 5, 2021, now Pat. No. 11,793,995, which is a
(Continued)

(51) Int. Cl.
*A61M 60/50* (2021.01)
*A61M 60/13* (2021.01)
(Continued)

(52) U.S. Cl.
CPC ........... *A61M 60/50* (2021.01); *A61M 60/13* (2021.01); *A61M 60/135* (2021.01);
(Continued)

(58) Field of Classification Search
CPC ................ A61M 60/13; A61M 60/135; A61M 60/237; A61M 60/414; A61M 60/833
See application file for complete search history.

(56) References Cited

U.S. PATENT DOCUMENTS 3,211,150 A 10/1965 Foderick
3,884,240 A 5/1975 Gilman
(Continued)

FOREIGN PATENT DOCUMENTS

CA 2250993 A1 10/1997
EP 0526102 A1 2/1993
(Continued)

OTHER PUBLICATIONS

Bannon, 2011, Anatomic considerations for central venous cannulation, Risk Manag Healthc Policy 4:27-39.
(Continued)

*Primary Examiner* — Jessica Arble
(74) *Attorney, Agent, or Firm* — Brown Rudnick LLP; Adam M. Schoen

(57) ABSTRACT

Various systems and methods are provided for reducing pressure at an outflow of a duct such as the thoracic duct or the lymphatic duct. A catheter system can include a catheter shaft configured to be at least partially implantable within a patient's vein, a flexible membrane attached to the catheter shaft, the flexible membrane being a collapsible, tube-like member having a lumen extending therethrough, and a single selectively deployable restriction member formed over a portion of the flexible membrane at substantially a midpoint between a proximal end of the flexible membrane and a distal end of the flexible membrane, the restriction member being configured to control a size of the lumen so
(Continued)

as to direct a controlled volume of fluid from an upstream side of the restriction member to a downstream side the restriction member.

18 Claims, 37 Drawing Sheets

Related U.S. Application Data continuation of application No. 15/909,290, filed on Mar. 1, 2018, now Pat. No. 10,912,873.

(60) Provisional application No. 62/466,191, filed on Mar. 2, 2017.

(51) Int. Cl.
| | |
|---|---|
| A61M 60/135 | (2021.01) |
| A61M 60/237 | (2021.01) |
| A61M 60/414 | (2021.01) |
| A61M 60/833 | (2021.01) |
| A61M 25/01 | (2006.01) |
| A61M 60/279 | (2021.01) |

(52) U.S. Cl.
CPC ........ *A61M 60/237* (2021.01); *A61M 60/414* (2021.01); *A61M 60/833* (2021.01); *A61M 25/0108* (2013.01); *A61M 60/279* (2021.01); *A61M 2205/3303* (2013.01); *A61M 2205/3306* (2013.01); *A61M 2205/3331* (2013.01); *A61M 2205/3379* (2013.01); *A61M 2230/06* (2013.01); *A61M 2230/30* (2013.01); *A61M 2230/42* (2013.01); *A61M 2230/63* (2013.01)

(56) References Cited

U.S. PATENT DOCUMENTS

| | | | |
|---|---|---|---|
| 3,926,175 | A | 12/1975 | Allen et al. |
| 4,714,460 | A | 12/1987 | Calderon |
| 4,822,341 | A | 4/1989 | Colone |
| 4,838,864 | A | 6/1989 | Peterson |
| 4,957,484 | A | 9/1990 | Murtfeldt |
| 5,005,564 | A | 4/1991 | Grundei et al. |
| 5,069,662 | A | 12/1991 | Bodden |
| 5,092,844 | A | 3/1992 | Schwartz et al. |
| 5,097,840 | A | 3/1992 | Wallace et al. |
| 5,366,504 | A | 11/1994 | Andersen et al. |
| 5,391,143 | A | 2/1995 | Kensey |
| 5,484,412 | A | 1/1996 | Pierpont |
| 5,509,897 | A | 4/1996 | Twardowski et al. |
| 5,554,119 | A | 9/1996 | Harrison et al. |
| 5,558,642 | A | 9/1996 | Schweich, Jr. et al. |
| 5,702,364 | A | 12/1997 | Euteneuer |
| 5,716,340 | A | 2/1998 | Schweich, Jr. et al. |
| 5,817,046 | A | 10/1998 | Glickman |
| 5,836,912 | A | 11/1998 | Kusleika |
| 5,893,841 | A | 4/1999 | Glickman |
| 5,897,533 | A | 4/1999 | Glickman |
| 5,908,407 | A | 6/1999 | Frazee et al. |
| 5,919,163 | A | 7/1999 | Glickman |
| 5,921,913 | A | 7/1999 | Siess |
| 6,042,569 | A | 3/2000 | Finch, Jr. et al. |
| 6,139,517 | A | 10/2000 | Macoviak et al. |
| 6,152,945 | A | 11/2000 | Bachinski et al. |
| 6,165,196 | A | 12/2000 | Stack et al. |
| 6,179,796 | B1 | 1/2001 | Waldridge |
| 6,183,492 | B1 | 2/2001 | Hart et al. |
| 6,245,007 | B1 | 6/2001 | Bedingham et al. |
| 6,248,091 | B1 | 6/2001 | Voelker |
| 6,254,563 | B1 | 7/2001 | Macoviak et al. |
| 6,443,884 | B1 | 9/2002 | Miyawaki |
| 6,503,224 | B1 | 1/2003 | Forman et al. |
| 6,524,323 | B1 | 2/2003 | Nash et al. |
| 6,555,057 | B1 | 4/2003 | Bendera |
| 6,616,623 | B1 | 9/2003 | Kutushov |
| 6,635,068 | B1 | 10/2003 | Dubrul et al. |
| 6,699,231 | B1 | 3/2004 | Sterman et al. |
| 6,878,140 | B2 | 4/2005 | Barbut |
| 6,936,057 | B1 | 8/2005 | Nobles |
| 7,022,097 | B2 | 4/2006 | Glickman |
| 7,195,608 | B2 | 3/2007 | Burnett |
| 7,645,259 | B2 | 1/2010 | Goldman |
| 7,766,892 | B2 | 8/2010 | Keren et al. |
| 7,780,628 | B1 | 8/2010 | Keren et al. |
| 8,109,880 | B1 | 2/2012 | Pranevicius et al. |
| 8,126,538 | B2 | 2/2012 | Shuros et al. |
| 8,216,122 | B2 | 7/2012 | Kung |
| 8,480,555 | B2 | 7/2013 | Kung |
| 8,679,057 | B2 | 3/2014 | Fulton, III et al. |
| 9,179,921 | B1 | 11/2015 | Morris |
| 9,358,329 | B2 | 6/2016 | Fitzgerald et al. |
| 9,405,942 | B2 | 8/2016 | Liao et al. |
| 9,421,316 | B2 | 8/2016 | Leeflang et al. |
| 9,433,713 | B2 | 9/2016 | Corbett et al. |
| 9,486,566 | B2 | 11/2016 | Siess |
| 9,533,054 | B2 | 1/2017 | Yan et al. |
| 9,533,084 | B2 | 1/2017 | Siess et al. |
| 9,642,991 | B2 | 5/2017 | Eversull et al. |
| 9,669,142 | B2 | 6/2017 | Spanier et al. |
| 9,669,144 | B2 | 6/2017 | Spanier et al. |
| 9,675,739 | B2 | 6/2017 | Tanner et al. |
| 9,682,223 | B2 | 6/2017 | Callaghan et al. |
| 9,750,861 | B2 | 9/2017 | Hastie et al. |
| 9,770,543 | B2 | 9/2017 | Tanner et al. |
| 9,878,080 | B2 | 1/2018 | Kaiser et al. |
| 9,901,722 | B2 | 2/2018 | Nitzan et al. |
| 9,962,170 | B2 | 5/2018 | Jansen et al. |
| 10,149,684 | B2 | 12/2018 | Nitzan et al. |
| 10,154,846 | B2 | 12/2018 | Nitzan et al. |
| 10,195,405 | B2 | 2/2019 | Nitzan et al. |
| 10,207,086 | B2 | 2/2019 | Nitzan et al. |
| 10,226,604 | B2 | 3/2019 | Nitzan et al. |
| 10,226,605 | B2 | 3/2019 | Nitzan et al. |
| 10,245,363 | B1 | 4/2019 | Rowe |
| 10,285,708 | B2 | 5/2019 | Nitzan et al. |
| 10,300,254 | B2 | 5/2019 | Nitzan et al. |
| 10,639,460 | B2 | 5/2020 | Nitzan et al. |
| 10,653,871 | B2 | 5/2020 | Nitzan et al. |
| 10,709,878 | B2 | 7/2020 | Nitzan et al. |
| 10,912,873 | B2* | 2/2021 | Nitzan ............... A61B 5/02152 |
| 10,926,069 | B2 | 2/2021 | Nitzan et al. |
| 10,960,189 | B2 | 3/2021 | Nitzan et al. |
| 11,007,353 | B2 | 5/2021 | Gerrans et al. |
| 11,166,730 | B2 | 11/2021 | Nitzan et al. |
| 11,179,550 | B2 | 11/2021 | Nitzan et al. |
| 11,179,551 | B2 | 11/2021 | Nitzan et al. |
| 11,179,552 | B2 | 11/2021 | Nitzan et al. |
| 11,357,959 | B2 | 6/2022 | Nitzan et al. |
| 11,406,393 | B2 | 8/2022 | Nitzan |
| 2002/0010418 | A1 | 1/2002 | Lary et al. |
| 2003/0093109 | A1 | 5/2003 | Mauch |
| 2003/0134416 | A1 | 7/2003 | Yamanishi et al. |
| 2003/0208097 | A1 | 11/2003 | Aboul-Hosn et al. |
| 2004/0006306 | A1 | 1/2004 | Evans et al. |
| 2004/0064091 | A1* | 4/2004 | Keren ............... A61B 17/12036 |
| | | | 600/16 |
| 2004/0147871 | A1 | 7/2004 | Burnett |
| 2004/0210296 | A1 | 10/2004 | Schmitt et al. |
| 2004/0230181 | A1 | 11/2004 | Cawood |
| 2005/0085772 | A1 | 4/2005 | Zafirelis et al. |
| 2005/0228474 | A1 | 10/2005 | Laguna |
| 2005/0251180 | A1 | 11/2005 | Burton et al. |
| 2006/0030814 | A1* | 2/2006 | Valencia ............... A61M 25/00 |
| | | | 604/93.01 |
| 2006/0064059 | A1 | 3/2006 | Gelfand et al. |
| 2006/0100658 | A1 | 5/2006 | Obana et al. |
| 2006/0161095 | A1 | 7/2006 | Aboul-Hosn et al. |
| 2006/0178604 | A1 | 8/2006 | Alderman |
| 2007/0055299 | A1 | 3/2007 | Ishimaru et al. |
| 2007/0282303 | A1 | 12/2007 | Nash et al. |
| 2007/0282382 | A1 | 12/2007 | Shuros et al. |
| 2008/0009719 | A1 | 1/2008 | Shuros et al. |

(56) References Cited

U.S. PATENT DOCUMENTS

| | | |
|---|---|---|
| 2008/0015628 A1 | 1/2008 | Dubrul et al. |
| 2008/0071135 A1 | 3/2008 | Shaknovich |
| 2008/0097412 A1 | 4/2008 | Shuros et al. |
| 2008/0103573 A1 | 5/2008 | Gerber |
| 2008/0103591 A1* | 5/2008 | Siess ............... A61M 60/422 623/3.13 |
| 2008/0140000 A1 | 6/2008 | Shuros et al. |
| 2008/0294228 A1 | 11/2008 | Brooke et al. |
| 2009/0018526 A1 | 1/2009 | Power et al. |
| 2009/0112184 A1 | 4/2009 | Fierens et al. |
| 2009/0131785 A1 | 5/2009 | Lee et al. |
| 2010/0168649 A1 | 7/2010 | Schwartz et al. |
| 2010/0179389 A1 | 7/2010 | Moroney et al. |
| 2010/0280451 A1 | 11/2010 | Teeslink et al. |
| 2010/0318114 A1 | 12/2010 | Pranevicius et al. |
| 2011/0004046 A1 | 1/2011 | Campbell et al. |
| 2011/0092955 A1 | 4/2011 | Purdy et al. |
| 2011/0257462 A1 | 10/2011 | Rodefeld et al. |
| 2011/0276023 A1 | 11/2011 | Leeflang et al. |
| 2011/0282274 A1* | 11/2011 | Fulton, III ....... A61B 17/12136 604/27 |
| 2011/0295302 A1 | 12/2011 | Mohl |
| 2012/0029466 A1 | 2/2012 | Callaghan et al. |
| 2012/0157913 A1 | 6/2012 | Aziz et al. |
| 2012/0178986 A1 | 7/2012 | Campbell et al. |
| 2012/0259215 A1 | 10/2012 | Gerrans et al. |
| 2013/0096476 A1 | 4/2013 | Rogachevsky |
| 2013/0096494 A1 | 4/2013 | Kassab |
| 2013/0138041 A1 | 5/2013 | Smisson, III et al. |
| 2013/0177432 A1 | 7/2013 | Toellner et al. |
| 2013/0237954 A1 | 9/2013 | Shuros et al. |
| 2013/0245607 A1 | 9/2013 | Eversull et al. |
| 2013/0303969 A1 | 11/2013 | Keenan et al. |
| 2013/0317535 A1 | 11/2013 | Demmy |
| 2013/0331814 A1 | 12/2013 | Fulton, III et al. |
| 2013/0338559 A1 | 12/2013 | Franano et al. |
| 2014/0010686 A1 | 1/2014 | Tanner et al. |
| 2014/0128659 A1 | 5/2014 | Heuring et al. |
| 2014/0142616 A1 | 5/2014 | Smith |
| 2014/0155815 A1 | 6/2014 | Fulton, III et al. |
| 2014/0220617 A1 | 8/2014 | Yung et al. |
| 2014/0243790 A1 | 8/2014 | Callaghan et al. |
| 2014/0249386 A1 | 9/2014 | Caron et al. |
| 2014/0296615 A1 | 10/2014 | Franano |
| 2014/0303461 A1 | 10/2014 | Callaghan et al. |
| 2014/0336551 A1 | 11/2014 | Mantese et al. |
| 2014/0358036 A1 | 12/2014 | Holmes |
| 2015/0051634 A1 | 2/2015 | Kravik et al. |
| 2015/0157777 A1 | 6/2015 | Tuval et al. |
| 2015/0164662 A1 | 6/2015 | Tuval |
| 2015/0238671 A1 | 8/2015 | Mesallum |
| 2015/0283360 A1 | 10/2015 | Kelly |
| 2015/0343136 A1* | 12/2015 | Nitzan ................ A61M 1/3653 604/27 |
| 2015/0343186 A1 | 12/2015 | Nitzan et al. |
| 2016/0022890 A1 | 1/2016 | Schwammenthal et al. |
| 2016/0045203 A1 | 2/2016 | Pollock |
| 2016/0051741 A1 | 2/2016 | Schwammenthal et al. |
| 2016/0129266 A1 | 5/2016 | Schmidt |
| 2016/0166463 A1 | 6/2016 | Douglas et al. |
| 2016/0169630 A1 | 6/2016 | Augustine et al. |
| 2016/0213826 A1 | 7/2016 | Tanner et al. |
| 2016/0331378 A1 | 11/2016 | Nitzan et al. |
| 2017/0014563 A1* | 1/2017 | Khir ................. A61M 25/1002 |
| 2017/0095395 A1 | 4/2017 | Wennen et al. |
| 2017/0197021 A1 | 7/2017 | Nitzan et al. |
| 2017/0224512 A1 | 8/2017 | Hingston |
| 2017/0319764 A1 | 11/2017 | Tanner et al. |
| 2018/0012630 A1 | 1/2018 | Thomee et al. |
| 2018/0020456 A1 | 1/2018 | Wan et al. |
| 2018/0125499 A1 | 5/2018 | Nitzan et al. |
| 2018/0126130 A1 | 5/2018 | Nitzan et al. |
| 2018/0146968 A1 | 5/2018 | Nitzan et al. |
| 2018/0185622 A1 | 7/2018 | Nitzan et al. |
| 2018/0193614 A1 | 7/2018 | Nitzan et al. |
| 2018/0193615 A1 | 7/2018 | Nitzan et al. |
| 2018/0193616 A1 | 7/2018 | Nitzan et al. |
| 2018/0250456 A1 | 9/2018 | Nitzan et al. |
| 2018/0303986 A1 | 10/2018 | Meacham |
| 2019/0014991 A1 | 1/2019 | Maki et al. |
| 2019/0046706 A1 | 2/2019 | Aboul-Hosn et al. |
| 2019/0046707 A1 | 2/2019 | Aboul-Hosn et al. |
| 2019/0083761 A1 | 3/2019 | Nitzan et al. |
| 2019/0117943 A1 | 4/2019 | Nitzan et al. |
| 2019/0117944 A1 | 4/2019 | Nitzan et al. |
| 2019/0126014 A1 | 5/2019 | Kapur et al. |
| 2019/0167878 A1 | 6/2019 | Rowe |
| 2019/0223877 A1 | 7/2019 | Nitzan et al. |
| 2019/0366063 A1 | 12/2019 | Nitzan et al. |
| 2020/0016383 A1 | 1/2020 | Nitzan et al. |
| 2020/0030586 A1 | 1/2020 | Nitzan et al. |
| 2020/0030587 A1 | 1/2020 | Nitzan et al. |
| 2020/0046372 A1 | 2/2020 | Nitzan |
| 2020/0206485 A1 | 7/2020 | Nitzan et al. |
| 2020/0230380 A1 | 7/2020 | Nitzan et al. |
| 2020/0230381 A1 | 7/2020 | Nitzan et al. |
| 2020/0261706 A1 | 8/2020 | Nitzan et al. |
| 2020/0268951 A1 | 8/2020 | Nitzan et al. |
| 2020/0268952 A1 | 8/2020 | Nitzan et al. |
| 2020/0268954 A1 | 8/2020 | Nitzan et al. |
| 2020/0269025 A1 | 8/2020 | Nitzan et al. |
| 2020/0276369 A1 | 9/2020 | Nitzan et al. |
| 2020/0306436 A1 | 10/2020 | Tanner et al. |
| 2020/0397963 A1 | 12/2020 | Nitzan et al. |
| 2021/0121678 A1 | 4/2021 | Nitzan et al. |
| 2021/0378676 A1 | 12/2021 | Keating et al. |
| 2021/0378677 A1 | 12/2021 | Keating et al. |
| 2021/0378678 A1 | 12/2021 | Keating et al. |
| 2021/0379329 A1 | 12/2021 | Keating et al. |
| 2022/0039803 A1 | 2/2022 | Nitzan et al. |
| 2022/0104827 A1 | 4/2022 | Keating et al. |
| 2022/0104828 A1 | 4/2022 | Keating et al. |
| 2022/0218360 A1 | 7/2022 | Nitzan et al. |
| 2022/0218961 A1 | 7/2022 | Nitzan et al. |
| 2022/0280761 A1 | 9/2022 | Nitzan et al. |
| 2022/0280762 A1 | 9/2022 | Nitzan et al. |
| 2022/0331510 A1 | 10/2022 | Amstutz et al. |
| 2023/0007905 A1 | 1/2023 | Tschopp et al. |

FOREIGN PATENT DOCUMENTS

| | | |
|---|---|---|
| EP | 2353501 A1 | 8/2011 |
| EP | 2353503 A1 | 8/2011 |
| EP | 2353632 A1 | 8/2011 |
| EP | 2497524 A1 | 9/2012 |
| EP | 2637927 A1 | 9/2013 |
| EP | 2662099 A1 | 11/2013 |
| JP | 2000-511442 A | 9/2000 |
| JP | 2001-515375 A | 9/2001 |
| JP | 2002-536079 A | 10/2002 |
| WO | 89/04193 A1 | 5/1989 |
| WO | 2000/024337 A2 | 5/2000 |
| WO | 01/013983 A2 | 3/2001 |
| WO | 2010/078603 A2 | 7/2010 |
| WO | 2012/135834 A2 | 10/2012 |
| WO | 2013/025826 A1 | 2/2013 |
| WO | 2013/061281 A1 | 5/2013 |
| WO | 2014/141284 A2 | 9/2014 |
| WO | 2014/141287 A1 | 9/2014 |
| WO | 2015/186003 A2 | 12/2015 |
| WO | 2017/087556 A1 | 5/2017 |
| WO | 2018/158636 A1 | 9/2018 |
| WO | 2018172848 A2 | 9/2018 |
| WO | 2018/202776 A1 | 11/2018 |
| WO | 2019/027380 A1 | 2/2019 |
| WO | 2020/174285 A2 | 9/2020 |
| WO | 2021/115562 A1 | 6/2021 |

OTHER PUBLICATIONS

Biran, 2017, Heparin coatings for improving blood compatibility of medical devices, Adv Drug Delivery Rev, 112:12-23.

(56) References Cited

OTHER PUBLICATIONS

Blitz, 2014, Pump thrombosis—a riddle wrapped in a mystery inside an enigma, Ann Cardiothorac Surg, 3(5):450-471.
Chikly, 2005, Manual techniques addressing the lymphatic system: origins and development, JAOA 105(10):457-464.
Moscucci, 2014, Section III Hemodynamic principles 10 Pressure measurement, 223-244 in Grossman & Baim's Cardiac Catheterization, Angiography, and Intervention 8 Ed, 26 pages.
Ratnayake, 2018, The Anatomy and physiology of the terminal thoracic duct and ostial valve in health and disease: potential implications for intervention, J Anat 233:1-14.
Shimizu, 2014, Embolization of a fractured central venous catheter placed using the internal jugular apporach, Int J Surg Case Rep 5:219-221.
Stone, 2010, The effect of rigid cervical collars on internal jugular vein dimensions, Acad Emerg Med 17(1):100-102.
Swan, 1970, Catheterization of the Heart in Man with Use of a Flow-directed Balloon-tipped Catheter, NEJM 283(9):447-451.
Tchantchaleishvili, 2014, Evaluation and treatment of pump thrombosis and hemolysis, Ann Cardiothorac Surg, 3(5):490-495.
Webb, 2012, Roughness parameters for standard description of surface nanoarchitecture, Scanning 34:257-263.
Yancy, 2013, 2013 ACCF/AHA Guideline for the Management of Heart Failure, Circulation 128(16):e240-e327.

\* cited by examiner

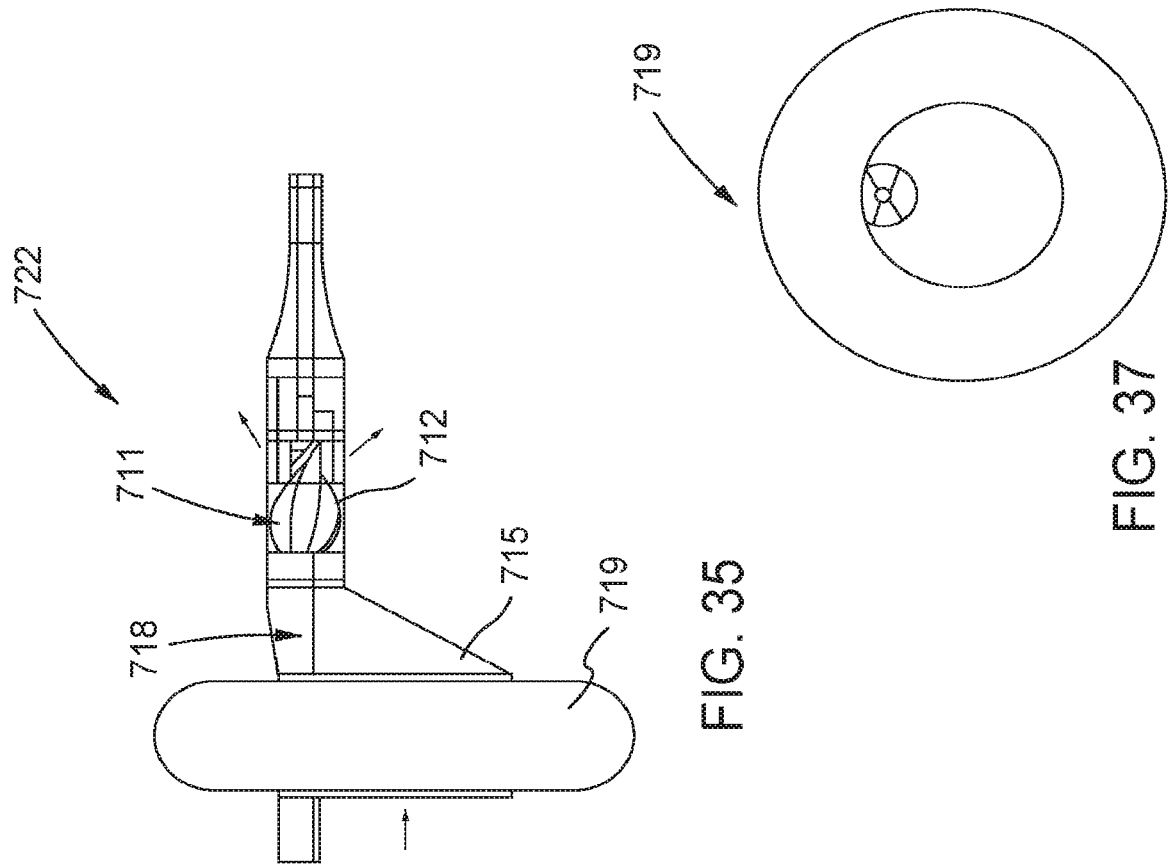
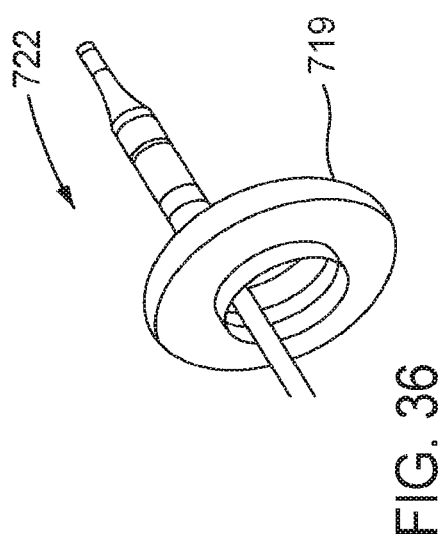

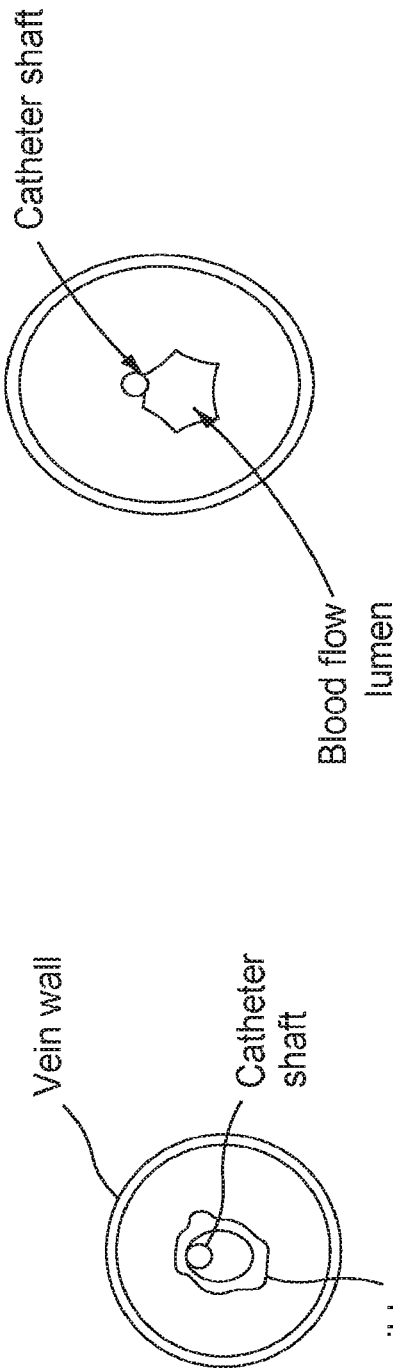
FIG. 54
FIG. 55
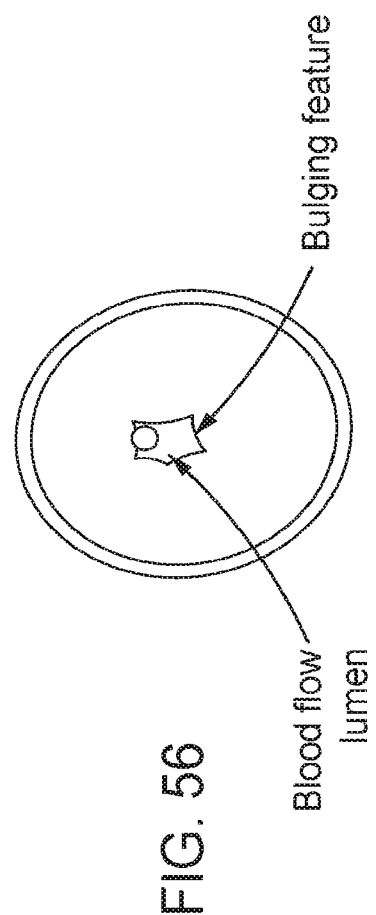
FIG. 56

| Step | Action | Ultrasound Verification |
|---|---|---|
| S1 | Extract the catheter from the sterile package | - |
| S2 | Sheathing of catheter distal and proximal units and flush | - |
| S3 | Trackability of catheter over a guidewire | - |
| S4 | Catheter crossing subclavian | Yes |
| S5 | Un-sheathe the distal and proximal units | Yes |
| S6 | Pull out guidewire | - |
| S7 | Suture the sheath | Yes |
| S8 | Connect the electrical cable | Yes |
| S9 | Operate the motor for suction | - |
| S10 | Inflate the distal restrictor | Yes |
| S11 | Inflate the proximal restrictor | Yes |
| S12 | Operate the motor in an automatic state | Yes |
| S13 | Adjustment of the proximal restrictor to allow Δ in CVP | Yes |
| | Retrieval | |
| S14 | Balloon deflation and motor stop | Yes |
| S15 | Open sutures | Yes |
| S16 | Sheath the proximal and distal assembly into catheter | Yes |
| S17 | Withdrawal of the catheter out of patient | - |

FIG. 62

SYSTEMS AND METHODS FOR REDUCING PRESSURE AT AN OUTFLOW OF A DUCT

CROSS-REFERENCE TO RELATED APPLICATION(S)

This application is a continuation of U.S. nonprovisional application Ser. No. 17/141,937, filed Jan. 5, 2021, (now issued as U.S. Pat. No. 11,793,995) which claims priority to U.S. application Ser. No. 15/909,290, filed Mar. 1, 2018, (now issued as U.S. Pat. No. 10,912,873) which claims priority to U.S. Provisional Application No. 62/466,191, filed Mar. 2, 2017, the contents of which are incorporated by reference herein.

FIELD

The present disclosure relates generally to systems and methods for reducing pressure at an outflow of a duct.

BACKGROUND

The lymphatic system is part of the circulatory system in conjunction with the arterial and venous systems. A primary function of the lymphatic system is to drain excessive interstitial fluid back into the venous system at two main locations: the thoracic duct and the lymphatic duct, which drain into the left and right subclavian veins, respectively.

Under normal circulatory conditions of the arterial and venous systems the interstitial fluid volume balance is maintained and the lymph fluid is cleared back through the lymphatic system. In pathological conditions such as Acute Cardiogenic Pulmonary Edema and chronic heart failure, the capillary hydrostatic pressure and the venous pulmonary pressure can become elevated and fluid flows excessively out of the blood vessels and into the interstitial and alveolar spaces. The pressure gradient between the initial lymphatics and at the outflow of the thoracic duct and the lymphatic duct is reduced and the lymphatic system cannot clear the additional fluid which accumulates in the air spaces of the lungs. This is a life threatening condition as gas exchange is impaired to the extent that it may lead to respiratory failure.

Current treatment methods require extended hospitalization and treatment with loop diuretics and/or vasodilators. Oftentimes patients must also receive supplemental oxygen or, in more extreme cases, require mechanical ventilation. Many of these treatment methods are less than ideal because the edema is not always alleviated rapidly enough and for many patients renal function is adversely affected. A significant percentage of patients do not respond to this treatment and a significant percentage must be readmitted to a hospital within thirty days.

A significant problem with current treatment protocol is that it is based on the need to reduce intravascular blood pressure to move interstitial and lymphatic fluid back into the vasculature. The reduction of intravascular blood pressure may lead to hypotension and may activate the Renin Angiotensin Aldosterone System, which may lead back to an increase in blood pressure or to worsening of renal function. Eventually, this cycle leads to diuretic resistance and the worsening of renal function in almost 30% of admitted patients. The lymphatic system can directly drain fluids from the interstitial compartment into the intravascular compartment and by such to relief edema.

The lymphatic system drains the interstitial fluids via the thoracic duct and right lymphatic duct that drain into the region around the bifurcation of the left subclavian vein and left internal jugular vein for the thoracic duct and into the bifurcation of the right internal jugular vein and right subclavian vein for the right lymphatic duct. However, in conditions such as acutely decompensated heart failure the lymphatic return is reduced as a result of elevated central venous pressure (CVP). Therefore, as a result of the elevated CVP, the lymphatic return is greatly reduced.

Accordingly, there remains a need for improved systems and methods for reducing pressure at an outflow of a duct such as the thoracic duct or the lymphatic duct.

SUMMARY

Systems and methods are provided for reducing pressure at an outflow of a duct, such as the thoracic duct or the lymphatic duct, and other parts of the venous system. Systems and methods for reducing venous pressure are provided. An indwelling catheter can be configured to be at least partially implanted within a vein of a patient in the vicinity of an outflow port of a duct of the lymphatic system. The catheter is configured to provide a tunnel or lumen a blood flow through which is controlled. A size of the lumen is controlled so as to cause the heart, during its diastolic phase, to pump in (suck) blood harder thereby reducing pressures within the heart and at an outlet of a duct.

In certain aspects, the invention provides a catheter system. The catheter system includes a catheter shaft configured to be at partially implanted within a blood vessel of a patient, an impeller assembly disposed at a distal portion of the catheter shaft, a flexible membrane connected to the impeller assembly, and a selectively deployable restrictor attached to the distal portion via the flexible membrane. Deployment of the restrictor causes the flexible membrane to assume a tapered configuration, defining a tapered lumen extending through the restrictor, the flexible membrane, and at least a portion of the impeller assembly. The system may include an inflation lumen extending at least partially through the catheter shaft, the at least one inflation lumen being in fluid communication with the restrictor. In some embodiments, the restrictor comprises a selectively expandable balloon coupled to an outer wall of the flexible membrane.

The restrictor may control the size of the tapered lumen by constricting at least a portion of the flexible membrane when the restrictor is in an expanded configuration. The flexible membrane may be oriented so as to be substantially parallel to the catheter shaft.

In certain embodiments, at least a portion of the tapered lumen has a diameter from about 1 mm to about 4 mm when the restrictor is in an expanded configuration. A diameter of the catheter shaft may be, e.g., from about 4 Fr to about 9 Fr. Preferably, the blood vessel is one of an internal jugular vein and a subclavian vein.

The restrictor may be mounted on a support ring at a proximal end of the tapered membrane, wherein the support ring comprises a guide channel holding a drive shaft of the impeller. The impeller housing may have windows along a distal portion thereof. Preferably, when the distal portion is in the blood vessel and the restrictor is deployed and the impeller is driven, the impeller draws blood through the tapered lumen.

The catheter system may include an atraumatic tip extending distally of the impeller housing; a driveshaft extending at least partially through the elongate member; or both. Optionally, the system may include a proximal assembly, the proximal assembly comprising a sheath (e.g., with a second restrictor) through which the elongate member is slideably disposed.

In related aspects, the invention provides a method of treating reducing pressure at an outflow of a duct. The method includes positioning, in a blood vessel near an output of a duct, a device comprising a tapered lumen and pumping blood from a wide end of the tapered lumen to a narrow end to thereby lower pressure near the output of the duct. Preferably, the device has a restrictor with an opening therethrough and a housing member, and the tapered lumen is provided by a flexible membrane that tapers from the opening to the housing member, and further wherein the blood is pumped by operating an impeller within the device. The restrictor occludes the blood vessel (e.g., a jugular vein or a subclavian vein) but for the opening therethrough. In certain embodiments, the housing member houses the impeller, the device further comprising an elongate driveshaft extending proximally from the impeller, wherein the blood flows out of the housing member via one or more aperture along the side of the housing member. Preferably, the restrictor comprises an inflatable balloon and the method further comprises inflating the balloon when the device is positioned in the body lumen.

In some aspects, a catheter system configured to be placed within a vein of a patient is provided that in some embodiments includes a catheter shaft, a flexible membrane, and a single selectively deployable restriction member. The catheter shaft is configured to be at least partially implantable within a patient's vein. The flexible membrane is attached to the catheter shaft, and the flexible membrane is a collapsible, tube-like member having a lumen extending therethrough. The single selectively deployable restriction member is formed over a portion of the flexible membrane at substantially a midpoint between a proximal end of the flexible membrane and a distal end of the flexible membrane, the restriction member being configured to control a size of the lumen so as to direct a controlled volume of fluid from an upstream side of the restriction member to a downstream side the restriction member.

The catheter system can vary in different ways. For example, the catheter can be an implantable catheter. The restriction member can be configured to control the size of the lumen so as to direct the controlled volume of fluid from the upstream side of the restriction member to the downstream side the restriction member by causing a pumping force of the heart during diastole to be increased.

In at least some embodiments, the catheter system includes at least one inflation lumen extending at least partially through the catheter shaft, the at least one inflation lumen being in fluid communication with the restriction member.

In at least some embodiments, the flexible membrane is oriented so as to be substantially parallel to the catheter shaft.

In at least some embodiments, the restriction member includes a selectively expandable balloon coupled to an outer wall of the flexible membrane. In at least some embodiments, the balloon can be configured, in an expanded configuration, to expand at least in part inwardly towards the flexible membrane so as to at least partially constrict the membrane. For example, in some embodiments, the balloon is configured, in the expanded configuration, to have at least one bulging feature at least partially constricting the membrane.

In at least some embodiments, at least a portion of the lumen has a diameter from about 1 mm to about 4 mm when the restriction member is in an expanded configuration. A diameter of the catheter shaft can be from about 4 Fr to about 9 Fr.

The vein can be one of an internal jugular vein and a subclavian vein. The restriction member can be configured to control the size of the lumen by constricting at least a portion of the flexible membrane when the restriction member is in an expanded configuration.

In other aspects, a catheter system configured to be implantable within a vein of a patient is provided that in some embodiments includes a catheter shaft, a selectively deployable restriction member, and a flow regulation component. The catheter shaft is configured to be at least partially implantable within a patient's vein and having a lumen extending therethrough. The selectively deployable restriction member is formed over a portion of the catheter shaft and has the lumen extending therethrough, the restriction member being configured to be activated to at least partially occlude the vein. The flow regulation component disposed proximally to the restriction member and configured to control a volume of fluid from an upstream side of the restriction member to a downstream side the restriction member.

The catheter system can vary in different ways. For example, the vein is one of an internal jugular vein and a subclavian vein. As another example, the restriction member is a selectively expandable balloon.

In another aspect, a medical method is provided that in some embodiments involves implanting a catheter within a vein of a patient, the catheter having coupled thereto a selectively deployable single restriction member that has a lumen extending therethrough, the restriction member being positioned at a location within the vein that is upstream of an outflow port of a duct of the patient's venous system. The method also includes actuating the restrictor to move the restrictor from a relaxed configuration to an activated configuration thereby limiting fluid flow within the vein and past the single restriction member so as to create a low pressure region within the vein downstream of the restrictor.

The method can vary in different ways. For example, the method can include creating blood flow restriction upstream of the single restriction member so as to create the low pressure region downstream of the single restriction member. As another example, a pressure upstream of the single restriction member can be greater than a pressure downstream of the single restriction member. As a further example, a pressure in the low pressure region can be substantially the same as a pressure in other parts of the patient's venous system except a part of the patient's venous system upstream of the single restriction member.

In at least some embodiments, limiting fluid flow within the vein and past the single restriction member includes controlling a volume of fluid through the lumen.

BRIEF DESCRIPTION OF DRAWING

FIG. 35 illustrates a distal assembly of the implantable system of FIG. 33.

FIG. 36 is a perspective view of the distal assembly of the catheter system.

FIG. 37 is a back view back view of the distal assembly.

FIG. 54 is a first step in a process of activation of a balloon and a flexible membrane of a catheter.

FIG. 55 is a second step in a process of activation of a balloon and a flexible membrane of a catheter.

FIG. 56 is a third step in a process of activation of a balloon and a flexible membrane of a catheter.

FIG. 62 diagrams a method of implanting a catheter.

DETAILED DESCRIPTION

Figure 1:
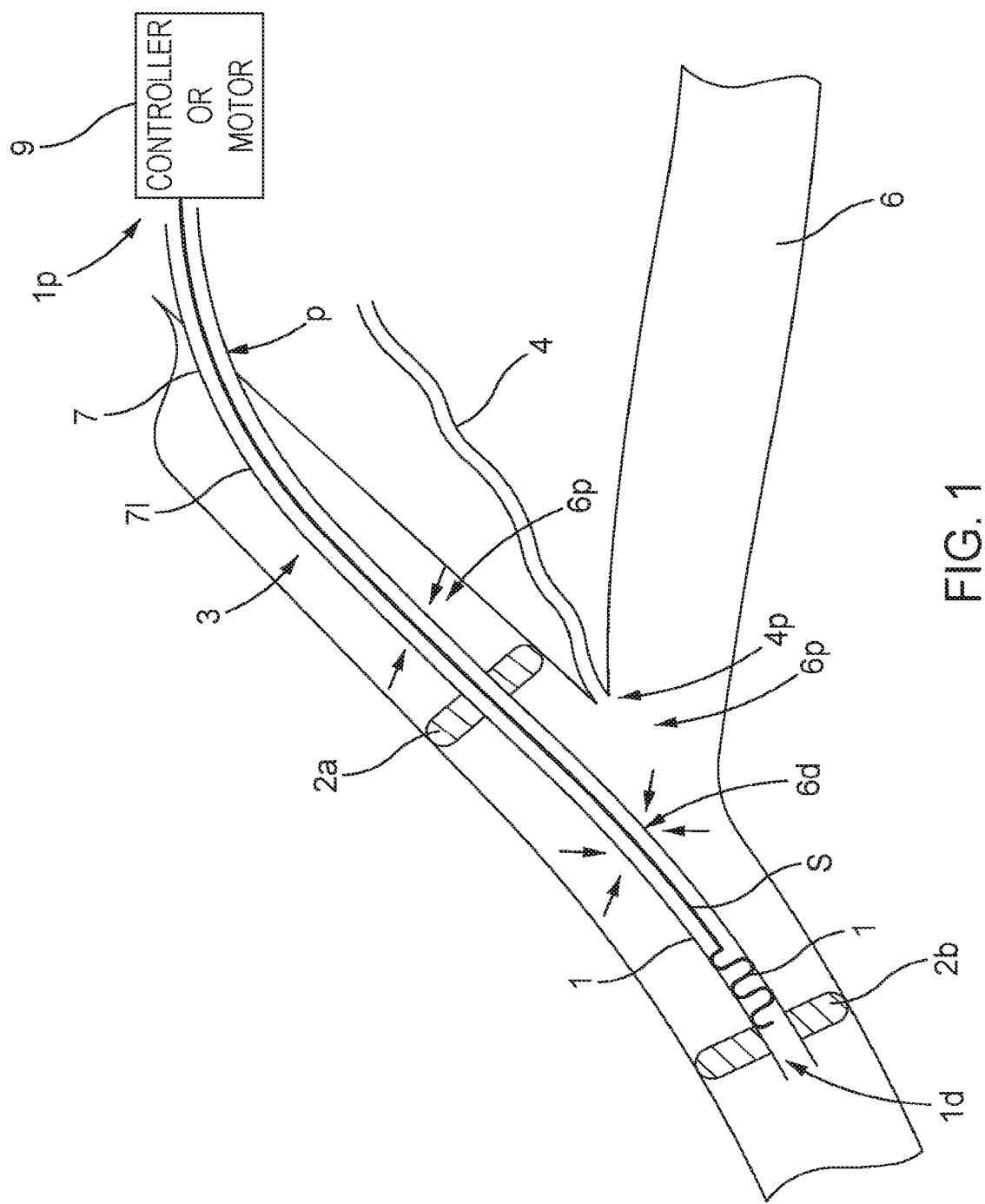
FIG. 1 is a schematic cross-sectional view of a catheter implanted in a vein of a patient.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Reference throughout the specification to "various embodiments," "some embodiments," "one embodiment," or "an embodiment," or the like, means that a particular feature, structure, or characteristic described in connection with the embodiment is included in at least one embodiment. Thus, appearances of the phrases "in various embodiments," "in some embodiments," "in one embodiment," or "in an embodiment," or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features structures, or characteristics of one or more other embodiments without limitation.

It will be appreciated that the terms "proximal" and "distal" may be used throughout the specification with reference to a clinician manipulating one end of an instrument used to treat a patient. The term "proximal" refers to the portion of the instrument closest to the clinician and the term "distal" refers to the portion located furthest from the clinician. It will be further appreciated that for conciseness and clarity, spatial terms such as "vertical," "horizontal," "up," and "down" may be used herein with respect to the illustrated embodiments. However, surgical instruments may be used in many orientations and positions, and these terms are not intended to be limiting and absolute.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

Various systems and methods are provided for reducing pressure at an outflow of a duct such as the thoracic duct or the lymphatic duct. In general, the systems and methods may be effective to reduce edema conditions, such as pulmonary edema, in a patient by lowering an outflow pressure in a region around the patient's thoracic/lymphatic duct outflow. As a result of lowering the outflow pressure at the thoracic and/or lymphatic ducts, higher lymphatic return will be achieved, enabling the lymphatic vessel flow to be at or near normal levels. The systems and methods may be effective to rapidly alleviate conditions of the edema and increase the patient response rate. In an exemplary embodiment, the systems and methods may be particularly useful to treat acute pulmonary edema; however a person skilled in the art will appreciate that the systems and methods can be used in various procedures for treating a lymphatic system fluid clearance imbalance.

An indwelling catheter can be configured to be at least partially implanted (e.g., partially implanted or fully implanted) within a vein of a patient in the vicinity of an outflow port of a duct of the lymphatic system, e.g., in the vicinity of an outflow port of the thoracic duct or in the vicinity of an outflow port of the lymphatic duct. Exemplary materials from which the catheter can be made include polyurethanes. The catheter can include first and second restrictors (also referred to herein as "restriction members") each configured to at least partially occlude the vein within which the catheter is implanted and thus to restrict fluid flow within the vein when the restrictors are activated. The restrictors can each be configured to move between an activated configuration, in which the restrictor occludes the vein, and a relaxed configuration, in which the restrictor does not occlude the vein. The restrictors can each be in the relaxed configuration during implantation of the catheter to ease introduction of the catheter into the patient's body and into the vein. Each of the restrictors can include a balloon configured to be inflated where in the relaxed configuration the balloon is not inflated and in the activated configuration in which the balloon is inflated. The restrictors can be made from any one or more of a variety of materials configured to expand upon the delivery of a fluid thereto and to contract upon the withdrawal of the fluid. Exemplary materials from which the balloon can be made include polymeric materials such as PEBAX, silicones, polyurethanes, and nylons. The catheter can include at least one inflation lumen through which an inflation fluid (e.g., air, liquid, etc.) can be introduced to inflate/deflate the restrictors. The at least one inflation lumen can include one lumen in fluid communication with both of the restrictors such that the restrictors can be simultaneously inflated/deflated, or can include first and second lumens with the first lumen in fluid communication with the first restrictor and the second lumen in fluid communication with the second restrictor such that the restrictors can be selectively inflated simultaneously or sequentially. The catheter can include a pump, such as an axial motor pump, configured to pump fluid through the catheter. The catheter can be coupled to a motor configured to drive the pump. The motor can be included in the catheter (e.g., within a shaft of the catheter) and be configured to be implanted with the catheter, or the motor can be located outside of the catheter (e.g., outside of the catheter's shaft) and be configured to be located outside of the patient rather than be implanted therein.

In one embodiment of using the catheter, the catheter can be positioned at a desired location within the vein. The first and second restrictors can then each be activated (simultaneously or sequentially) to move from the relaxed configuration to the activated configuration. The first and the second restrictors, when activated so as to provide two occlusions within the vein, define a low pressure zone between the first and second restrictors within a portion of the vein in which the catheter is positioned. Higher pressure zones accordingly exist on either side of the restrictors. The motor can drive the pump to induce the low pressure zone by causing fluid to be pumped through the catheter. The catheter and the restrictors can be positioned within the vein such that the low pressure zone is adjacent to an outflow port of a duct (e.g., the thoracic duct or the lymphatic duct) to allow fluid to pass from the lymph duct outflow port to the portion of the catheter housed within the vein so that fluid can flow out of the catheter.

In at least some embodiments, the restrictor(s) of a catheter can be inflated and deflated from time to time to enable free flow of blood in a patient's vein in which the restrictor(s) are positioned and thus enable the system to stop working for a period of time. This period of time can be required in such treatments to allow for the assessment of the patient's clinical condition, allow the patient to undergo other treatments or enable him to go to the bathroom and/or to wash any stagnation points that might have occurred.

The catheters described herein can be configured to be placed in a patient's body for up to about seventy-two hours, e.g., the catheter can be indwelled in the body for up to about seventy-two hours. The catheter systems described herein that include the catheters can be operated in a treatment time period in a range of about 6 to 8 hours. At the end of each treatment period, the restrictors are deflated, the catheter can be filled with a heparin catheter locking solution, and an assessment of the patient's clinical condition can be performed. The catheter system can be operated again if desired by medical personnel. Within the indwelling period of the catheter, a number of treatment periods can be in a range of 3 to 6 cycles, e.g., for a maximum of about forty hours of operation within a seventy-two hour indwelling period.

A person skilled in the art will appreciate that the systems and methods disclosed herein can be used with a variety of surgical devices, including measuring devices, sensing devices, locator devices, insertion devices, etc.

Furthermore, various systems and methods are provided for reducing pressure at an outflow of a duct such as the thoracic duct or the lymphatic duct. In general, the systems and methods may be effective to reduce edema conditions, such as pulmonary edema, in a patient by lowering an outflow pressure in a region around the patient's thoracic/lymphatic duct outflow. As a result of lowering the outflow pressure at the thoracic and/or lymphatic ducts, higher lymphatic return will be achieved, enabling the lymphatic vessel flow to be at or near normal levels. The systems and methods may be effective to rapidly alleviate conditions of the edema and increase the patient response rate. In an exemplary embodiment, the systems and methods may be particularly useful to treat acute pulmonary edema. However, a person skilled in the art will appreciate that the systems and methods can be used in various procedures for treating a lymphatic system fluid clearance imbalance.

An indwelling catheter can be configured to be at least partially implanted (e.g., partially implanted or fully implanted) within a vein of a patient in the vicinity of an outflow port of a duct of the lymphatic system, e.g., in the vicinity of an outflow port of the thoracic duct or in the vicinity of an outflow port of the lymphatic duct. Exemplary materials from which the catheter can be made include polyurethanes. The catheter can include first and second restrictors (also referred to herein as "restriction members"), at least one of which is configured to at least partially occlude the vein within which the catheter is implanted and thus to restrict fluid flow within the vein when at least one of the restrictors is activated. The restrictors can each be configured to move between an activated configuration, in which the restrictor occludes the vein, and a relaxed configuration, in which the restrictor does not occlude the vein. The restrictors can each be in the relaxed configuration during implantation of the catheter to ease introduction of the catheter into the patient's body and into the vein. Each of the restrictors can include a balloon configured to be inflated, where in the relaxed configuration the balloon is not inflated and in the activated configuration in which the balloon is inflated.

The restrictors can be made from any one or more of a variety of materials configured to expand upon the delivery of a fluid thereto and to contract upon the withdrawal of the fluid. Exemplary materials from which the balloon can be made include polymeric materials such as PEBAX, silicones, polyurethanes, and nylons. The catheter can include at least one inflation lumen through which an inflation fluid (e.g., air, liquid, etc.) can be introduced to inflate/deflate the restrictors. The at least one inflation lumen can include one lumen in fluid communication with both of the restrictors such that the restrictors can be simultaneously inflated/deflated, or can include first and second lumens with the first lumen in fluid communication with the first restrictor and the second lumen in fluid communication with the second restrictor such that the restrictors can be selectively inflated simultaneously or sequentially. The catheter can include a pump, such as an axial motor pump, configured to pump fluid through the catheter. The catheter can be coupled to a motor configured to drive the pump. The motor can be included in the catheter (e.g., within a shaft of the catheter) and be configured to be implanted with the catheter, or the motor can be located outside of the catheter (e.g., outside of the catheter's shaft) and be configured to be located outside of the patient rather than be implanted therein.

The catheter can be positioned at a desired location within the vein. The first and second restrictors can then each be activated (simultaneously or sequentially) to move from the relaxed configuration to the activated configuration. The first and the second restrictors, when activated so as to provide, in combination with other components, occlusion within the vein, define a low pressure zone between first and the second restrictors within a portion of the vein in which the catheter is positioned. Higher pressure zones accordingly exist on either side of the restrictors. The motor can drive an impeller to induce the low pressure zone by causing fluid to be pumped through the catheter. The catheter and the restrictors can be positioned within the vein such that the low pressure zone is adjacent to an outflow port of a duct (e.g., the thoracic duct or the lymphatic duct) to allow fluid to pass from the lymph duct outflow port to the portion of the catheter housed within the vein so that fluid can flow out of the catheter.

In at least some embodiments, at least one of the restrictors of a catheter can be inflated and deflated from time to time to enable free flow of blood in a patient's vein in which the restrictor(s) are positioned and thus enable the system to stop working for a period of time. This period of time can be required in such treatments to allow for the assessment of the patient's clinical condition, allow the patient to undergo other treatments or enable him to go to the bathroom and/or to wash any stagnation points that might have occurred. Each of the restrictors can be configured and operated as described, for example, in U.S. application Ser. No. 14/625,930 entitled "System And Method For Treating Pulmonary Edema," filed Feb. 19, 2015, and in U.S. application Ser. No. 14/726,715 entitled "Systems and Methods for Treating Pulmonary Edema," filed Jun. 1, 2015, the content of each of which is incorporated by reference herein in its entirety. In addition, some features of the catheter system described herein can be implemented as described in U.S. App. Publ. No. 2016/0331378 entitled "Systems and Methods for Reducing Pressure at an Outflow of a Duct," filed May 10, 2016, the content of which is incorporated by reference herein in its entirety.

In some embodiments, the catheters can be configured to be placed in a patient's body for up to about seventy-two hours, e.g., the catheter can be indwelled in the body for up to about seventy-two hours. The catheter systems are configured to be able to be accurately fixated and deployed in a patient's body. The systems can be configured to be conveniently placed to a desired location in a patient (torque can be applied), and they possess compatibility with a guide wire and sheath, ability to overcome leads and leads effects, ability to automatically maintain a working point for 72 hours (<5 mmHg at the isolated zone), and ability to measure pressure at the pressure reduction zone. It should be appreciated, however, that in other instances a catheter system in accordance with the described techniques can be indwelled in the body for duration of time greater than seventy-two hours—for example, several days or weeks. The system can be configured to maintain hemostasis.

In some embodiments, a catheter can include a single restrictor configured to at least partially occlude the vein within which the catheter is implanted and thus to restrict fluid flow within the vein when the restrictor is activated. In such embodiments, a pressure at the lymphatic outflow can be reduced by inflating the single restrictor such as a proximal balloon, without the need to inflate a distal balloon. However, it should be appreciated that the catheter can include both distal and proximal balloons and only the proximal one of the balloons can be used.

A person skilled in the art will appreciate that the systems and methods disclosed herein can be used with a variety of surgical devices, including measuring devices, sensing devices, locator devices, insertion devices, etc.

FIG. 1 illustrates one embodiment of a catheter 1 that includes at least one restrictor 2a, 2b. The at least one restrictor includes first and second restrictors 2a, 2b in this illustrated embodiment, which each include a balloon configured to be inflated (corresponding to an activated configuration) and deflated (corresponding to a relaxed configuration). The first and second restrictors 2a, 2b can be spaced a distance apart from one another along a longitudinal length of the catheter 1 such that one of the restrictors 2b is more distal than the other of the restrictors 2a. The distance between the first and second restrictors 2a, 2b can define a length of a low pressure zone that can be created when the catheter 1 is implanted within a vein. FIG. 1 shows the catheter 1 positioned within an internal jugular vein 3 of a patient with the distal restrictor 2b positioned distal to an outflow port 4p of the patient's thoracic duct 4 and the proximal restrictor 2a positioned proximal to the outflow port 4p of the patient's thoracic duct 4. The low pressure zone defined between the proximal and distal (first and second) restrictors 2a, 2b can thus be located adjacent the outflow port 4p of the thoracic duct 4. The proximal restrictor 2a being positioned proximal to (e.g., upstream) of the outflow port 4p of the thoracic duct 4 may help prevent back flow from the patient's subclavian vein 5 while providing the low pressure zone and benefit(s) thereof. The catheter 1 can be similarly positioned on a right side of the patient with the distal restrictor 2b positioned distal to an outflow port of the patient's subclavian vein 5 and an outflow port of the patient's lymphatic duct (not shown) and the proximal restrictor 2a positioned proximal to the outflow port of the patient's subclavian vein 5 and the outflow port of the patient's lymphatic duct.

The catheter 1 can include at least one inflation lumen (omitted from FIG. 1 for clarity of illustration) configured to facilitate inflation of the first and second restrictors 2a, 2b, e.g., to facilitate movement of the restrictors 2a, 2b between the activated and relaxed configurations. The first and second restrictors 2a, 2b are shown in the activated configuration in FIG. 1 with the first and second restrictors 2a, 2b each abutting an internal surface of the jugular vein 3 so as to provide two, spaced-apart occlusions therein.

The catheter 1 can include a shaft 7 having a lumen 7L, as shown in this illustrated embodiment, configured to communicate fluid therethrough so as to accommodate the flow of fluid in a vein in which the catheter 1 is implanted. The shaft 7 can have a variety of sizes, such as having a diameter that is in the range of about 8 to 18 Fr (e.g., about 8 Fr, equal to or less than about 12 Fr, etc.) and having a length in the range of about 25 to 40 cm.

The first and second restrictors 2a, 2b can be attached to and surround the shaft 7. The first and second restrictors 2a, 2b can each be formed in the shape of a torus, as in this illustrated embodiment, to facilitate the surrounding of the shaft 1 and/or to help prevent compression of the restrictors 2a, 2b when they are moved radially outward during expansion thereof and thereby thus overcoming a possible tendency for the restrictors 2a, 2b to collapse in response to an external pressure. The first and second restrictors 2a, 2b can, however, have other shapes.

The catheter 1 can have a first or distal suction inlet 8d formed through the shaft's sidewall. The distal suction inlet can be in communication with the lumen 7L so as to allow fluid to enter the lumen 7L therethrough, as shown in FIG. 1 by four arrows at the distal suction inlet 8d pointing inward toward the lumen 7L. The distal suction inlet 8d can include any number of openings formed through the shaft's sidewall. The openings can have any of a variety of configurations, e.g., slits, circular holes, ovular holes, rectangular slots, etc. The distal suction inlet 8d can be located along the catheter's longitudinal length at a position between the first and second restrictors 2a, 2b. The distal suction inlet 8d can thus be located within the low pressure zone. In an exemplary embodiment, as shown in FIG. 1, in use, the distal suction inlet 8d can be positioned adjacent the outflow ports 4p, 5p of the thoracic duct 4 and the subclavian vein 5 so as to allow fluid exiting the outflow ports 4p, 5p to enter the catheter 1.

The catheter 1 can include a second or proximal suction inlet 8p formed through the shaft's sidewall. The proximal suction inlet 8p can be in communication with the lumen 7L so as to allow fluid to enter the catheter's lumen 7L therethrough, as shown in FIG. 1 by two arrows at the proximal suction inlet 8p pointing inward toward the lumen 7L. The proximal suction inlet 8p can include any number of openings formed through the shaft's sidewall. The openings can have any of a variety of configurations, e.g., slits, circular holes, ovular holes, rectangular slots, etc. The proximal suction inlet 8p can be located proximal to the distal suction inlet 8d and proximal to the first and second restrictors 2a, 2b. In an exemplary embodiment, as shown in FIG. 1, in use, the proximal suction inlet 8p can be positioned proximal to the outflow ports 4p, 5p of the thoracic duct 4 and the subclavian vein 5, e.g., upstream thereof. The proximal suction inlet 8p may thus allow for regular fluid flow through the jugular vein 3 even when the proximal restrictor 2a is activated and occluding the jugular vein 3.

The catheter 1 can include a distal end Id configured to be implanted within the patient's body (e.g., within the jugular vein 3, as shown in this illustrated embodiment) and a proximal end 1p configured to not be implanted and instead be located outside the patient's body when the catheter's distal end Id is implanted. The distal end Id of the catheter 1 can be open so as to define a discharge opening of the catheter 1 that allows fluid in the lumen 7L to exit the catheter 1 therethrough. The distal restrictor 2b being positioned proximal to the discharge opening may help prevent back flow of fluid exiting the catheter 1 through the discharge opening. The distal restrictor 2b can thus be positioned just proximal to the discharge opening to help maximize backflow prevention. The catheter's proximal end 1p is configured to not be implanted and is shown outside of the patient's body in FIG. 1. FIG. 1 also shows a controller or motor 9 coupled to the catheter 1 and located outside of and proximal to the catheter's proximal end 1p so as to not be within the catheter's shaft 7 and to be located outside of the patient's body. Alternatively, as mentioned above, the catheter's proximal end 1p can be configured to be implanted, such as when the controller or motor 9 is included in the catheter's shaft 7.

The catheter 1 can include a pump configured to drive fluid flow through the catheter 1, e.g., through the lumen 7L thereof. The pump can have a variety of configurations. As in this illustrated embodiment, the pump can include an axial motor pump. The axial motor pump can generally be configured like an Archimedes' screw that drives fluid. The axial motor pump can include an impeller I and a drive shaft S (e.g., a cable or a rod) each located in the catheter's shaft 7, e.g., in the lumen 7L. Also as in this illustrated embodiment, the impeller I can be located fully distal to the proximal restrictor 2a and can be located at least partially proximal to the second restrictor 2b so as to be at least partially located within the low pressure zone and hence near the distal inlet opening. In this illustrated embodiment, the impeller I is fully located within the low pressure zone. The drive shaft S can extend longitudinally through the catheter 1, e.g., through the lumen 7L, to the controller or motor 9. The motor 9 can be configured to drive the drive shaft S, e.g., to rotate the drive shaft S, and hence drive the impeller I, e.g., rotate the impeller I. The drive shaft S can be a solid member, which may provide structural stability to the drive shaft S. Alternatively, the drive shaft S can be hollow, e.g., be cannulated. The drive shaft S being hollow can allow a guide wire to be advanced therethrough, which may facilitate delivery of the catheter 1 into a vein, as will be appreciated by a person skilled in the art, such as by allowing the guide wire to be introduced into a vein and the catheter 20 to then be advanced over the guide wire (and into a sheath (not shown) of the system 10 advanced over the guide wire prior to the catheter 20 being advanced over the guide wire, if the system 10 includes a sheath). For example, the guide wire can be introduced into the jugular vein 3 (e.g., a Seldinger technique via a central venous access under ultrasound guidance), and then the drive shaft S (and the catheter 1 coupled thereto) can be advanced over the guide wire into the jugular vein 3.

The pump can be configured to pump fluid at a variety of rates. In an exemplary embodiment, the pump can be configured to pump fluid at a rate in a range of about 100 to 1000 ml/hour, which can provide a pressure reduction in the low pressure zone from a pressure in a range of about 10 to 20 mmHg (the pressure in the higher pressure zones) to a pressure in a range of about 0 to 6 mmHg (e.g., in a range of about 2 to 4 mmHg, which is a typical normal level, or in a range of about 2 to 5 mmHg, which is also a typical normal level). In at least some embodiments, the pump can have a static, e.g., unchangeable, flow rate. The flow rate can thus be predictable and/or chosen for a specific patient. In other embodiments, the pump can have an adjustable flow rate. The flow rate being adjustable can help the pump accommodate changes in the patient's condition over time and/or allow the pump to be driven at a selected rate for a particular patient. The flow rate can be adjustable in a variety of ways, as will be appreciated by a person skilled in the art, such as by being wirelessly adjusted using a user-operated control device located external to the patient and configured to wirelessly communicate with the pump (e.g., with the controller 9) to adjust the flow rate thereof.

In at least some embodiments, the controller 9 can be configured to be in electronic communication with at least one pressure sensor (not shown). A person skilled in the art will appreciate that a variety of suitable sensors can be used for monitoring pressure, such as central venous pressure (CVP) or other fluid pressure sensors, and blood pressure sensors. The at least one pressure sensor can be implanted in the patient as part of the pump, implanted in the patient as a separate component from the pump, or the at least one pressure sensor can be located external to the patient, such as by being on a skin surface thereof. If not already a part of the pump so as to be in electronic communication therewith, the at least one pressure sensor can be configured to be in electronic communication with the pump over a communication line such as a wired line or a wireless line. In an exemplary embodiment, two pressure sensors can be implanted in the patient. One of the pressure sensors can be implanted between the first and second restrictors 2a, 2b so as to be in the low pressure zone, and the other one of the pressure sensors can be implanted in the vein either proximal to the proximal restrictor 2a (e.g., proximal to the proximal inlet) or distal to the distal restrictor 2b (e.g., distal to the discharge opening) so as to be in one of the higher pressure zones. The two sensors can thus allow a pressure differential to be determined between the low pressure zone and the higher pressure zone. In other embodiments, another number of pressure sensors can be implanted in the patient (e.g., one, three, four etc.) and/or the pressure sensor(s) can be implanted at other locations.

The catheter 1 can include at least one lumen (not shown) configured to facilitate use of the pressure sensor(s), for example to facilitate placement of the pressure sensor(s) and/or to be filled with a fluid such as saline to allow for external pressure measurement.

In addition to or instead of the one or more pressure sensors, the controller 9 can be configured to be in electronic communication with at least one other type of sensor (not shown) configured to sense a parameter other than pressure. Examples of sensors that can be used to measure a parameter other than pressure include radio frequency transmitters and receivers, fluid sensors, bio impedance sensors, heart rate sensors, breathing sensors, activity sensors, and optical sensors. Examples of the measured parameter include fluid amount (e.g., as measured by a fluid sensor, such as a fluid sensor placed in a lung to sense fluid amount in the lung), bio impedance (e.g., as measured by a bio impedance sensor), heart rate (e.g., as measured by a heart rate sensor), breathing rate (e.g., as measured by a breathing sensor), patient activity level (e.g., as measured by an activity sensor), and organ dimension (e.g., as measured by an optical sensor). The sensor can be implanted in the patient as part of the pump, implanted in the patient as a separate component from the pump (e.g., implanted in an interstitial space around a lung, implanted at a junction of a right subclavian vein of a patient and an internal jugular vein of the patient, implanted at a junction of a left subclavian vein of a patient and an internal jugular vein of the patient, etc.), or the sensor can be located external to the patient, such as by being on a skin surface thereof. If not already a part of the pump so as to be in electronic communication therewith, the non-pressure sensor(s) can be configured to be in electronic communication with the pump over a communication line such as a wired line or a wireless line. The non-pressure sensor(s) can include one or more sensors. In embodiments including a plurality of sensors, each of the sensors can be configured to measure the same parameter as or a different parameter than any one or more of the other sensors.

The motor 9 can be included as part of the pump and can be configured to be implanted in the patient with the pump, or, as in this illustrated embodiment, the motor 9 can be configured to be non-implantable. The motor 9 being non-implantable can help the pump have a smaller size and/or can allow the pump to be driven by a more powerful motor since the motor 9 can be larger than an implantable motor.

The controller 9 can be included as part of the pump and can be configured to be implanted in the patient with the pump, or, as in this illustrated embodiment, the controller 9 can be configured to be non-implantable. The controller 9 being part of the pump can help allow the pump to be a self-contained system, although in such a controller requires space in the pump, which can increase a size of the pump. The controller 9 being non-implantable can help the pump have a smaller size and/or can allow the pump to be controlled by a more powerful processor since the processor can be more easily upgraded than if implanted with the pump and/or since the processor's size can be less important when outside the pump as opposed to inside the pump.

The controller 9 can include any type of microprocessor or central processing unit (CPU), including programmable general-purpose or special-purpose microprocessors and/or any one of a variety of proprietary or commercially available single or multi-processor systems. The controller 9 can be a component of a control system that includes any number of additional components, such as a memory configured to can provide temporary storage and/or non-volatile storage; a bus system; a network interface configured to enable the control system to communicate with other devices, e.g., other control systems, over a network; and an input/output (UO) interface configured to connect the control system with other electronic equipment such as I/O devices (e.g., a keyboard, a mouse, a touchscreen, a monitor, etc.) configured to receive an input from a user.

The controller 9 can be configured to receive user input thereto to control any of a variety of aspects related to the catheter 1, such as speed of the motor 9 and ideal range of pressure for the low pressure zone.

In at least some embodiments, the pump can be configured to change its pumping rate (e.g., from zero to a non-zero value, from a non-zero value to zero, or from one non-zero value to another non-zero value) based on pressure measured by the at least one pressure sensor. The controller 9 can be configured to effect such change in response to the sensed pressure. If the measured pressure exceeds a predetermined threshold maximum pressure value, the pump can be configured to increase its pump rate (e.g., increase from zero or increase from some non-zero value) in an effort to decrease the pressure. For example, if the measured pressure within the low pressure zone is too high (e.g., is above a predetermined threshold), the pump can increase its pump rate to decrease the pressure within the low pressure zone. For another example, if the measured pressure within the low pressure zone is below a predetermined threshold, the pump can decrease its pump rate to maintain or increase the pressure within the low pressure zone. For yet another example, if a measured pressure differential between the low pressure zone and the higher pressure zone is not sufficiently great (e.g., is below a predetermined threshold), the pump can increase its pump rate to increase the pressure differential.

In at least some embodiments, the catheter 1 can include only one restrictor, the proximal restrictor 2a. A higher pressure zone can thus be proximal to the proximal restrictor, and a low pressure zone can be distal to the proximal restrictor. The proximal restrictor 2a positioned proximal to (e.g., upstream) of the outflow port 4p of the thoracic duct 4 being the only restrictor of the catheter 1, instead of the distal restrictor 2b positioned distal to (e.g., downstream) of the outflow port 4p of the thoracic duct 4, may help prevent back flow from the subclavian vein 5 while providing the low pressure zone and benefit(s) thereof.

In at least some embodiments, the catheter 1 can have a soft atraumatic tip at its distal end Id that is tapered in a distal direction and that is flexible. The soft atraumatic tip may facilitate smooth, safe introduction of the catheter 1 into the vein 3. Exemplary materials from which the atraumatic tip can be made include polyurethanes. The catheter may additionally include a flexible extension similar to a guide wire tip and/or have a hydrophilic coating, each of which may further facilitate smooth, safe introduction of the catheter 1 into the vein 3.

In at least some embodiments, the proximal restrictor 2a can be configured to only partially occlude the vein 3 in which the catheter 1 is positioned when the proximal restrictor 2a in its activated configuration. This partial occlusion may facilitate normal fluid flow through the vein 3 even when the proximal restrictor 2a is in the activated configuration. In embodiments in which the proximal restrictor 2a is configured to only partially occlude the vein 3 when in its activated configuration, the catheter 1 can, but need not, include the proximal inlet 8p to facilitate fluid flow through the vein 3. The partial occlusion can be achieved in a variety of ways. For example, the proximal restrictor 2a can have at least one lumen or hole formed therethrough configured to allow fluid flow therethrough when the proximal restrictor 2a is in the activated configuration. For another example, a maximum diameter of the proximal restrictor 2a in the activated configuration can be less than a maximum internal diameter of the vein 3 in which the catheter 1 is positioned to allow fluid flow around an exterior of the proximal restrictor 2a.

In at least some embodiments, the catheter 1 can include at least one lumen or tube (not shown) configured to pass blood therethrough outside the patient's body and back into the patient. Such functionality may allow for the monitoring of blood volume and performing hemofiltration.

In at least some embodiments, the catheter 1 can include one or more radiopaque markers (not shown) configured to be visible using an imaging technique such as fluoroscopy. The one or more radiopaque markers can be on the catheter's shaft 7 at or near one or more features along the shaft 7, such as any or all of the inlet openings or any or all of the restrictors 2a, 2b. The one or more radiopaque markers may thus facilitate proper positioning of the shaft 7 and/or features thereon within a vein. For example, prior to activation of the catheter's restrictor(s) 2a, 2b, the position of the restrictor(s) 2a, 2b within the vein 3 can be verified by visualizing the one or more radiopaque markers using an imaging system.

The first and second restrictors 2a, 2b are discussed with respect to FIG. 1 above as being balloons configured to inflate and deflate, but the first and second restrictors 2a, 2b can have other configurations. For example, the first and second restrictors 2a, 2b can each include a stent configured to expand (corresponding to an activated configuration) and constrict (corresponding to a relaxed configuration). The expandable/constrictable stents can have a variety of configurations, as will be appreciated by a person skilled in the art.

Figure 2:
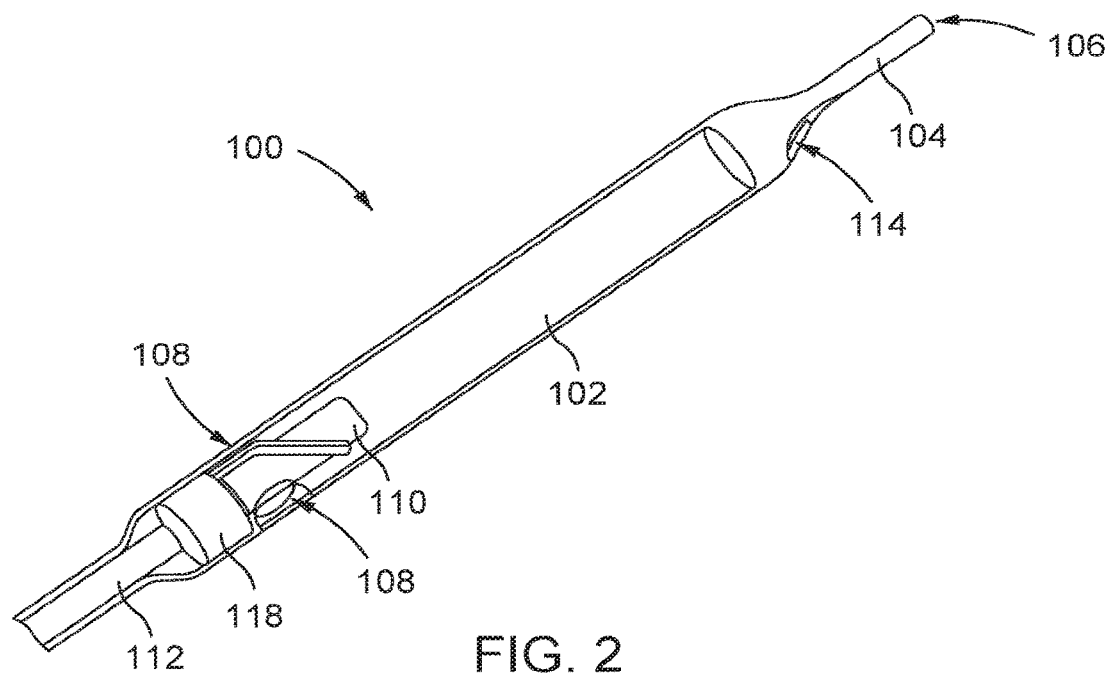
FIG. 2 is a perspective, partially transparent view of a distal portion of another embodiment of a catheter.
Figure 3:
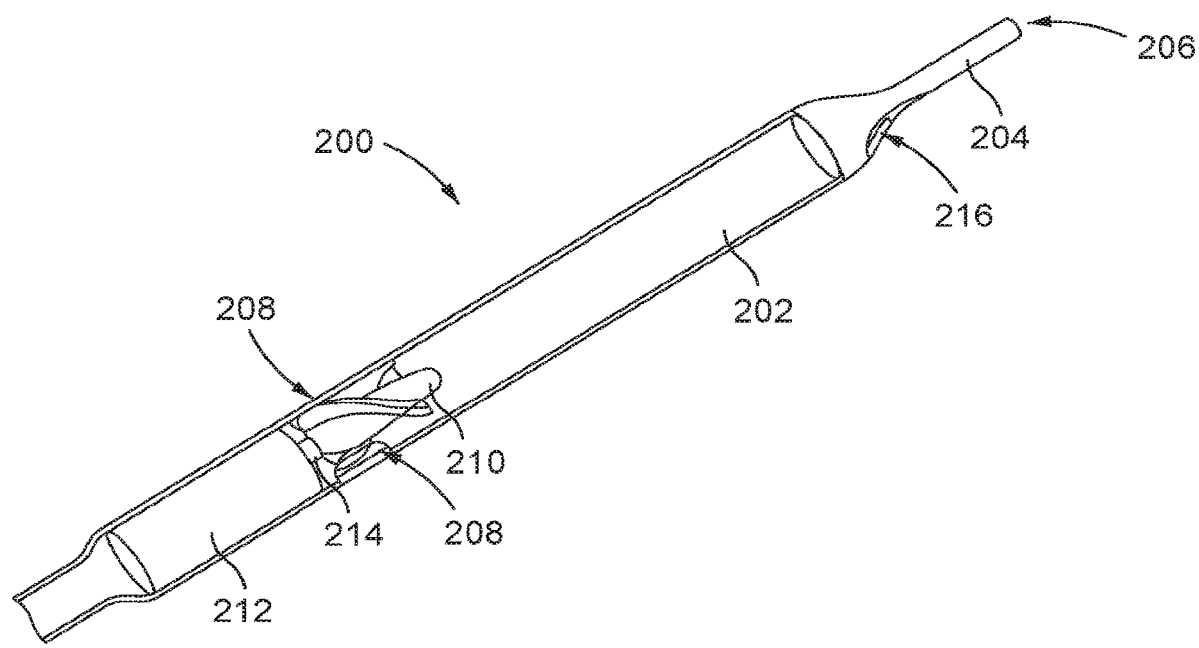
FIG. 3 is a perspective, partially transparent view of a distal portion of yet another embodiment of a catheter.
Figure 4:
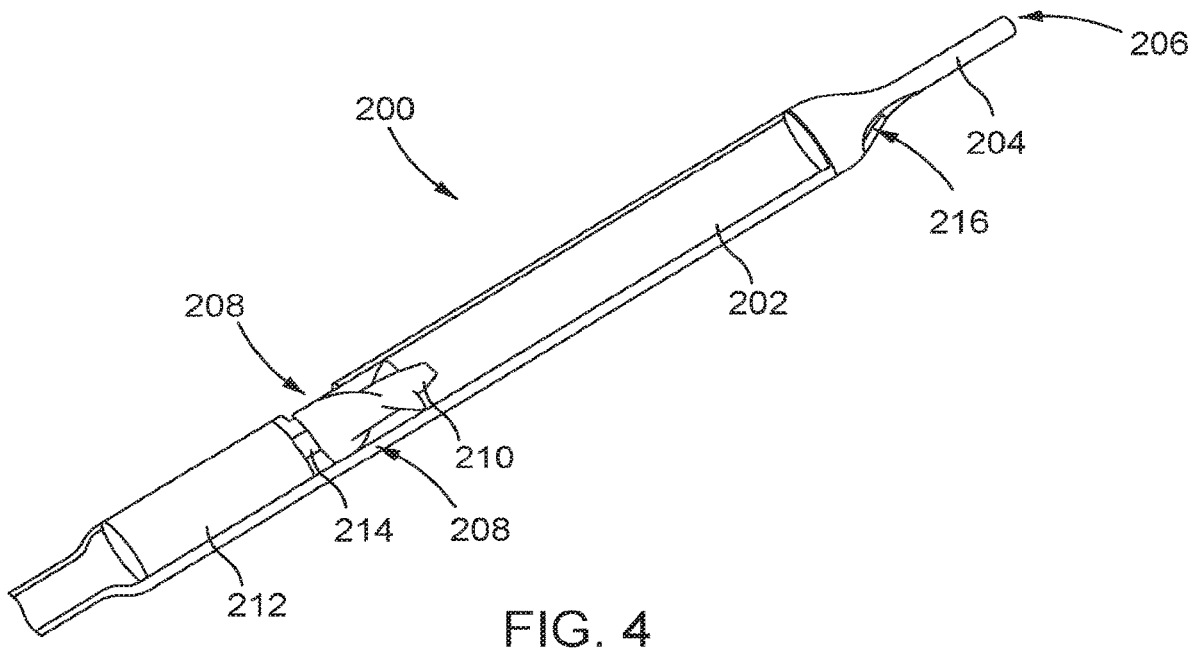
FIG. 4 is a partial cross-sectional view of the distal portion of the catheter of FIG. 3.
Figure 5:
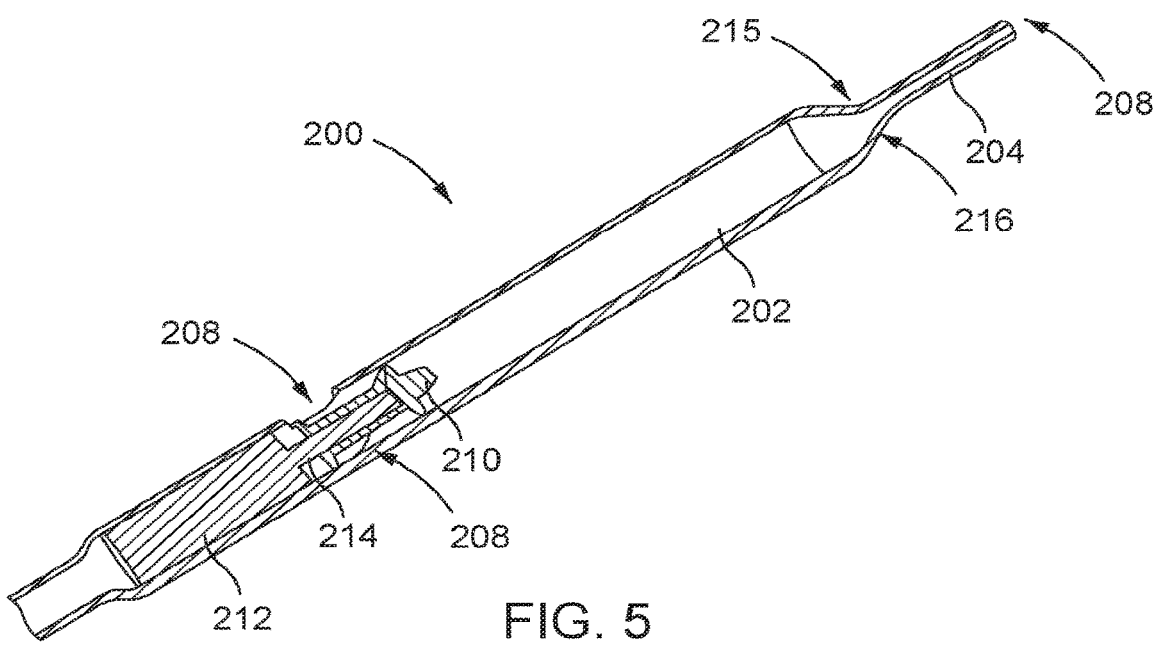
FIG. 5 is a cross-sectional view of the distal portion of the catheter of FIG. 3.
Figure 6:
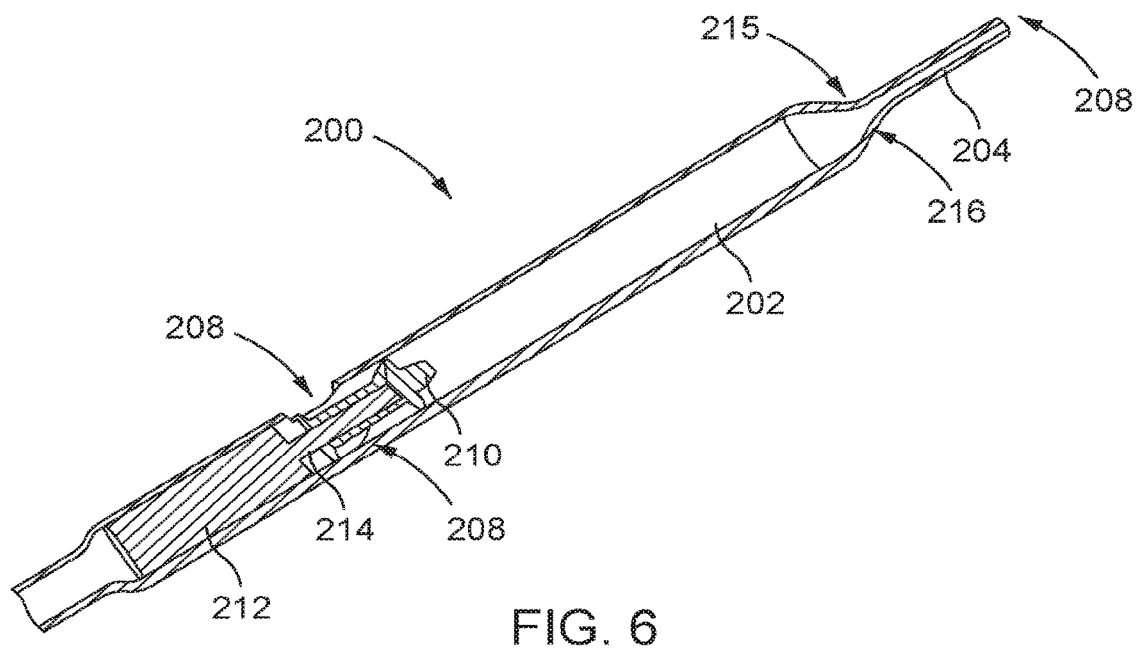
FIG. 6 is a schematic version of the cross-sectional view of FIG. 5.

FIG. 2 illustrates another embodiment of a catheter 100 that includes at least one restrictor (not shown in FIG. 2 for clarity of illustration). The catheter 100 of FIG. 2 can generally be configured and used similar to that discussed above regarding the catheter 1 of FIG. 1, e.g., include a shaft 102, a soft, distally-tapering atraumatic tip 104, a discharge opening 106, a proximal inlet opening 108, an impeller 110, a drive shaft 112 extending proximally to a motor (not shown), and a distal inlet opening 114. The motor in this illustrated embodiment is external, similar to the embodiment discussed above regarding the catheter 1 of FIG. 1. The proximal inlet opening 108 in this illustrated embodiment is in the form of two opposed ovular openings formed through a sidewall of the shaft 102. The distal inlet opening 114 in this illustrated embodiment is in the form of two opposed ovular openings formed through a sidewall of the atraumatic tip 104 distal to the shaft 102 (one of the openings is obscured in FIG. 2). The catheter 100 can include a bearing 116 just proximal to the impeller 110, which may help stabilize the impeller 110 within the shaft 102.

FIG. 3 through FIG. 6 illustrate another embodiment of a catheter 200 that includes at least one restrictor (not shown in FIG. 3 through FIG. 6 for clarity of illustration). The catheter 200 of FIG. 3 through FIG. 6 can generally be configured and used similar to that discussed above regarding the catheter 1 of FIG. 1, e.g., include a shaft 202, a soft, distally-tapering atraumatic tip 204, a discharge opening 206, a proximal inlet opening 208, an impeller 210, a motor 212, a drive shaft 214 extending between the impeller 210 and the motor 212, and a distal inlet opening 216. The motor 212 in this illustrated embodiment is an on-board motor configured to be implanted with the catheter 200. Similar to the catheter 100 of FIG. 2, the proximal inlet opening 208 in this illustrated embodiment is in the form of two opposed ovular openings formed through a sidewall of the shaft 202, and the distal inlet opening 216 in this illustrated embodiment is in the form of two opposed ovular openings formed through a sidewall of the atraumatic tip 204 distal to the shaft 202 (one of the openings is obscured in FIG. 3 and FIG. 4).

Figure 7:
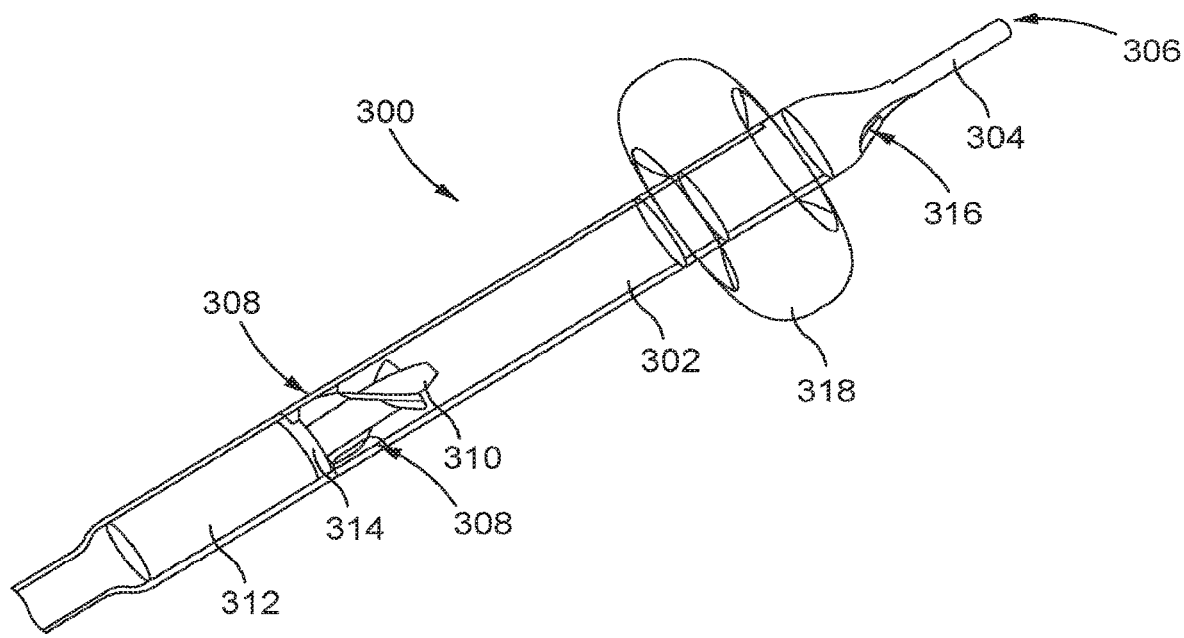
FIG. 7 is a perspective, partially transparent view of a distal portion of yet another embodiment of a catheter.
Figure 8:
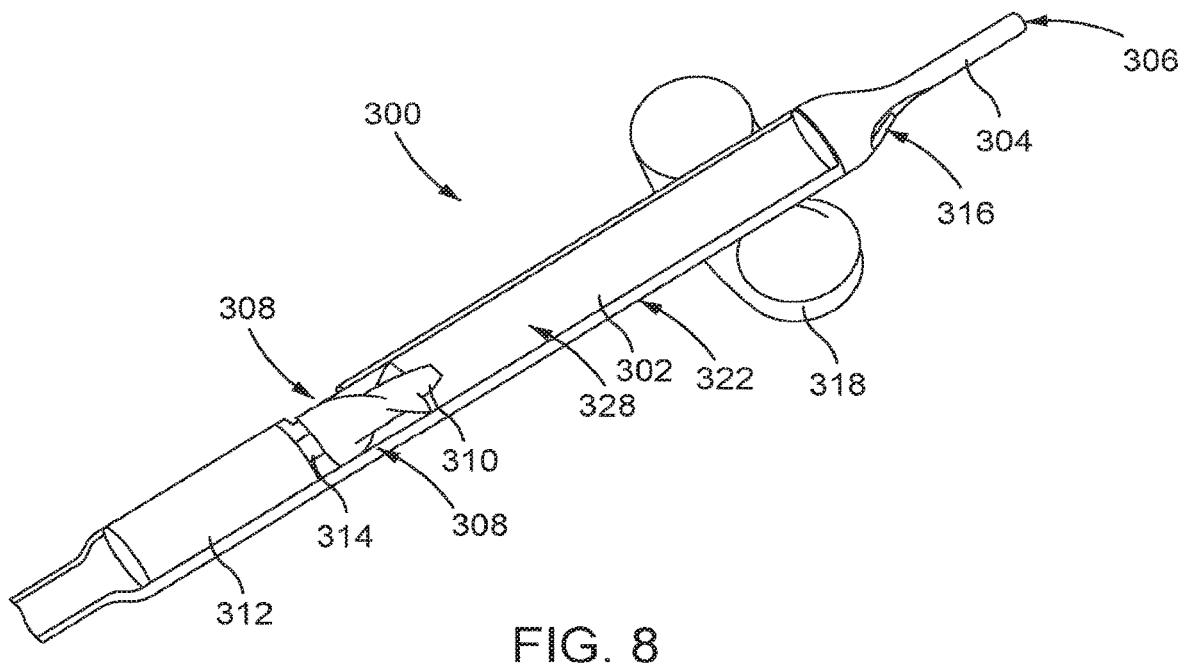
FIG. 8 is a partial cross-sectional view of the distal portion of the catheter of FIG. 7.
Figure 9:
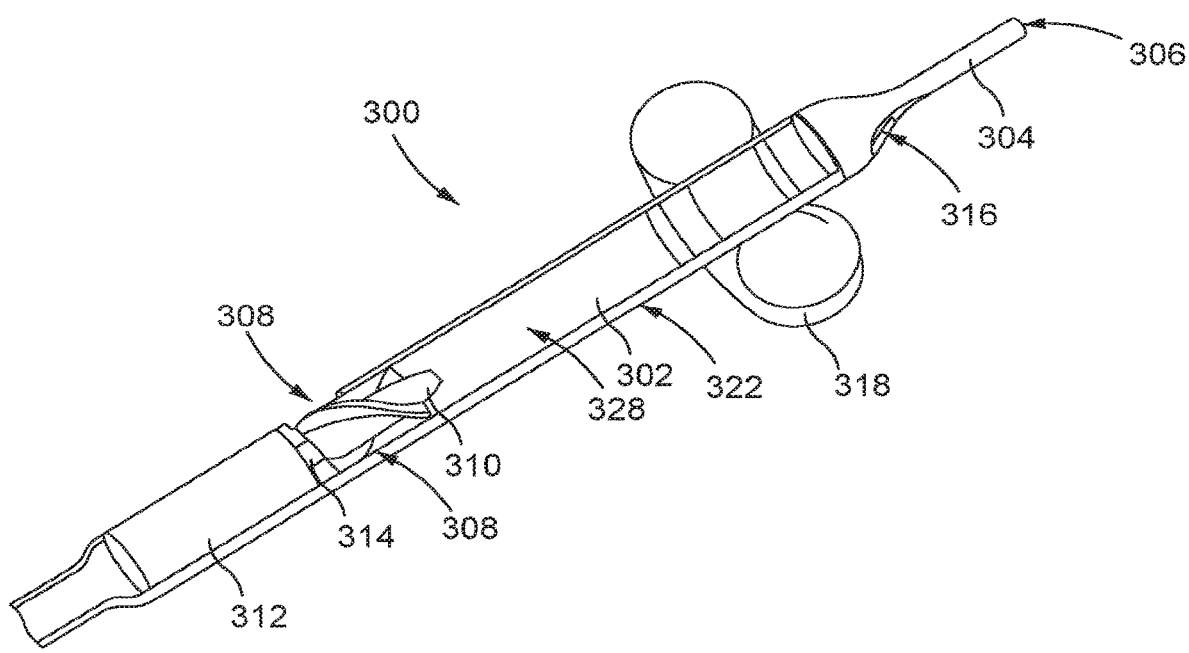
FIG. 9 is a schematic version of the cross-sectional view of FIG. 8.

FIG. 7 through FIG. 9 illustrate another embodiment of a catheter 300 that includes at least one restrictor 318, which in this illustrated embodiment includes only one restrictor 318 that is located distal to an impeller 310. The catheter 300 of FIG. 7 through FIG. 9 can generally be configured and used similar to that discussed above regarding the catheter 200 of FIG. 3 through FIG. 6, e.g., include a shaft 302, a soft, distally-tapering atraumatic tip 304, a discharge opening 306, a proximal inlet opening 308, the impeller 310, an on-board motor 312, a drive shaft 314 extending between the impeller 310 and the motor 312, and a distal inlet opening 316. The shaft 302 includes multiple lumens extending therethrough, including a central lumen 320 for the impeller 310 and the motor 312 and an inflation lumen 322 for inflation/deflation of the restrictor 318, which in this illustrated embodiment includes a balloon. FIG. 7 through FIG. 9 show the restrictor 318 in an activated configuration, which in this illustrated embodiment is an inflated configuration.

In at least some embodiments, a catheter including restrictors can include a flexible membrane to which the restrictors are appended and which enables fluid (e.g., blood flow) to bypass a low pressure zone defined between the restrictors.

Figure 10:
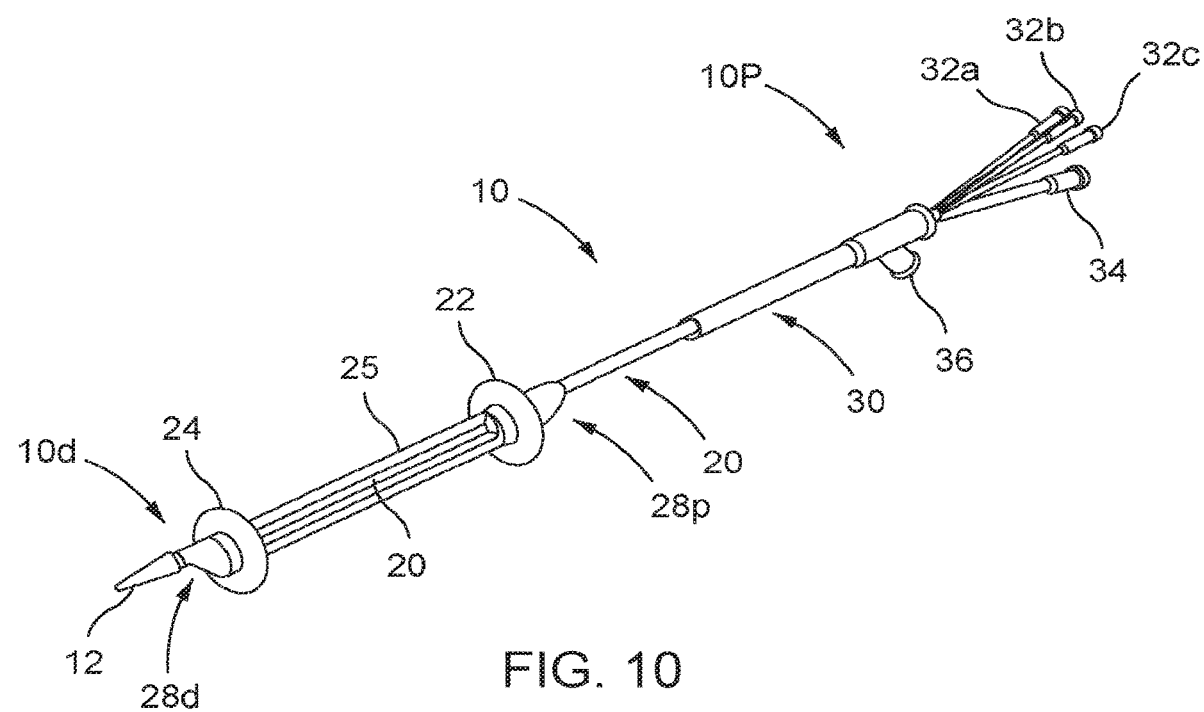
FIG. 10 is a perspective view of one embodiment of a catheter system.

FIG. 10 illustrates one embodiment of an indwelling catheter system 10 that can include a flexible membrane 28 and at least one restrictor 22, 24, which are in the form of balloons in this illustrated embodiment. As illustrated, the indwelling catheter system 10 includes an introducer sheath 30 used to deploy a catheter 20 having a generally elongate tubular shape, with a circular or ovular cross-sectional geometry. The indwelling catheter system 10 can include proximal end 10p, which can be configured to be placed outside of a patient's body, and distal end 10d, which can be configured for placement within a patient's vein.

The catheter 20 can have a single suction lumen 48 (see FIG. 24 and FIG. 25) for communicating fluid out of the vein to an external pump, the flexible membrane 28 (which is tubular in this illustrated embodiment), and first and second restrictors 22, 24, which are attached to the membrane 28 and surround the membrane 28 and catheter 20. The flexible membrane 28 can be assembled to the catheter 20 (e.g., to the shaft thereof) in any of a number of ways to enable the flexible membrane 28 to form an ovoid or a kidney shape upon expansion of the flexible membrane 28 (as a result of activating the restrictors 22, 24) so that fluid can be transported from a position within the vein proximal to the first restrictor 22, through the low pressure zone within the vein, and to discharge the fluid at a point distal to the second restrictor 24. The flexible membrane 28 can be attached, e.g., bonded or welded, around a partial portion (such as a non-zero portion that is less than 360° of the catheter shaft's circumference 50) or full portion (360° around the catheter shaft's circumference 50) of the circumference 50 of the catheter's shaft, such as in a range of about 10° to 360° of the shaft's circumference 50.

Figure 11:
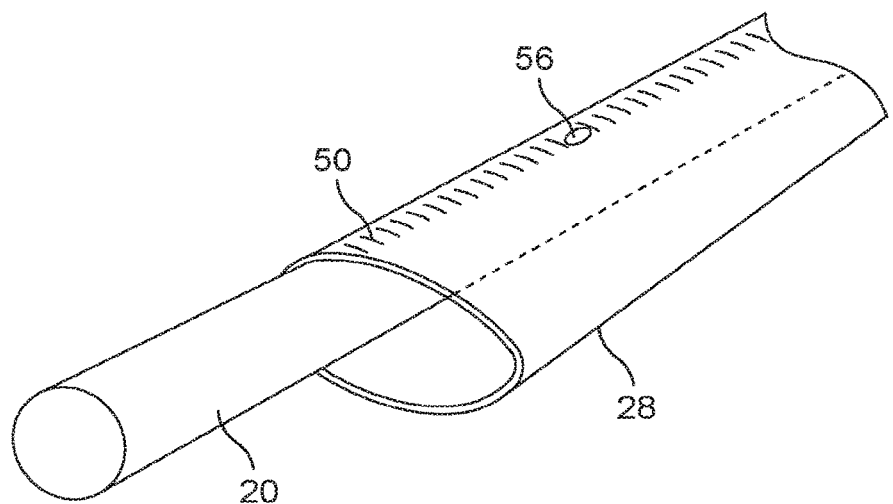
FIG. 11 is perspective view of a flexible membrane and catheter shaft of the catheter system of FIG. 10.
Figure 12:
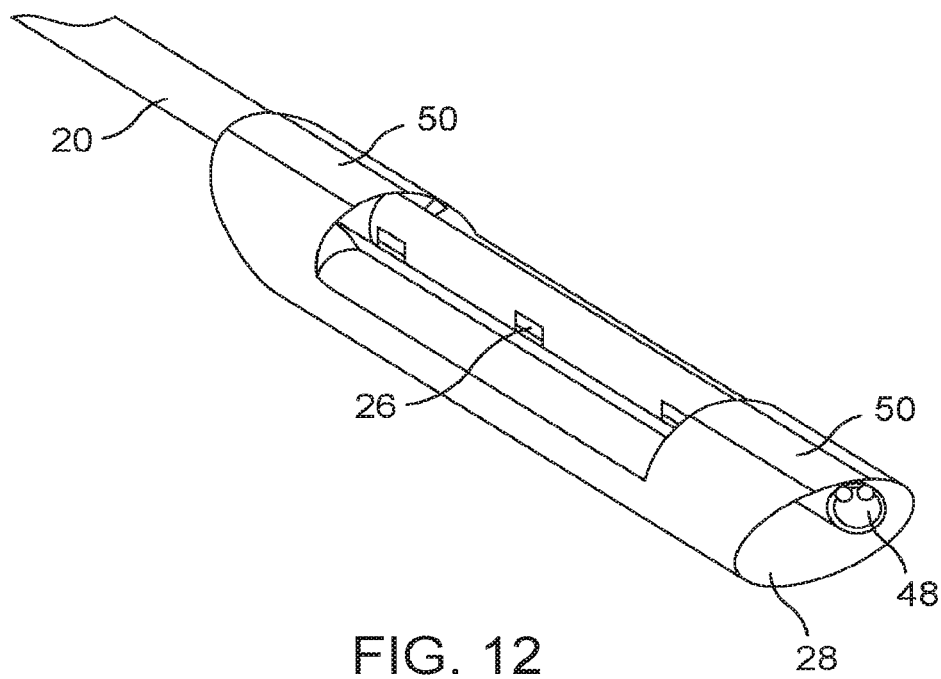
FIG. 12 is another perspective view of the flexible membrane and catheter shaft of the catheter system of FIG. 11.

FIG. 11 and FIG. 12 illustrate the flexible membrane 28 attached to a partial portion around the catheter shaft circumference 50. At least one inflation port 56 is in fluid communication with an inflation lumen (control lumen 42 discussed further below) for inflating the first restrictor 22 and is disposed on a surface of the flexible membrane 28 and will be underneath the first restrictor 22 attached thereto, as discussed below. A second inflation port (not shown) is in fluid communication with at least one inflation lumen (control lumen 44 discussed further below) for inflating the second restrictor 24 and is disposed on a surface of the flexible membrane 28 and will be underneath the second restrictor 22 attached thereto, as discussed below. As shown in FIG. 12, which has a portion of the flexible membrane 28 removed for clarity of illustration, at least one suction port 26 is extending through an external surface of the catheter 20 such that it is in fluid communication with a suction lumen 48.

Figure 13:
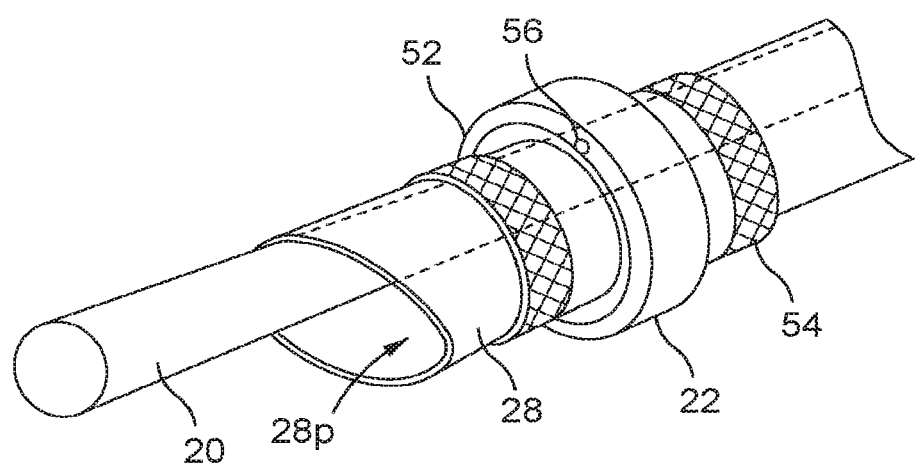
FIG. 13 is a perspective view of a restrictor of the catheter system of FIG. 10 attached to the flexible membrane of the catheter system.
Figure 14:
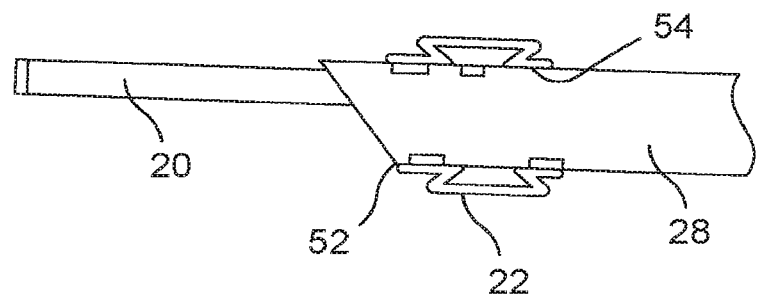
FIG. 14 is side, partial cross-sectional view of flattened edges of the restrictor of FIG. 11.
Figure 15:
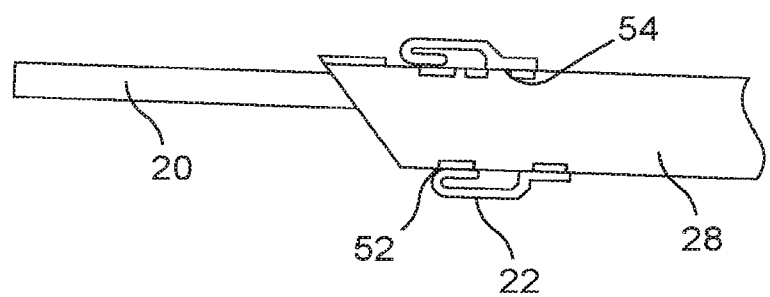
FIG. 15 is a side, partial cross-sectional view of folded edges of another embodiment of a restrictor.

Following attachment of the flexible membrane 28 to the catheter 20, the restrictors 22, 24 can be attached to the catheter 20. As shown in FIG. 13, the first restrictor 22 can be bonded or welded to an outer surface of the flexible membrane 28 over the inflation port 56 so that the first restrictor 22 surrounds the outer circumference 52, 54, of the catheter 20 and the flexible membrane 28. As shown in FIG. 14, edges of the first restrictor 22 can be flattened to extend beyond the collapsed balloon and bonded to the flexible membrane 28. The second restrictor 24 can be attached to the catheter 20 similar to the first restrictor's attachment to the catheter 20. In an alternate embodiment, as shown in FIG. 15, a restrictor 22' has at least one edge 52' thereof folded under and bonded beneath the collapsible tube of the restrictor 22'. One or both of the first and second restrictors 22, 24 can be attached to the catheter 20 similar to the attachment of the restrictor 22' of FIG. 15.

Figure 16:
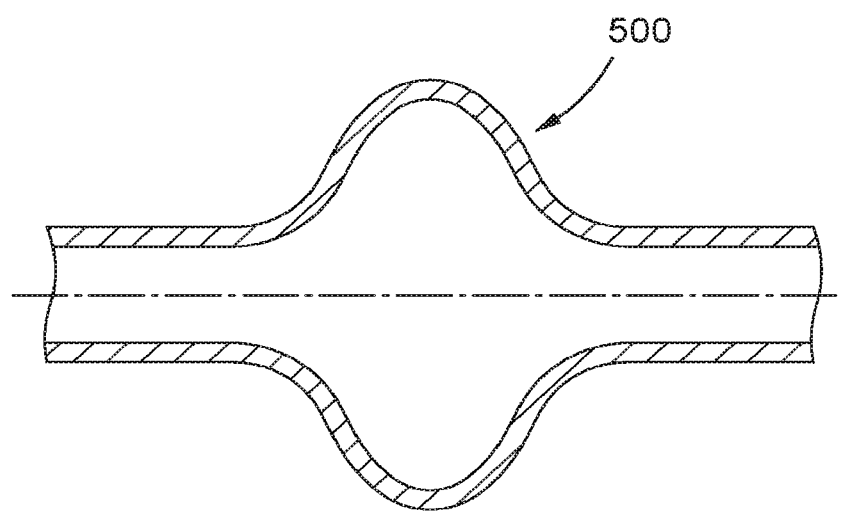
FIG. 16 is a cross-sectional schematic view of a pattern for forming a restriction member with a torus shape.
Figure 17:
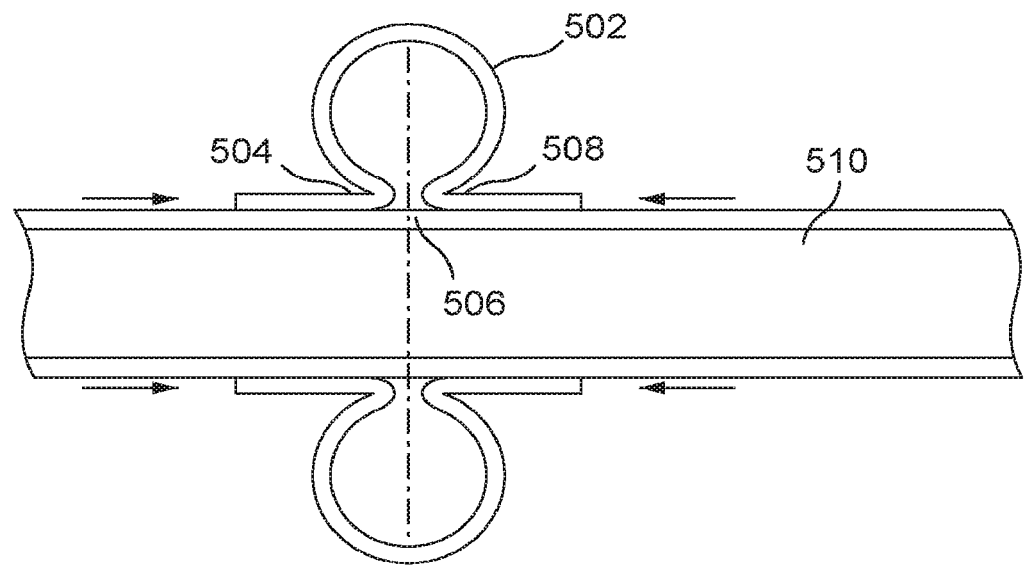
FIG. 17 is cross-sectional schematic view of a restriction member formed using the pattern of FIG. 16 and of a sleeve on which the restriction member is assembled.
Figure 18:
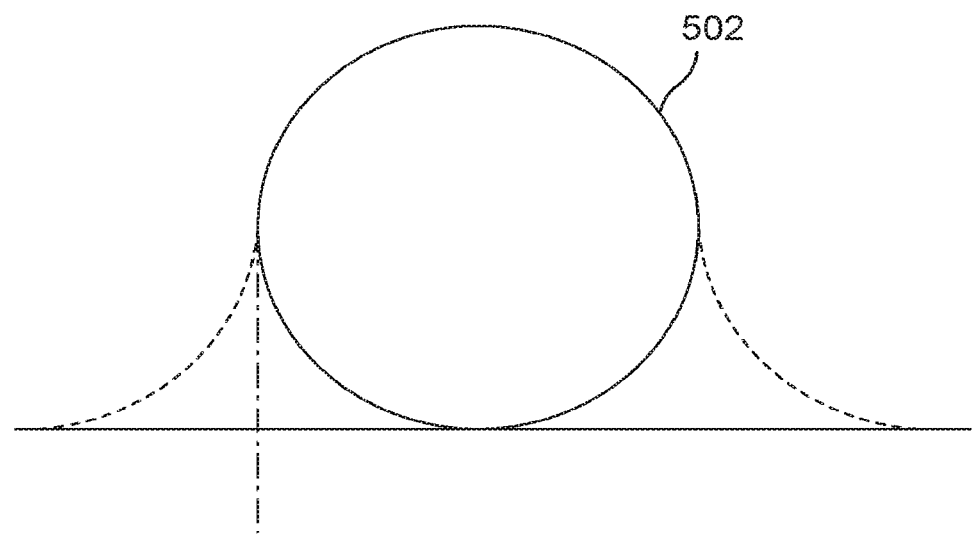
FIG. 18 is a cross-sectional schematic view of the restriction member of FIG. 17 following inversion of legs thereof.
Figure 19:
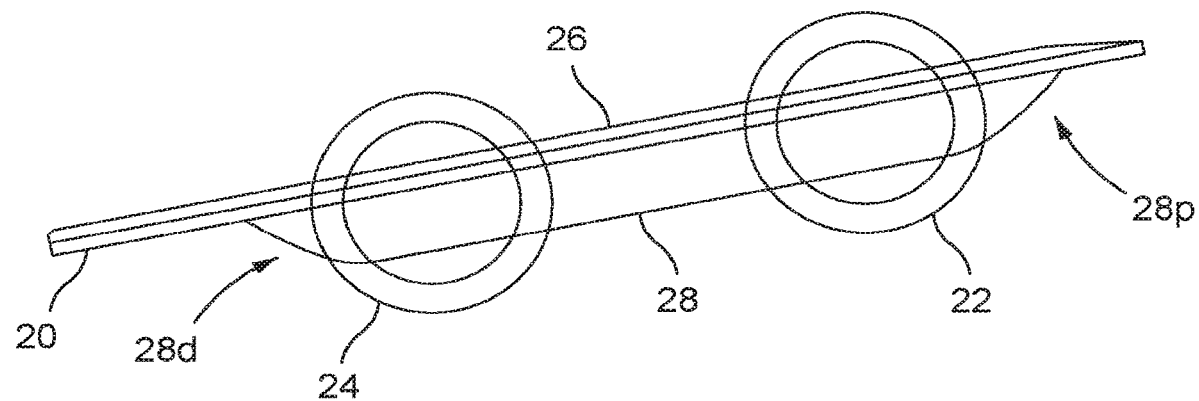
FIG. 19 is a perspective view of a distal portion of the catheter system of FIG. 10.

FIG. 15 through FIG. 18 illustrate one embodiment of a method for manufacturing a torus-shaped restriction member 502 configured to be attached to a catheter shaft as discussed herein. As shown in FIG. 16, a pattern 500 is formed by a process such as blow molding or dip molding. For example, a slope of the mold pattern can be formed in a continuous shape without sharp corners or directional reversion. As shown in FIG. 17, after the restriction member 502 is formed using the pattern 500, it is assembled onto a collapsible sleeve 510. During the assembly, two legs 504, 506 of the restriction member 502 are pushed towards each other and bonded together. The restriction member 502 maintains an opening 508 between the legs 504, 506 to enable the formation or positioning of an inflation port in the catheter that will be used to inflate the restriction member 502. As shown in FIG. 18, after the legs 504, 506 are brought together, as explained above, a lower section of the restriction member 502 is inverted inward. The curvature of the restriction member 502 is maintained in the opposite direction thereby maintaining material continuity to form the restriction member 502, as illustrated.

The suction lumen 48 can accommodate the flow of fluid from the vein in which the catheter 20 is implanted to a pump external to the patient, when deployed, and the membrane 28 can enable fluid returned from the pump to bypass the portion of the vein occluded by the restrictors 22, 24. As shown in FIG. 19, FIG. 20, FIG. 24, and FIG. 25, the suction lumen 48 can communicate with the suction port 26, formed in an outer wall of catheter 20, and can extend to a proximal end of the catheter 20. The proximal end of the catheter 20 can include a hub 34 which communicates with discharge tubing (not shown) coupled to the pump external to the patient (not shown) to communicate fluid withdrawn from within the low pressure zone between the restrictors 22, 24 through the suction lumen 48 of the catheter 20. Fluid present in the vein in which the catheter 20 is implanted, and between the deployed restrictors 22, 24 of the catheter 20, is drawn from the vein into the suction port 26 and into the suction lumen 48 of catheter 20 so that it can be communicated to the external pump (not shown) via the suction lumen 48 and the discharge tubing.

The tubing extending out of the pump (not shown) to return fluid to the catheter system 10 can be coupled to the sheath 30 at a discharge port 36 (see FIG. 10, FIG. 21, FIG. 22, and FIG. 23). Fluid returned from the pump will enter the discharge port 36 and be discharged within the vein external to the catheter 20. The pump can facilitate fluid movement from the catheter 20 through the suction lumen 48 and into the discharge tubing through which it is communicated to the pump. The discharge port 36 can be configured to connect to an end of the drainage tubing having its other end in fluid communication with the pump. The discharge port 36 can, as shown, include surface features formed thereon and extending around to facilitate its connection to the discharge tubing.

As shown in FIG. 10, FIG. 11, FIG. 19, and FIG. 20, the first restrictor 22 can be downstream of (e.g., distal to) a proximal opening 28p of the membrane 28, and a distal opening 28d of the membrane 28 can be downstream of second restrictor 24. Thus, when the first and second restrictors 22, 24 are activated or deployed to fully occlude the vein, the lumen of the membrane 28 can provide a bypass route for fluid (e.g., blood) returning from the external pump or otherwise flowing downstream within the vein external to catheter 20. In other words, even though the vein is occluded by the restrictors 22, 24, blood and other fluid can flow through the lumen of the membrane 28 to flow from a position upstream of (e.g., proximal to) the proximal restrictor 22 to a position downstream of the distal restrictor 24. Although the catheter 20 and the flexible membrane 28 are illustrated to be oriented in a side-by-side relationship with respect to one another, they can be oriented in any other suitable manner, including having one member disposed within the other member. Also, the catheter 20 can have any number of additional lumens, which can function, for example, as control lumens to facilitate activation of the restrictors 22, 24 and/or to sense pressure at various locations within the vein in which the catheter 20 is disposed.

The catheter 20 can include a distal atraumatic tip 12 that can facilitate placement of the catheter 20 into the vein of a patient. The distal atraumatic tip 12 can have an aperture such that the tip 12 has a lumen extending therethrough. The lumen of the tip 12 can be configured to allow passage of a guide wire through the tip 12. The catheter 20, including the flexible membrane 28 and the restrictors 22, 24, can be advanced over the guide wire to be deployed from the sheath 30. The lumen and the aperture can be sized to accommodate a standard guide wire of size such as about 0.014", about 0.018", about 0.035", or about 0.038". In addition to or instead of the catheter 20 including the distal atraumatic tip 12, the sheath 30 can include a distal atraumatic tip to facilitate advancement of the sheath 30 having the catheter 20 disposed therein to a location where the catheter 20 is to be released from (e.g., advanced distally out of) the sheath 30. The sheath's distal atraumatic tip can include a lumen to allow passage of a guide wire through the tip, as discussed above.

Figure 20:
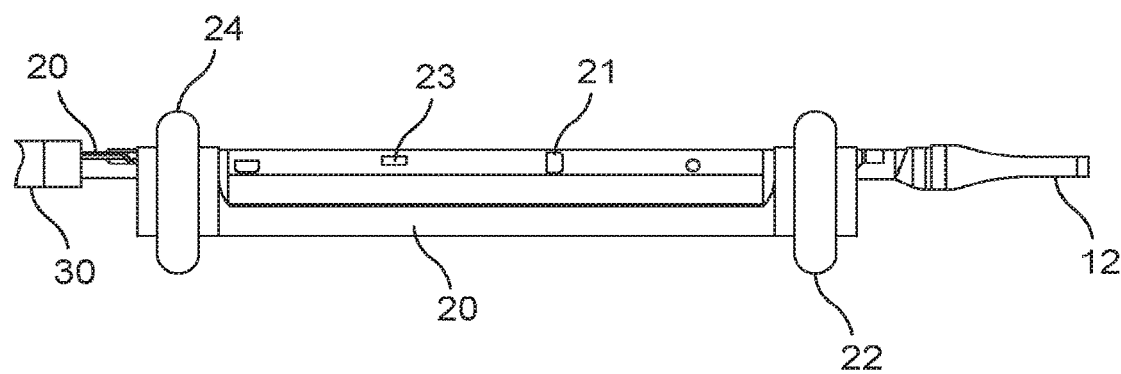
FIG. 20 is a side view of another distal portion of the catheter system of FIG. 10.
Figure 21:
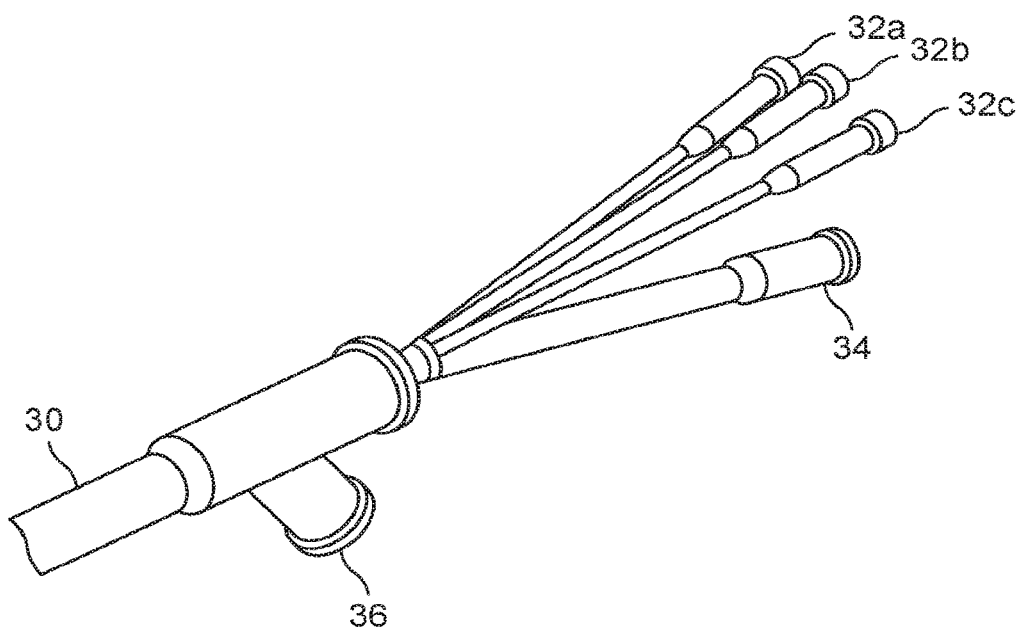
FIG. 21 is a perspective view of a proximal portion of the catheter system of FIG. 10.

FIG. 20 shows the catheter 20 can include one or more radiopaque markers 21 configured to be visible using an imaging technique such as fluoroscopy. As also shown in FIG. 20, the catheter 20 can include one or more sensors 23, which in this illustrated embodiment includes an optic pressure transducer, located between the restrictors 22, 24 and hence within a low pressure zone created between. The pressure transducer 23 is configured to continually monitor pressure within the low-pressure zone so pump function can be adjusted if necessary to keep the pressure at a desired level (in a desired range of about 2 to 5 mmHg, etc.) and at the location of the discharge lumen so internal jugular vein pressure can be monitored. The pressure transducer 23 is also configured to provide CVP measurements when the restrictors 22, 24 are deflated.

Figure 22:
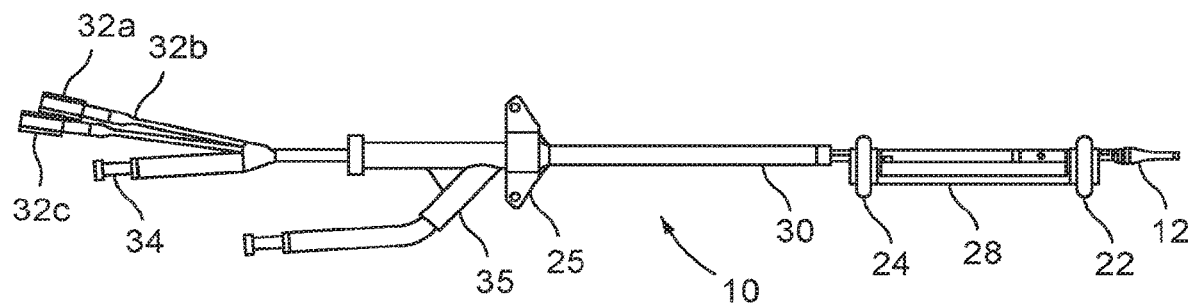
FIG. 22 is a side view of the catheter system of FIG. 10.

As shown in FIG. 22, the catheter system 10 can include an eyelet 25 configured to facilitate securement of the system 10 to a patient during use. For example, the eyelet 25 can be secured by a suture to the patient's skin. The catheter shaft can be locked in position relative to the sheath 30 using, for example, a Tuohy Borst valve, such that the catheter 20 can be secured to the patient during use via the sheath 30. The eyelet 25 may thus be secured to the patient after the catheter 20 has been advanced through the sheath 30 to be in a desired position within the patient to help ensure that the system 10 is secured to the patient with the catheter 20 in its desired position.

Figure 23:
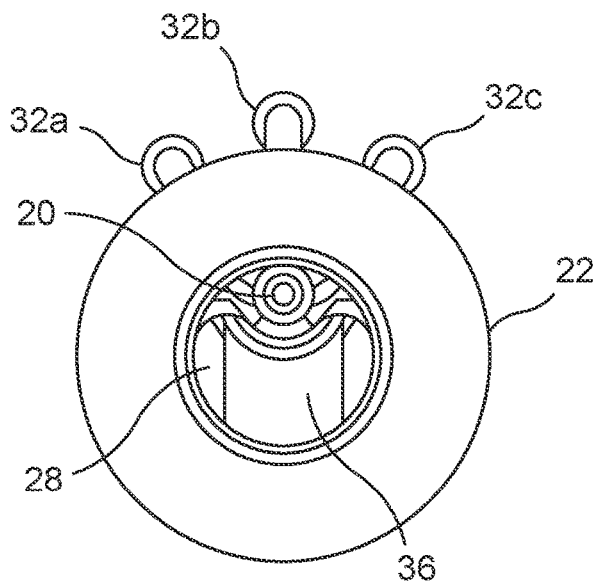
FIG. 23 is a distal end view of the catheter system of FIG. 10.
Figure 25:
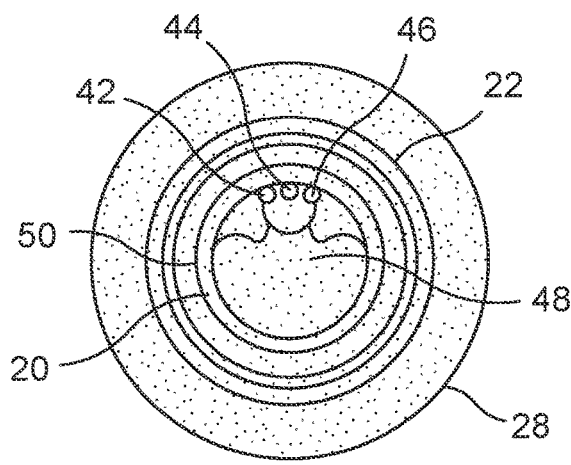
FIG. 25 is a cross sectional view of the catheter system of FIG. 10 having a restrictor thereof in an activated configuration.
Figure 24:
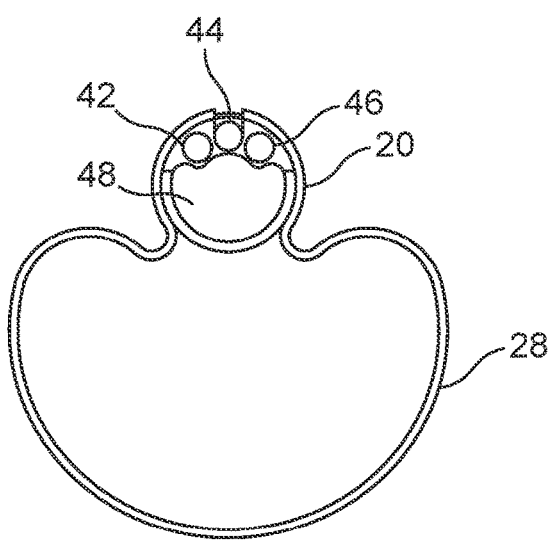
FIG. 24 is a cross sectional view of the catheter system of FIG. 10 with a flexible membrane of the catheter system in an expanded configuration.
Figure 26:
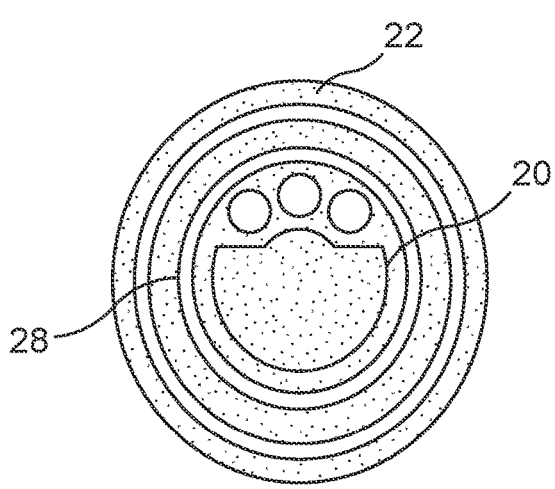
FIG. 26 is a cross sectional view of the catheter system of FIG. 10 having a restrictor thereof in a relaxed configuration.

As shown in FIG. 10, FIG. 12, and FIG. 23, the sheath 30 can include a plurality of ports 32a, 32b, 32c in fluid communication with respective ones of a plurality of control lumens 42, 44, 46 within the catheter 20. As shown in FIG. 24 through FIG. 26, the first and second ports 32a, 32b respectively communicate with the first and second control lumens 42, 44, which can be configured to deliver fluid to the first and the second restrictors 22, 24, respectively, to control the activation and deactivation of the restrictors 22, 24. The third port 32c can communicate with the third control lumen 46, which can communicate with an opening in the catheter 20 for purposes of sensing a pressure within the vein, as discussed above. The third control lumen 36 includes one or more pressure sensors in this illustrated embodiment, but any one or more of the control lumens 42, 44, 46 can include one or more pressure sensors, to be used for sensing pressure at various locations along the vein in which the catheter 20 is implanted, such as between the proximal and distal restrictors 22, 24 and upstream of the proximal restrictor 22.

FIG. 25 shows the suction lumen 48 is internal to the catheter 20 and the flexible membrane 28 that is external to the catheter 20 and is oriented in a side-by-side arrangement with respect to the catheter 20. The control lumens 42, 44, 46 can be disposed within the catheter 20, such as within the wall of the catheter 20, as shown. As indicated above, the cross-sectional arrangement of catheter 20 can take various forms, and the relative positioning of the suction lumen 48 and the control lumens 42, 44, 46 can vary. More or fewer suction lumens 48 and control lumens 42, 44, 46 can be provided in the catheter 20. For example, one or more additional control lumens can accommodate a variety of non-pressure sensors, as discussed above.

Sizes of the catheter 20, the sheath 30, and the flexible membrane 28 can vary depending upon the catheter system's intended uses. Generally, the catheter 20 can have a length in the range of about 25 to 40 cm. In addition, the diameter can also vary, but suitable catheters will typically be in the range of about 8 to 18 Fr. Other catheters described herein can have a similar size, e.g., a length in the range of about 25 to 40 cm and a diameter in the range of about 8 to 18 Fr. The sheath 30 can have a length in the range of about 10 to 25 cm, can have an internal diameter in the range of about 2.5 to 5.5 mm, and can have an external diameter in the range of about 3 to 6 mm. In one embodiment, the catheter 20 can have a diameter of about 8 Fr and the sheath 30 can have a diameter of about 11 Fr. The flexible membrane 28 can have a length in the range of about 50 to 150 mm. A distance between the distal end of the sheath 30 and the proximal end of the flexible membrane 28 can be up to about 100 mm. The diameter of the control lumens 42, 44, 46 can vary depending upon the requirements of a given application. The suction lumen 48 can have a diameter in the range of about 1 to 4 mm, while pressure inflation lumens can have a diameter in the range of about 0.1 to 1 mm.

Figure 27:
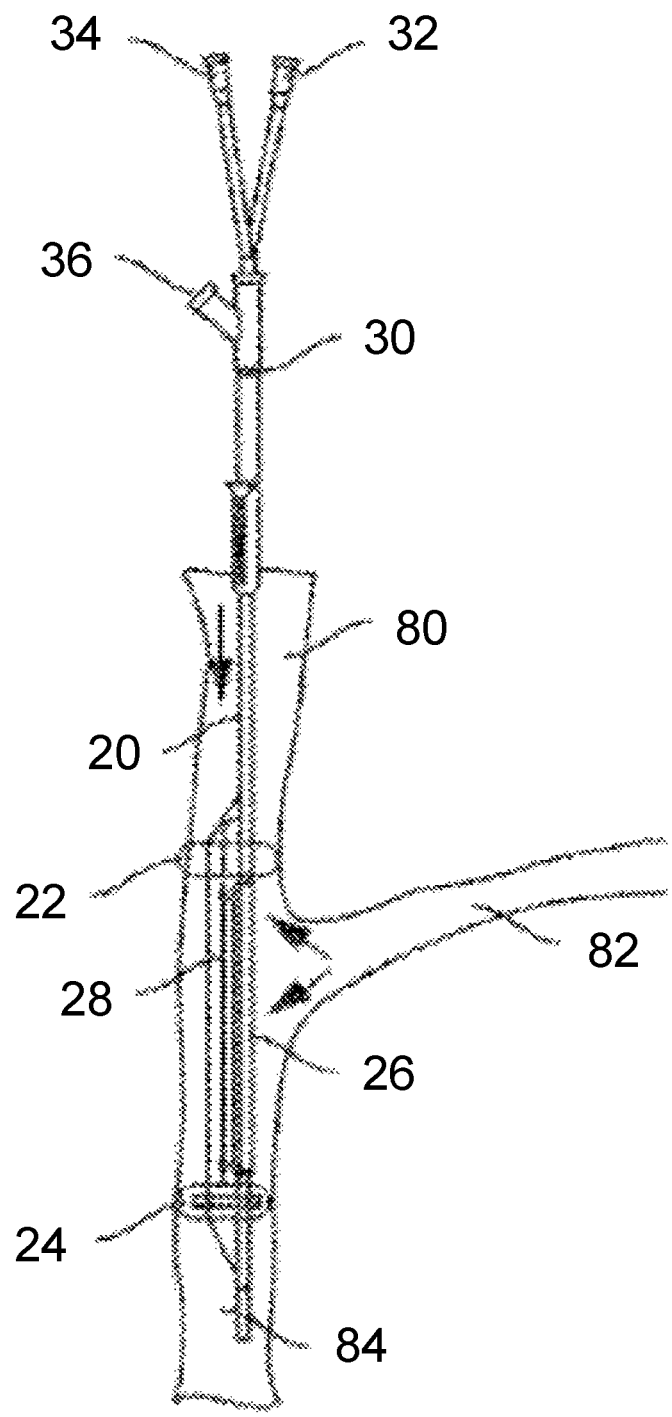
FIG. 27 is a schematic, partially cross-sectional view of a portion of the catheter system of FIG. 10 implanted in a patient.
Figure 28:
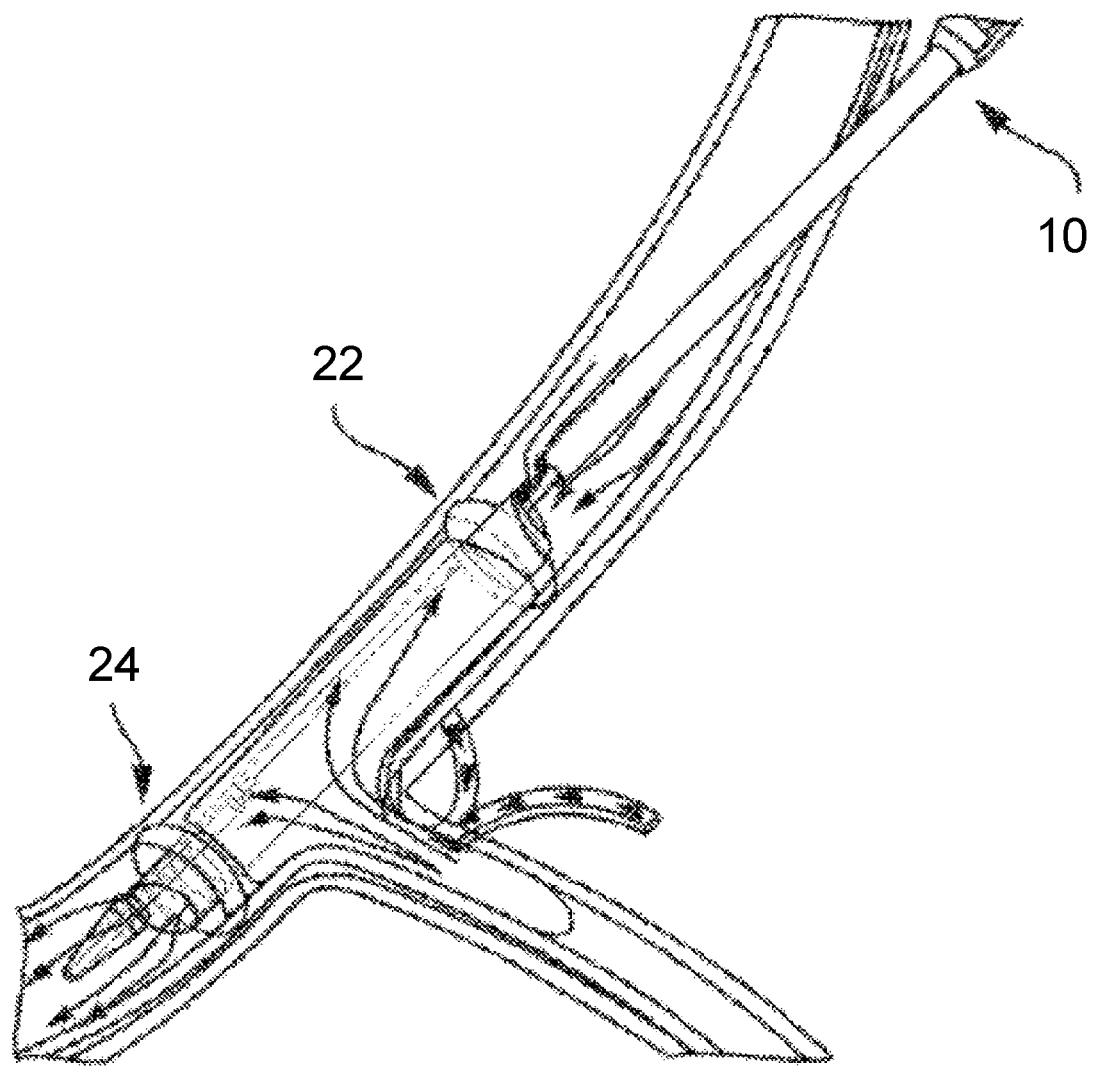
FIG. 28 is a perspective, partially cross-sectional view of another portion of the catheter system of FIG. 27 implanted in the patient.
Figure 29:
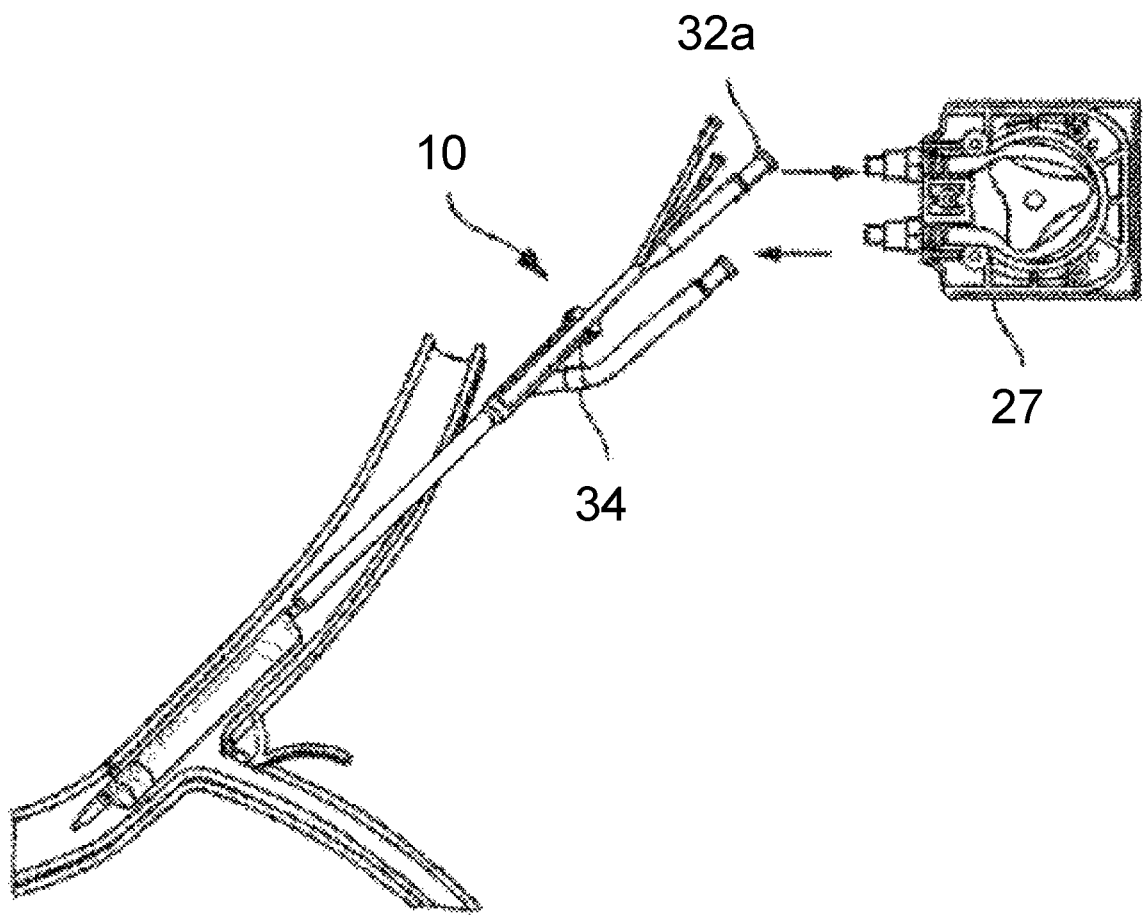
FIG. 29 is another perspective, partially cross-sectional view of the catheter system of FIG. 27 implanted in the patient.

FIG. 27 through FIG. 29 illustrate one example of the catheter 20 implanted within a patient, in particular within a jugular vein 80 of the patient. FIG. 28 also illustrates a location of the low pressure zone and illustrates fluid flow through the catheter 20 as indicated by two sets of arrows into and one set of arrows out of the catheter 20. FIG. 29 also illustrates one embodiment of a pump 27, a peristaltic pump (such as a peristaltic blood pump motor model 48 VDC, Head model 520RL2, sold under the trademark DRIVESURE from Watson Marlow), configured to pump fluid in and out of the catheter system 10 via the ports 32a, 34. As shown, the first restrictor 22, which in this illustrated embodiment is positioned at a region of the catheter 20 that is proximal to the suction port 26 and that marks the proximal or upstream boundary of the low pressure zone, can be positioned proximal to (upstream of) a point at which the patient's subclavian vein 82 enters the jugular vein 80. The second restrictor 24, which in this illustrated embodiment is positioned distally of the first restrictor 22 and between the suction port 26 and the distal end of the catheter 20, can be positioned distal to (downstream of) the point at which the subclavian vein 82 enters the jugular vein 80, and the second restrictor 24 can be in the patient's innominate vein 84. Alternatively, the catheter 20 can treat both lymphatic ducts by placing the first restrictor 22 proximal to (upstream of) the point at which the subclavian vein 82 enters the jugular vein 80 and placing the second restrictor 24 distal (downstream of) to the point at which both of the patient's innominate veins enters the subclavian vein 82. Alternatively, the second restrictor 24 can be positioned in the subclavian vein 82.

The catheter 20 can be positioned with the jugular vein 80 as shown in FIG. 27 and FIG. 28 in any of a variety of ways. For example, the positioning can be conducted using a 12 Fr sheath 30 to puncture the venous wall. The sheath 30 can be advanced into the vein 80 with the catheter 20, the flexible membrane 28, and the restrictors 22, 24 collapsed and contained therein. After insertion of the sheath 30, the catheter 20 along with the flexible membrane 28 and the restrictors 22, 24, can be advanced through the distal tip of the sheath 30 and positioned downstream of the sheath 30. Alternatively, the sheath 30 can be introduced first, and then the catheter 20 can be introduced by being advanced through the sheath 30. Regardless of whether the sheath 30 and the catheter 20 are introduced sequentially or simultaneously, the catheter 20 can be configured to be removed from the sheath 30 at any time. If at any time throughout a procedure there might be a question with regards to the integrity of the catheter 20, the catheter 20 being removable with the sheath 30 remaining in place within the patient allows the catheter 20 to be replaced with a new one introduced into the sheath 30 or for the catheter 20 to be reintroduced into the sheath 30 if the catheter's integrity is deemed acceptable.

The distal restrictor 24, when activated, isolates the incoming blood flow from the subclavian and jugular veins 82, 80 from the blood flow of the innominate vein 84 and ensures that all incoming blood is directed to the pump 27. The proximal restrictor 22, when activated, isolates the blood flow from the jugular vein 80 and ensures that all blood flow from a position upstream of the proximal restrictor 22 is transported through the flexible membrane 28. The pump is activated to maintain the jugular and innominate vein pressure and thus the nominal blood flow. The proximal restrictor 22, when activated, directs the blood flow from the jugular vein 80 and from the discharge port 36 within the sheath 30 down to the innominate vein 84. Actuation of the pump helps to create a low pressure zone in the vicinity of the junction of the jugular vein 80 and the subclavian vein 82 by withdrawing fluid in this region, recirculating it through the pump, and discharging the fluid upstream of this region through the sheath 30. Because the outflow of the thoracic and lymphatic ducts is located in this region, the lower pressure will facilitate drainage of lymphatic fluid.

Figure 30:
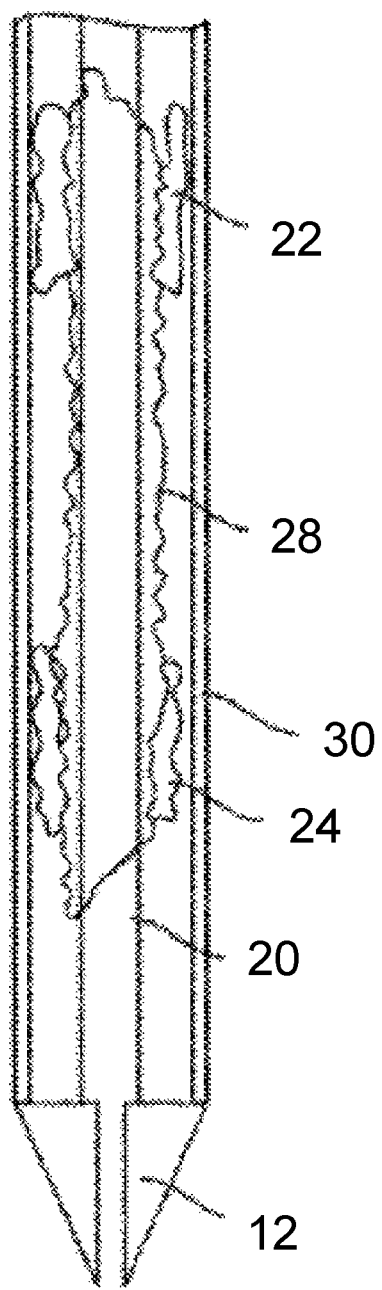
FIG. 30 is a side cross-sectional view of a distal portion of the catheter system of FIG. 10.
Figure 31:
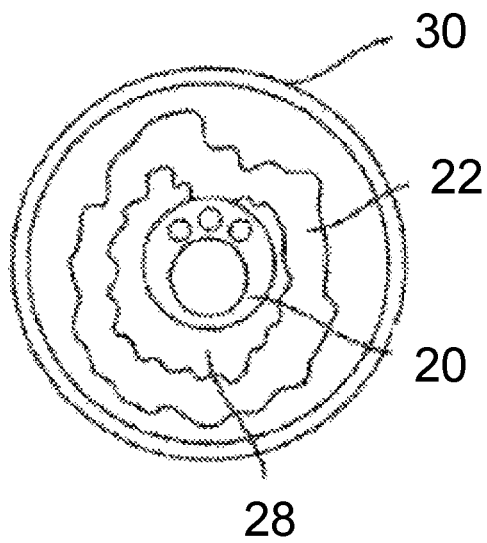
FIG. 31 is a cross-sectional view of the distal portion of the catheter system of FIG. 30.
Figure 32:
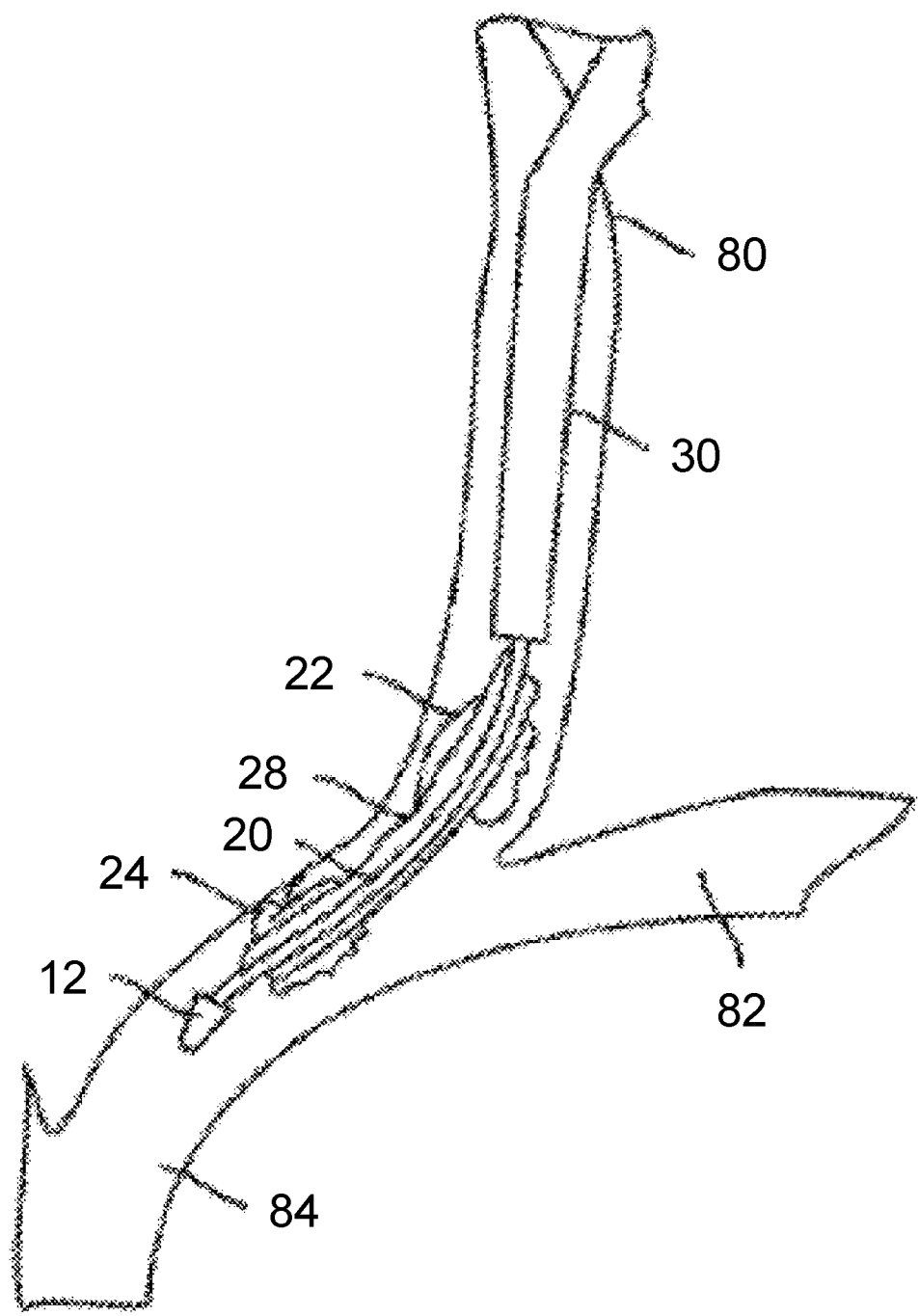
FIG. 32 is a schematic, partially cross-sectional view of a distal portion of the catheter system of FIG. 10 introduced into a vein.

The catheter 20 can be implanted in the jugular vein 80 as shown in FIG. 27 and FIG. 28 in any of a variety of ways. FIG. 30 through FIG. 32 illustrate one embodiment of implanting the catheter 20 can be implanted in the jugular vein 80. The catheter 20 can be similarly implanted in another vein, and other catheters described herein can be implanted in a vein similar to that discussed with respect to FIG. 30 through FIG. 32.

FIG. 30 and FIG. 31 illustrate the indwelling catheter system 10 (only a distal portion thereof is shown in FIG. 30) in an initial configuration in which the catheter 20 is disposed within the sheath 30 in a compressed configuration. In the initial configuration, the sheath 30 can have the catheter shaft 20 positioned therein, encircled by a compressed flexible membrane 28 further surrounded by compressed restriction members 22, 24.

A distal portion of the indwelling catheter system 10, e.g., a distal portion of the sheath 30, in the initial configuration can be inserted into the jugular vein 80 of the patient, which is the right internal jugular vein in this illustrated embodiment. A proximal portion of the indwelling catheter system 10, e.g., a portion including the ports 32, 34, 36, can remain outside the body of the patient to facilitate access to the ports 32, 34, 36. With the distal portion of the catheter system 10 at the target site (e.g., within the vein in which the catheter 20 is to be implanted), the catheter 20 can be advanced out of the sheath 30, as shown in FIG. 32, such that a proximal portion thereof is positioned within the jugular vein 80 and a distal portion thereof is positioned within the SVC 84. The suction port 26 disposed between the first and second restriction members 22, 24 enables suction of blood deposited within the low pressure zone from the subclavian vein 82 and from the innominate vein 84. Such arrangement enables drainage of both the patient's right lymphatic duct and thoracic duct. After positioning of the catheter 20 within the patient, the first and second restrictors 22, 24 can be expanded, e.g., moved from their relaxed configuration to their activated configuration, as shown in FIG. 27 and FIG. 28. The expansion of the restrictors 22, 24 also expands the flexible membrane 28, e.g., moved the flexible membrane 28 from a relaxed configuration to an activated configuration. As mentioned above, the restrictors 22, 24 can be expanded simultaneously or sequentially. As mentioned above, the expansion of the restrictors 22, 24 isolates a portion of the vein 80 in which the catheter 20 is deployed from a surrounding area, and, thus, an area (e.g., a low pressure zone) proximate to the thoracic duct is isolated and fluid can be removed via the suction port 26 positioned on the catheter 20 located within the isolated area.

The catheter system 10 discussed above is configured to pump blood out of a patient's body and back into the body. A catheter system can instead include an impeller, such as in the catheter embodiments of FIG. 1 through FIG. 6, such that blood need not be pumped out of and back into a patient's body and features of the catheter system 10 related thereto need not be included (e.g., a pump, a discharge port, and related tubing need not be included). The catheter system including an impeller can otherwise be similar to the catheter system 10, e.g., include a flexible membrane, include a sheath, etc.

The catheters described herein can be used in a variety of surgical methods, including surgical methods for treating pulmonary edema. The method can include verifying a location of the patient's thoracic duct and/or the patient's lymphatic duct, which can help a surgeon and/or other medical professional involved in performing a surgical procedure that includes implanting the catheter verify that the restrictor(s) of the catheter are implanted in the correct location within the patient. The verification can be performed in any of a variety of ways, as will be appreciated by a person skilled in the art, such as by using an imaging technique such as echo or fluoroscopy. In an exemplary embodiment, the verification can include advancing a set of pig tailed wires into the patient's subclavian or jugular veins and advanced toward a junction of the jugular and subclavian veins. Once one of the pig tailed wires enters the lymphatic duct or the thoracic duct, that one of the pig tailed wires can open itself inside the duct it entered, e.g., due to a default expanded configuration of the wire. The pig tailed wires can include, for example, a default expanded circle size of 4 cm. The location of the entered duct can be verified using an imaging technique that visualizes the expanded wire therein.

The verification can occur after the implantation of the catheter such that the implanted location of the catheter can be determined in view of the verification and adjusted if need be in view of the verification. Additionally or alternatively, the verification can be performed prior to the implantation of the catheter. Similarly, the verification can be performed prior to and/or after the restrictor(s) are moved from the relaxed configuration to the activated configuration to verify the position(s) of the restrictor(s), and the verification can be performed prior to and/or after one or more sensors are implanted to verify that the sensor(s) are desirably positioned. As discussed above, the sensor(s) in some embodiments are not implanted and are instead located outside the patient's body, and/or at least one sensor is implanted and at least one sensor is located outside the patient's body. Various embodiments of positioning tubes such as catheters is further described in U.S. Patent Publication No. 2015/0343136, incorporated by reference.

With the catheter implanted, the restrictor(s) in the activated configuration, and, if being used in the system, the sensor(s) positioned, fluid flow can be controlled with the pump. The control can generally occur as described above. In at least some embodiments, controlling the pump can include continuously running the pump. In at least some embodiments, controlling the pump can include periodically running the pump. In periodically running the pump, the pump can default to an idle state in which the pump is not pumping fluid. For example, in response to receipt of a user input requesting pumping, e.g., input by a user to an I/O device in electronic communication with the pump via a controller, input wirelessly to the pump, etc., the pump can be actuated so as to run and pump fluid. The pump can continue pumping until occurrence of a stop condition. Examples of the stop condition include a predetermined amount of time passing after the pump starts running and a second user input being received that requests pumping to stop. In response to the stop condition occurring, the pump can be actuated to return to its idle state. For another example, in response to sensing a particular parameter value (e.g., a particular pressure value, etc.) with one or more sensors, the pump can be actuated so as to run and pump fluid or the pump can be stopped so as to stop pumping fluid. The parameter can continue being measured with the one or more sensors, thereby allowing the pump to be controlled in real time in response to measured values.

Figure 33:
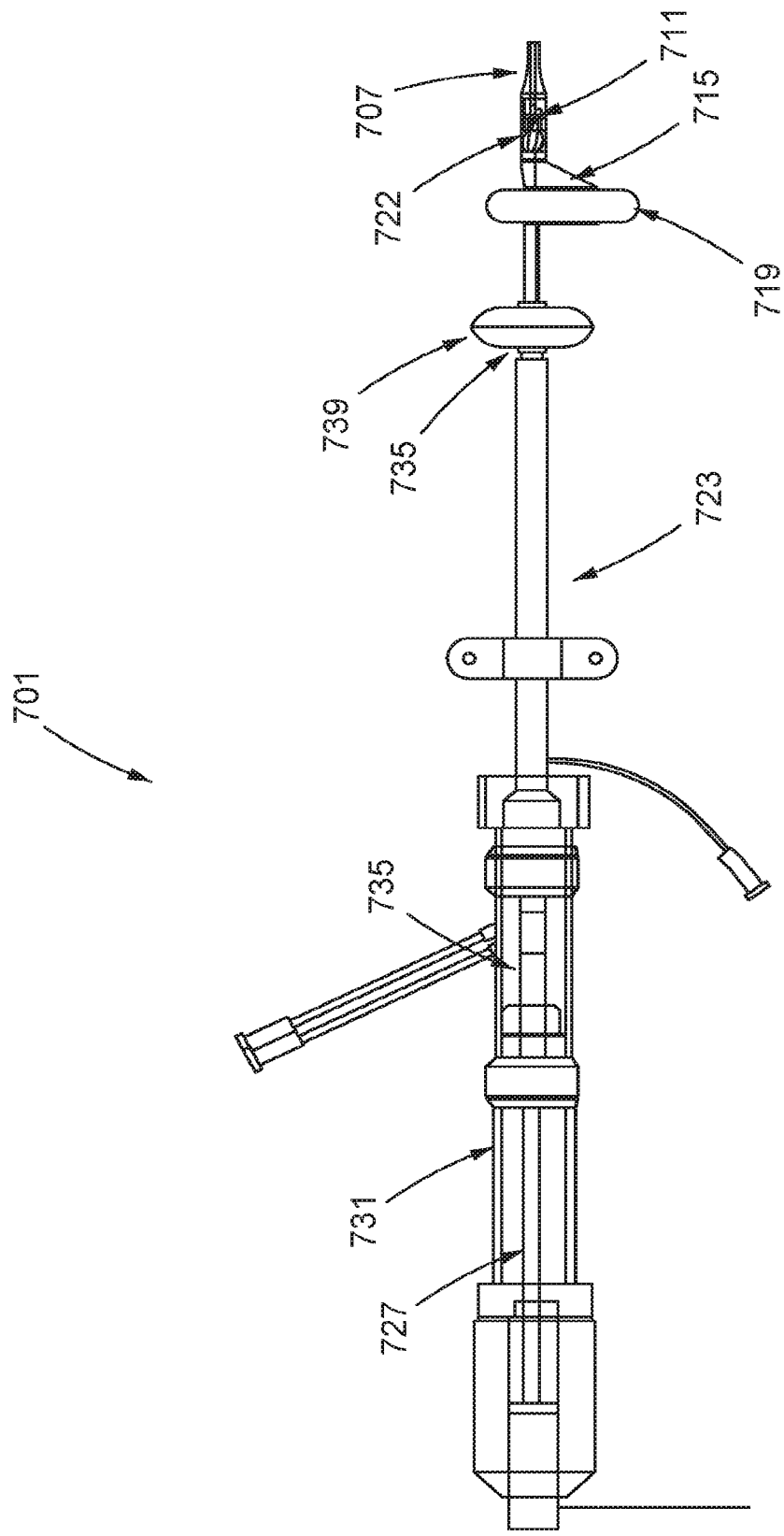
FIG. 33 is a perspective view of an implantable catheter system.

FIG. 33 illustrates one example of another catheter system 701 having distal, first restrictor 719, and a second restrictor 739. The catheter system 701 includes an indwelling catheter 727, which can be in the form of a disposable catheter unit, and a mechanical fixator part which can be enclosed in a sterile package prior to use. Some components of the system, such as a console having a controller, a display configured to display information and receive user input, cables, etc., can be reusable components. The catheter system 701 includes a catheter shaft 719 configured to be at partially implanted within a blood vessel of a patient; an impeller assembly 711 disposed at a distal portion 722 of the catheter shaft 719; a flexible membrane 715 connected to the distal portion 722 of the catheter shaft 719 (e.g., optionally to the impeller assembly); and the selectively deployable restrictor 715 attached to the distal portion 722 via the flexible membrane 715, such that deployment of the restrictor 719 causes the flexible membrane 715 to assume a tapered configuration, defining a tapered lumen extending through the restrictor, the flexible membrane, and at least a portion of the impeller assembly. The system 701 preferably further includes a proximal assembly 735 including a sheath 723 and a proximal balloon 739, as well as a centralizer 731 defining a portion of the main catheter 727.

As shown in FIG. 33, the system includes a main catheter with a distal assembly, a centralizer member, and a proximal assembly. The main catheter includes a propulsion system including at least an impeller and a motor (which can be disposed at least in part outside of the patient's body), a distal restriction member in the form of a distal balloon, and a distal atraumatic tip.

The centralizer member can be in the form of a housing encompassing a sealing component and at least a part of a motor. The housing is configured to keep the assemblies of the system aligned, while allowing an axial movement of the assemblies. The system includes a motor configured to move a drive shaft (e.g., a torque coiled drive shaft or a shaft having another configuration) inside a multi-lumen sleeve. In addition, the motor is configured to cause the distal balloon to inflate. One or more components of the motor can be disposed within the centralizer member.

The motor can be, for example, an extracorporeal motor configured to deliver the driving force to the impeller through the drive shaft. The motor can have a shaft with a channel extending therethrough to allow a guide wire to be inserted through the shaft. Additionally or alternatively, a mechanism configured to facilitate insertion and removal of the guide wire can be utilized. The catheter can include at least one inflation lumen through which an inflation fluid (e.g., air, liquid, etc.) can be introduced to inflate/deflate the restrictors. The restrictors can be inflate/deflate using separate components. The catheter can also include a suction lumen, and any other lumens.

The proximal assembly includes a proximal assembly tube having a proximal restriction member in the form of a proximal balloon at a distal end thereof. The proximal assembly is configured to regulate blood flow in the jugular vein. The proximal assembly can include a regulation mechanism configured to adjust the central venous pressure (CVP).

Figure 34:
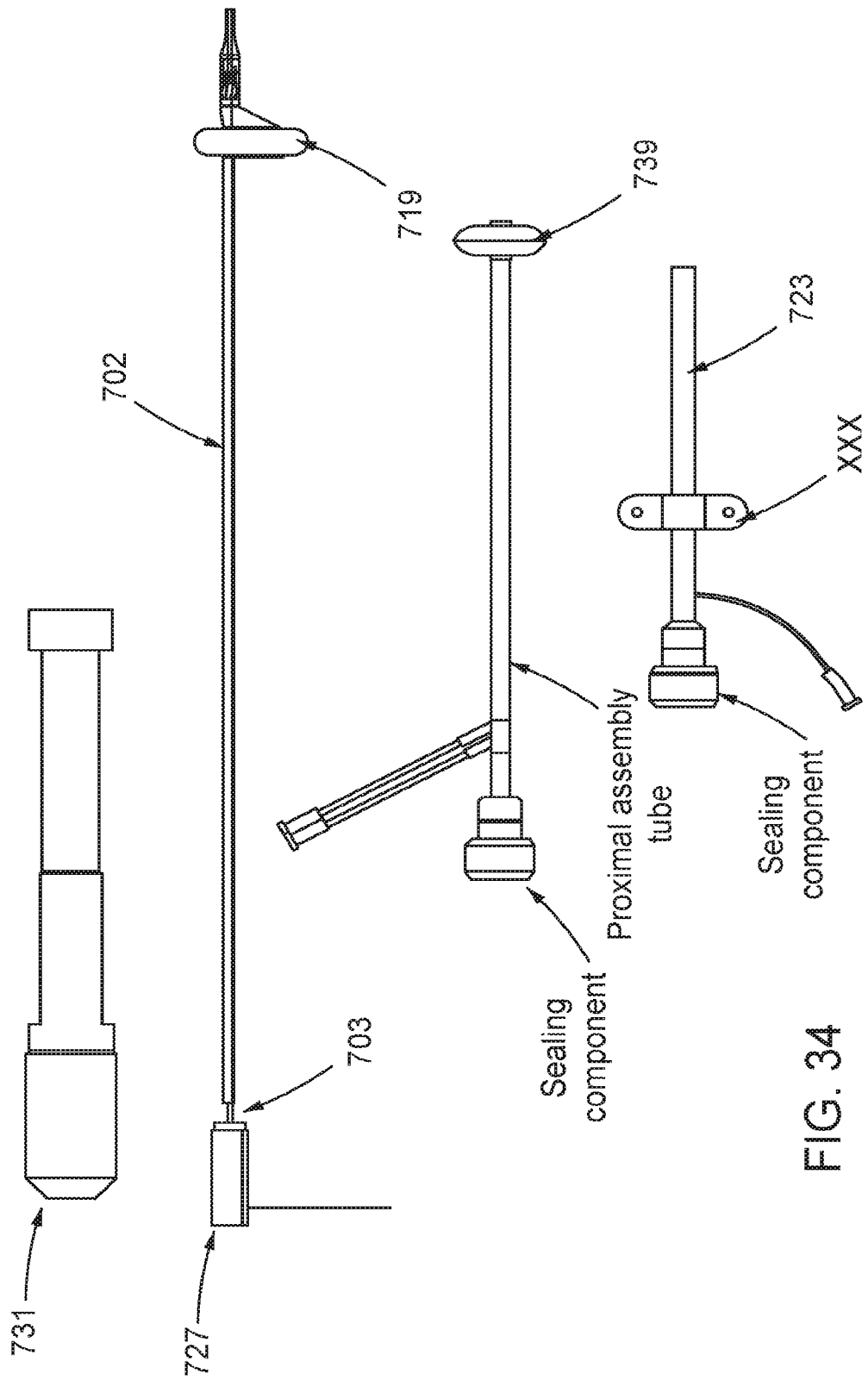
FIG. 34 is an exploded view of the implantable system of FIG. 33.

FIG. 33 through FIG. 35 show a distal end of the drive shaft is attached to an impeller assembly that includes the impeller and a housing or cage disposed around the impeller and having openings (e.g., radial openings) that allow blood to flow therefrom. A conical membrane is attached to the cage and at least partially wraps around the distal balloon.

FIG. 33 shows the catheter system 701 having a single selectively deployable restrictor 719 and a flexible membrane 715 and disposed in the left internal jugular vein to decrease the pressures distally of the restrictor 719. The system 701 includes an impeller assembly 711 disposed at a distal portion 722 of the catheter shaft 719. The flexible membrane 715 is connected to the distal portion 722 of the catheter shaft 719 (e.g., optionally to the impeller assembly). The sheath 723 includes components or fixtures configured to removably couple the catheter inside a patient. The sheath also has components operating as a cover sheath during deployment. As shown in FIG. 33, the drive shaft extends at least partially through a proximal assembly tube, and the centralizer encompasses at least a portion of the proximal assembly. The sheath is disposed so as to encompass at least a portion of the proximal assembly such that the proximal balloon is disposed distally to the distal end of the sheath.

FIG. 34 illustrates a portion of the proximal assembly.

FIG. 35 shows the distal assembly 722 that includes the impeller 712 that is driven by the motor to which it is coupled via the drive shaft 718.

FIG. 36 is a perspective view of the distal assembly 722 of the catheter system 701.

FIG. 37 is a back view back view of the distal assembly 722.

Figure 38:
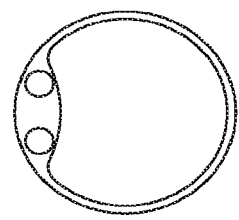
FIG. 38 shows a restrictor that regulates jugular flow and pressure.

FIG. 38 shows a proximal restrictor 739 that regulates jugular flow and pressure.

Figure 39:
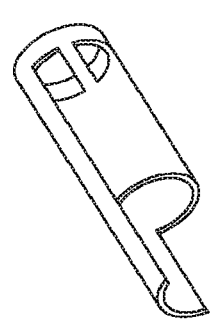
FIG. 39 is cross-section through a portion of the catheter.

FIG. 39 is cross-section through a portion of the catheter.

Figure 40:
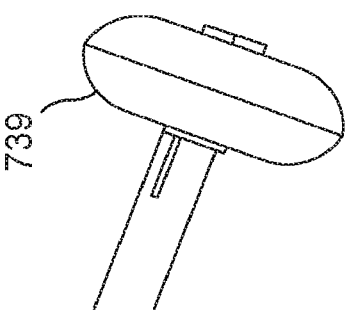
FIG. 40 shows an impeller for a catheter of the disclosure.

FIG. 40 shows an impeller 712 for a catheter system 701 of the disclosure.

Figure 41:
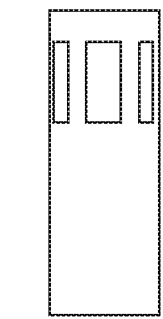
FIG. 41 is a side view of an impeller housing.

FIG. 41 is a side view of an impeller housing for the impeller assembly 711.

Figure 42:
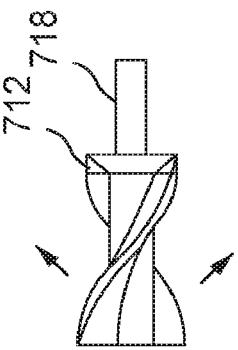
FIG. 42 is a perspective view of the impeller housing.

FIG. 42 is a perspective view of the impeller housing.

Figure 43:
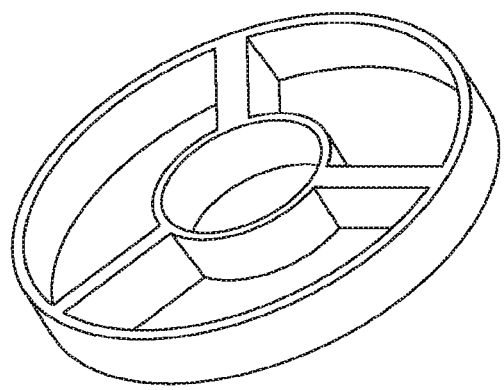
FIG. 43 shows the multi-strut support ring.

FIG. 43 shows the multi-strut support ring.

Figure 44:
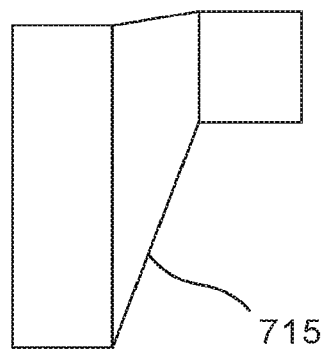
FIG. 44 is a detail view of the conical membrane.

FIG. 44 is a detail view of the conical membrane 415.

Figure 45:
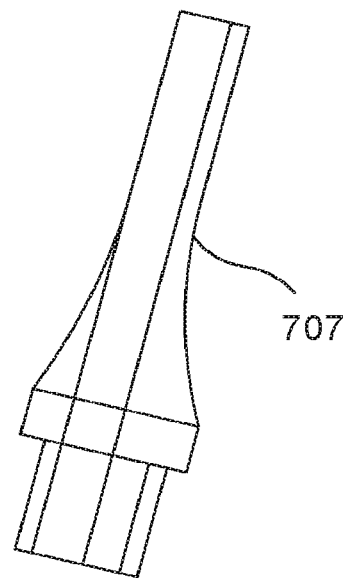
FIG. 45 shows the flexible, atraumatic tip.

FIG. 45 shows the flexible, atraumatic tip 707.

Figure 46:
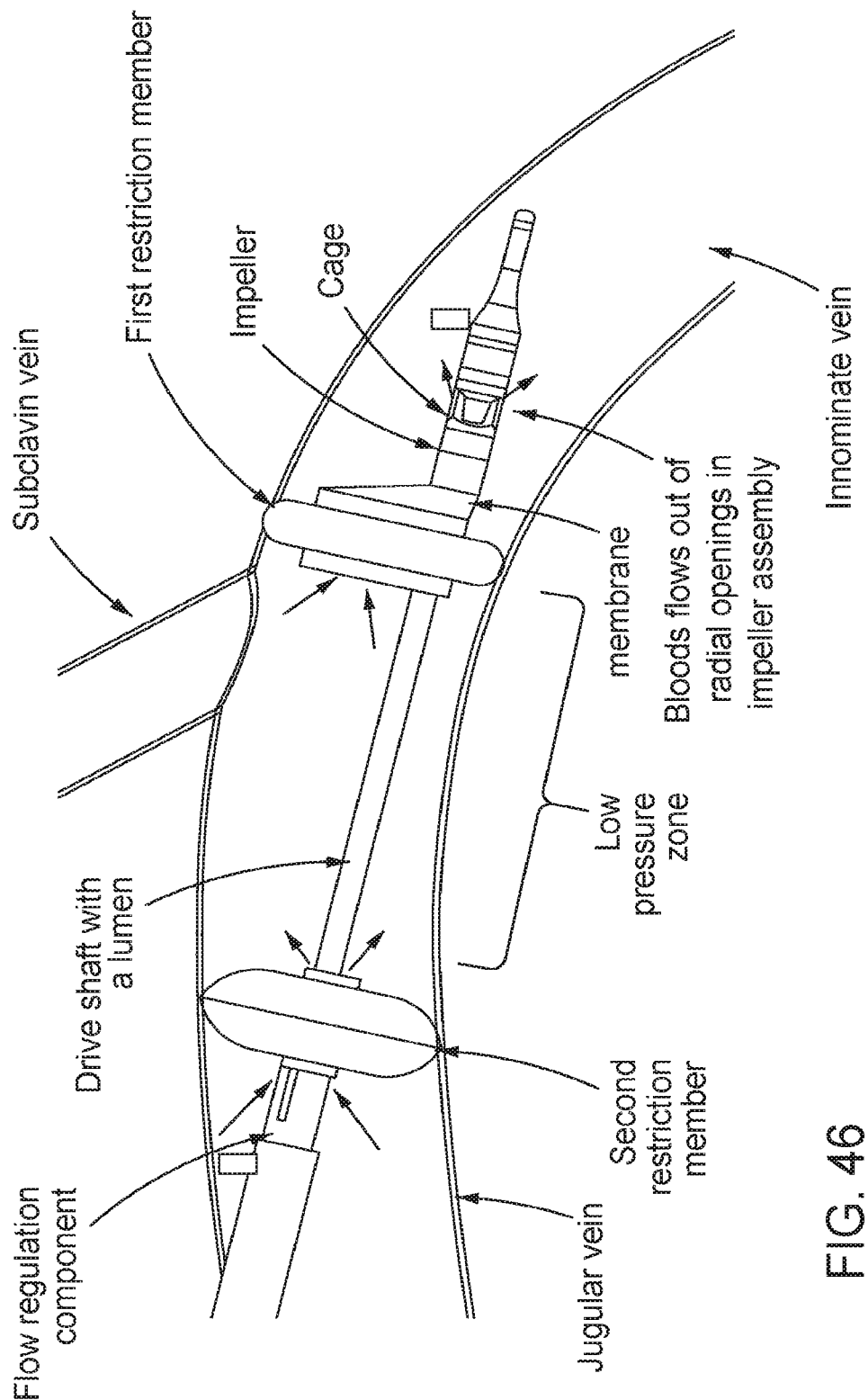
FIG. 46 is a perspective view of the implantable system of FIG. 33, showing the implantable system implanted in a body.

FIG. 46 illustrates the catheter system 701 in use in a method for treating edema with a straight multi-lumen configuration implanted in a patient's body.

Figure 47:
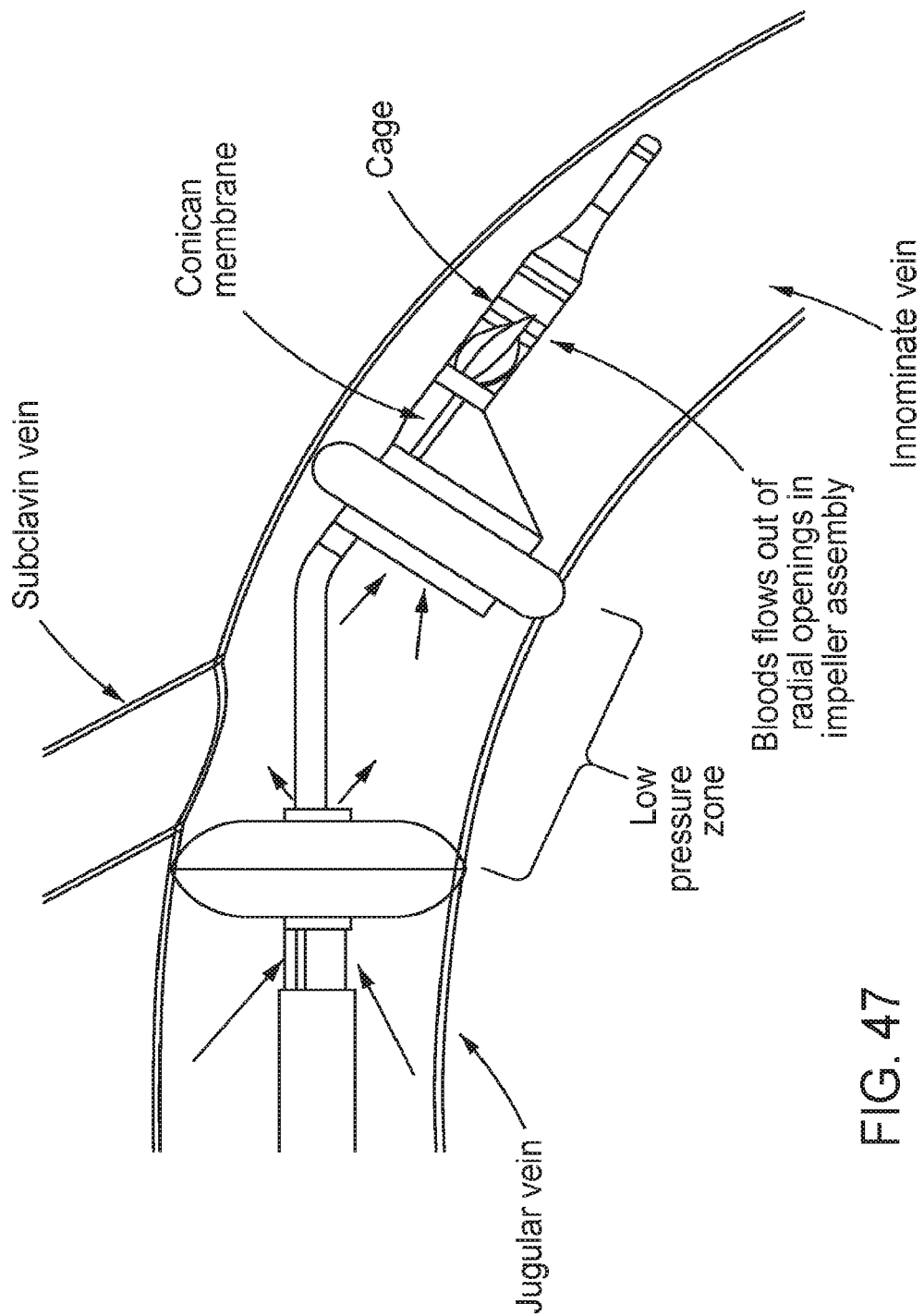
FIG. 47 is a perspective view of another implantable system, showing the implantable system implanted in a body.

FIG. 47 shows a similar catheter system, a closely related embodiment, implanted in a patient's body, the system having a bent or kink between the proximal and distal restrictors.

As shown in FIG. 46, the catheter system for treating edema includes an indwelling catheter configured for placement within a vein of a patient. The indwelling catheter includes a drive shaft having a lumen extending therethrough, wherein a distal portion of the drive shaft is operatively coupled to an impeller. The catheter also includes a first selectively deployable restriction member adjacent and proximal to the impeller. As shown, the first restriction member, which can be in the form of a distal balloon, has a membrane operatively coupled thereto and configured to direct fluid from an upstream side of the first restriction member to the impeller. The membrane can be a conical membrane, though it can have any suitable configuration. The catheter also includes a second selectively deployable restriction member (e.g., in the form of a proximal balloon) proximal to the first restriction member. The second restriction member is operatively coupled to a flow regulation component configured to direct a controlled volume of fluid from an upstream side of the second restriction member to a downstream side of the second restriction member. The jugular flow enters through openings formed in the flow regulation component and follows to the gap between the main catheter and an inner lumen of the proximal assembly. In this way, as shown by arrows in FIG. 46, blood flows from the upstream side of the second restriction member, enters a portion of the catheter between the first and second restriction members, and is directed to the downstream side of the second restriction member. The components through which blood flows have a common lumen extending therethrough. The impeller is rotated via the draft shaft by a motor.

In FIG. 46, the first and second restriction members are shown in the deployed configuration. The first restriction member can be, for example, doughnut shaped and it can allow for a maximum free flow of fluid and for minimal resistance. As shown in FIG. 46, the first and second restriction members can be implanted so as to create a low pressure zone between. In use, the system is operated so as to regulate a fluid flow in the low pressure zone. Transporting the fluid through the localized low pressure zone via can maintain a constant pressure within the low pressure zone. The second (proximal) restriction member is configured to regulate jugular flow and it is configured to restrict blood flow. The conical membrane can allow for diffusing the fluid flow from the isolated zone to the impeller. The geometrical shape of the membrane allows delivering the flow smoothly to the impeller and therefore reduces resistance to the flow. The system in FIG. 47 can be configured similar to that in FIG. 46.

Some examples of various components of the catheter system and examples of dimensions of the components are discussed for the proximal assembly and distal assembly.

FIG. 38 shows a restrictor that regulates Jugular flow and pressure by having 1-4 opening sections at its proximal side and allow for the jugular flow (e.g., 300-500 ml/min) to enter through the sections and in the gap between the main catheter and an inner lumen of the proximal assembly. An example of a section dimension range: 1×5 mm.

FIG. 39 is cross-section through a portion of the catheter showing a structure that supports and holds the proximal balloon.

FIG. 40 shows the Impeller. The impeller functions as the driving mechanism of the blood. It pumps blood from the center portion of the system and drives it distally and outward towards the vessel perimeter. The impeller may include more than one (e.g., 2-4, or greater than 4) blades. The rotation speed should be <25000 @ 11/min in order to reduce hemolysis risk. The impeller shaft contains a lumen in which a guide wire can pass through.

FIG. 41 is a side view of the cage, or impeller housing. The dimensions follow the impeller dimensions with a minimal gap between them (0.05-0.2 mm)

FIG. 41 is a perspective view of the cage. Preferably, the cage can include an extension to support the catheter while keeping the suction lumen fully open.

FIG. 44 is a detail view of the conical membrane. The conical membrane can allow for diffusing the flow from the isolated zone to the impeller. The geometrical shape will deliver the flow smoothly to the impeller and therefore reduce resistance to flow. The conical length (LI) shall be 2-10 mm.

FIG. 43 shows the multi-strut support ring. This ring holds the drive shaft centralized and keep the impeller in place.

FIG. 45 shows the flexible, atraumatic tip. The tip allows a gentle insertion to the vessel and allows for a guide wire insertion. The tip is connected to the cage at its proximal end. In some embodiments, the tip has a length of about 0.5-15 mm.

It should be appreciated that the components of the system are shown by way of example only, and that the dimensions of the components are shown by way of example only.

The catheter system also includes a controller that can be configured to be in electronic communication with at least one pressure sensor (not shown). A person skilled in the art will appreciate that a variety of suitable sensors can be used for monitoring pressure, such as central venous pressure (CVP) or other fluid pressure sensors, and blood pressure sensors. The at least one pressure sensor can be implanted in the patient as part of the impeller, implanted in the patient as a separate component from the impeller, or the at least one pressure sensor can be located external to the patient, such as by being on a skin surface thereof. If not already a part of the impeller so as to be in electronic communication therewith, the at least one pressure sensor can be configured to be in electronic communication with the impeller over a communication line such as a wired line or a wireless line.

In an exemplary embodiment, three pressure sensors can be implanted in the patient. One of the pressure sensors can be implanted between the first and second restriction members as to be in the low pressure zone. Another pressure sensor can be implanted in the vein proximal to the second restriction member, and another pressure sensor can be implanted in the vein distal to the first restriction member, so as to be in the higher pressure zones. The sensors can allow a pressure differential to be determined between the low pressure zone and the higher pressure zone. In other embodiments, another number of pressure sensors can be implanted in the patient (e.g., one, three, four etc.) and/or the pressure sensor(s) can be implanted at other locations.

The catheter can include at least one lumen (not shown) configured to facilitate use of the pressure sensor(s), for example to facilitate placement of the pressure sensor(s) and/or to be filled with a fluid such as saline to allow for external pressure measurement.

In addition to or instead of the one or more pressure sensors, the controller can be configured to be in electronic communication with at least one other type of sensor (not shown) configured to sense a parameter other than pressure. Examples of sensors that can be used to measure a parameter other than pressure include radio frequency transmitters and receivers, fluid sensors, bioimpedance sensors, heart rate sensors, breathing sensors, activity sensors, and optical sensors. Examples of the measured parameter include fluid amount (e.g., as measured by a fluid sensor, such as a fluid sensor placed in a lung to sense fluid amount in the lung), bioimpedance (e.g., as measured by a bioimpedance sensor), heart rate (e.g., as measured by a heart rate sensor), breathing rate (e.g., as measured by a breathing sensor), patient activity level (e.g., as measured by an activity sensor), and organ dimension (e.g., as measured by an optical sensor). The sensor can be implanted in the patient as part of the pump, implanted in the patient as a separate component from the pump (e.g., implanted in an interstitial space around a lung, implanted at a junction of a right subclavian vein of a patient and an internal jugular vein of the patient, implanted at a junction of a left subclavian vein of a patient and an internal jugular vein of the patient, etc.), or the sensor can be located external to the patient, such as by being on a skin surface thereof.

The controller can include any type of microprocessor or central processing unit (CPU), including programmable general-purpose or special-purpose microprocessors and/or any one of a variety of proprietary or commercially available single or multi-processor systems. The controller can be a component of a control system that includes any number of additional components, such as a memory configured to can provide temporary storage and/or non-volatile storage; a bus system; a network interface configured to enable the control system to communicate with other devices, e.g., other control systems, over a network; and an input/output (I/O) interface configured to connect the control system with other electronic equipment such as I/O devices (e.g., a keyboard, a mouse, a touchscreen, a monitor, etc.) configured to receive an input from a user. The controller can be configured to receive user input thereto to control any of a variety of aspects related to the catheter, such as speed of the motor and ideal range of pressure for the low pressure zone.

In use, the catheter system can be attached to a patient near an incision point. One or more electronic cables can be connected to a multiuse console that includes a motor controller, a pressure sensor amplifier, firmware with data acquisition system, power supply, touch screen monitor, and any other suitable components.

FIG. 62 diagrams steps of a method of implanting a catheter system, to implant the system, a sterile catheter kit is shipped to the clinical site in its open state, in which a distal portion of a distal assembly is unsheathed (s1). Prior to an implanting procedure, a user (e.g., a physician assistant) can insert the distal assembly into a sheath lumen, e.g., by using a handle Tuhy (s2). The catheter is then inserted by the physician over a guide wire into the jugular vein (e.g., posterior approach) (s3). Once it is confirmed (using, e.g., an ultrasound technique) that the catheter is located in the jugular vein, the operator can un-sheath the distal unit in two consecutive steps. First, the distal balloon can be un-sheathed and positioned in the innominate vein just past the subclavian drainage (s5, s6). Second, the proximal balloon is disposed in the jugular vein, above the subclavian vein (s8).

The guide wire can be pulled out and the sheath is fixated to the skin in a location that allows the maximal axial adjustment of the assembly. After the fixation, the centralizer is positioned, and an electric cable is connected (s9). The motor is activated (e.g., using a controller that can be accessed via a console graphical user interface (GUI)) and causes the distal and proximal balloons to inflate. The distal balloon can be inflated prior to inflating the proximal balloon. The CVP can be measured through a sheath luer. The pressure can be adjusted using a catheter handle by bringing the proximal assembly closer to the sheath or away from the sheath (or any other mechanism) (s10). The motor can drive the impeller to induce the low pressure zone by causing fluid to be pumped through the catheter. In this way, the system can operate automatically to keep the low pressure zone (or "isolated zone") at a nominal pressure value of, for example, 2.5±2.5 mmHg. This can be done be controlling the motor RPM.

In general, the described catheter system is configured to seal a zone at the bifurcation of the patient's jugular and subclavian veins using the distal and proximal balloons. As the impeller is operated, the blood is directed from the low pressure zone such that the pressure inside that zone is reduced. The motor receives feedback from one or more pressure sensors, and the pressure can be regulated by the motor RPM. The CVP can be adjusted by a regulation mechanism at the proximal assembly.

As discussed above, a catheter can include proximal and distal restrictors. Also, a catheter can include can only one selectively deployable restriction member or restrictor, for example, a restrictor that corresponds to a proximal restrictor. Furthermore, the inventors have surprisingly discovered that a single restriction member or another similar component can be used to restrict a blood flow in a vein to control pressure distally of the restrictor and throughout the venous system. In some embodiments, the restrictor can be a proximal restrictor. It should be appreciated that the single restrictor is referred to herein as a "proximal" restrictor because it is placed proximally of an outflow port of a duct. This can be the same or similar location at which a proximal restrictor of a two-restrictor catheter having distal and proximal restrictors can be placed. Inflation of a single restrictor (which can include an inflatable balloon) allows reaching a working point of a low pressure reading in a venous angle (lymphatic outflow) pressure sensor.

The embodiments where the catheter includes a single restrictor do not require a pump or other suction device. Rather, the heart during the diastolic filling phase acts as a suction pump and needs to be filled by a certain amount of blood at certain time duration (diastole). The venous system acts as a filling reservoir for the right heart to pump blood in. Because part of the venous system is constricted via a catheter's single restrictor, the heart needs to pump in harder and reduce its pressures in order to fill in the same amount of blood.

Accordingly, in some embodiments, to reduce venous pressure locally, such as at the thoracic duct outflow or systemically throughout the venous system, a single selectively deployable restrictor can be placed in a vein in a patient's body such that it completely or partially blocks a blood flow through that vein. The vein should be a relatively large vein that has blood flow from about 300 mm/min to about 500 mm/min. The inventors have surprisingly discovered that implanting a catheter with a single restrictor in a vein results in a reduction of the pressures during the diastolic filling phase of the ventricle and enables local vein pressure reduction. For example, in at least some embodiments, a catheter including an inflatable balloon or other type of restrictor with a controlled tunnel or lumen extending therethrough can be placed in the jugular vein and activated to allow the flow from the jugular vein through it and thus reduce the pressures at the thoracic duct outflow.

Figure 48:
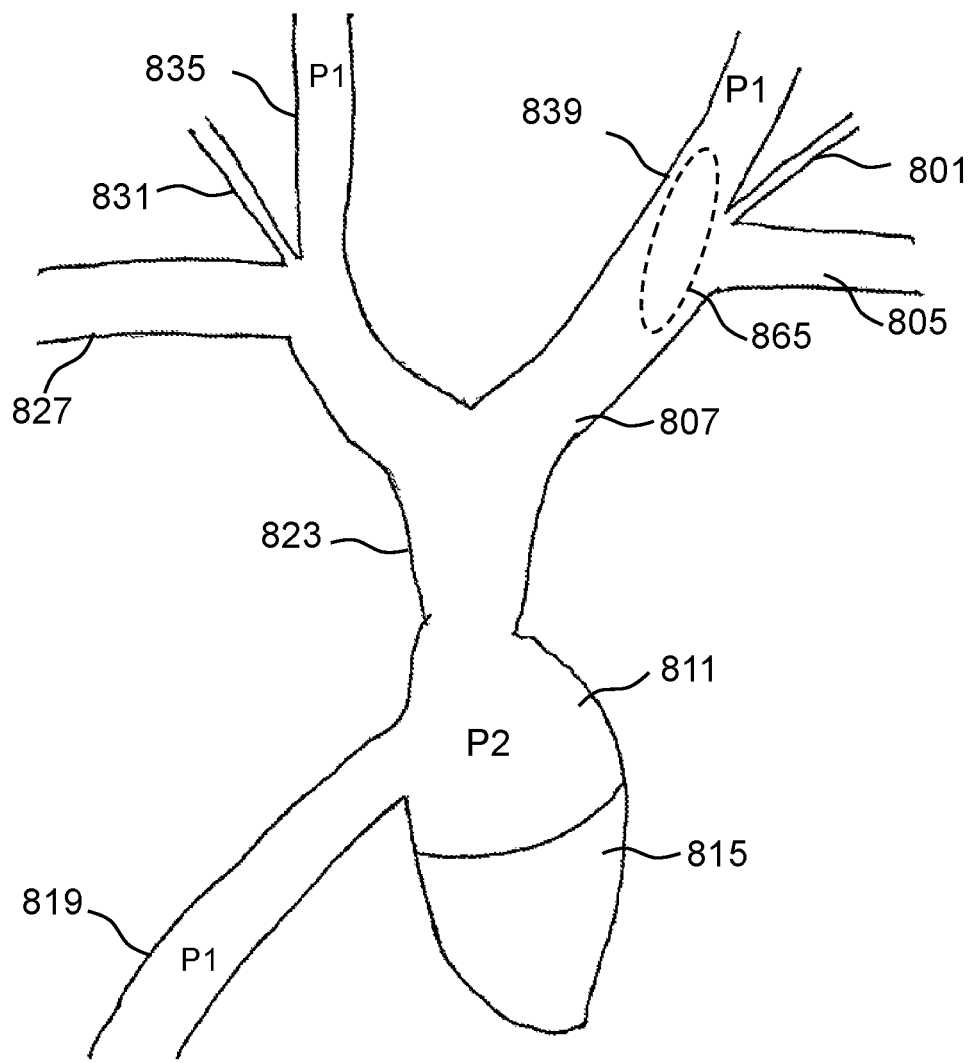
FIG. 48 is a schematic view of a portion of the venous system of a patient.

FIG. 48 illustrates schematically a portion of the venous system of a patient where a catheter can be implanted. The system includes a thoracic duct 801, a left subclavian vein 805, an innominate vein 807, a right atrium 811, a right ventricle 815, an inferior vena cava 819, a superior vena cava 823, a right subclavian vein 827, a lymphatic duct 831, a right internal jugular vein 835, and a left internal jugular vein 839. Methods of the invention include reducing pressure at an outflow of a duct by positioning, in a blood vessel in a region 865 near an output of a duct, a device comprising a tapered lumen and pumping blood from a wide end of the tapered lumen to a narrow end to thereby lower pressure near the output of the duct.

Normal venous physiology and pressures are illustrated. Thus, pressure areas having P1 pressure and P2 pressure are indicated. Normal blood pressure measured at a patient supine position is as follows: P1 is approximately 5 mm Hg and P2 is approximately 3 mm Hg. At a heart failure (supine position), P1 is approximately 15 mm Hg and P2 is approximately 13 mm Hg. Methods of the disclosure reduce pressure at least at the region 865 near an output of a duct so that the pressure is closer to 5 mm Hg than to 15 mm Hg.

Figure 49:
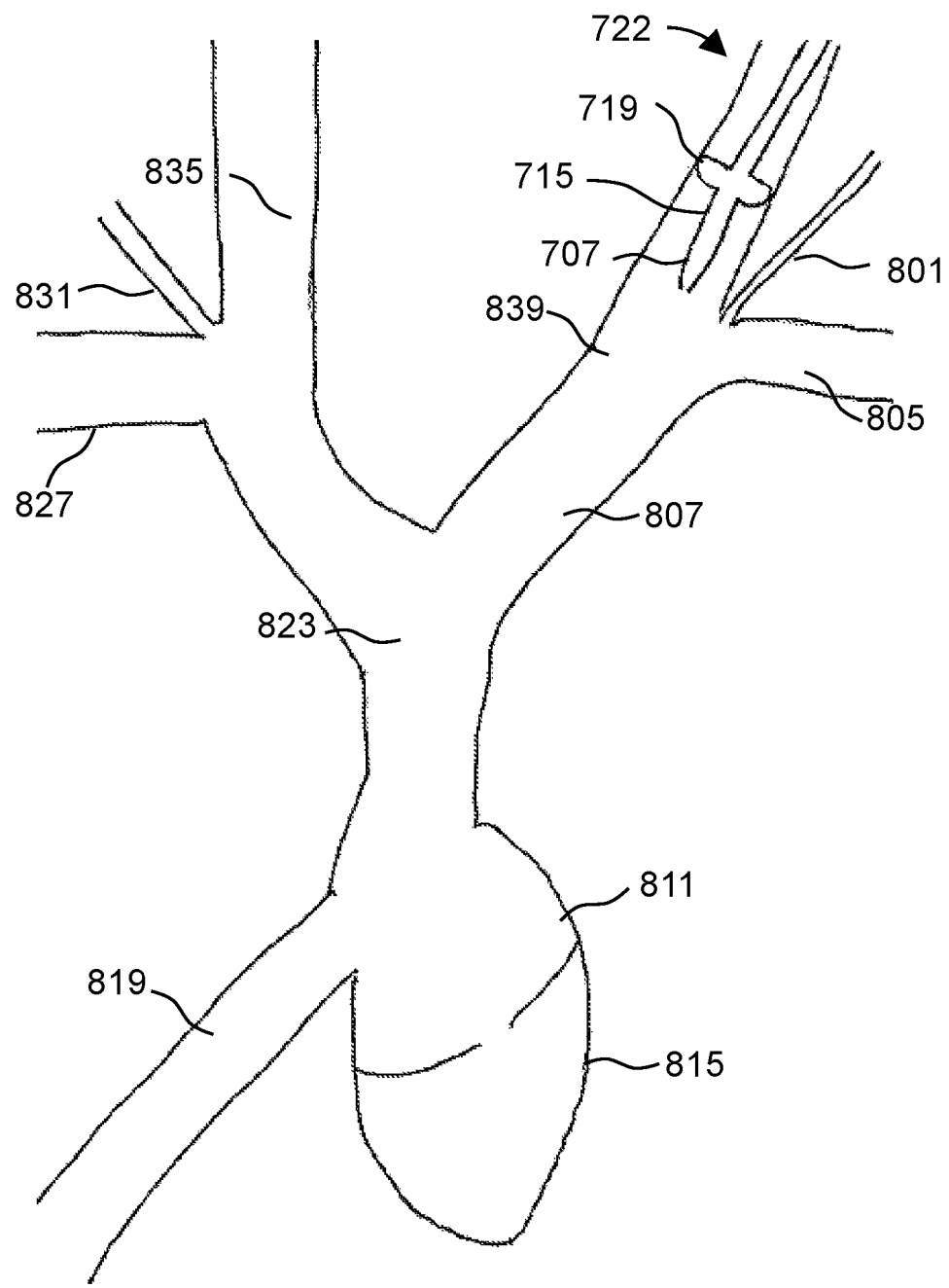
FIG. 49 is a schematic view of a portion of a catheter implanted in the venous system of FIG. 48.

FIG. 49 illustrates schematically the portion of the patient's venous system (as also shown in FIG. 48), with a catheter system 701 having a single selectively deployable restrictor 719 and a flexible membrane 715 and disposed in the left internal jugular vein to decrease the pressures distally of the restrictor 719. The system 701 includes an impeller assembly 711 disposed at a distal portion 722 of the catheter shaft 719. The flexible membrane 715 is connected to the distal portion 722 of the catheter shaft 719 (e.g., optionally to the impeller assembly). The restrictor 715 is configured to restrict blood flow within the vein when the restrictor is activated, and the restrictor includes a balloon that is configured to be inflated. In some embodiments, the restrictor disposed in a vein may not restrict the blood flow entirely—e.g., about one third, or other portion, of the flow can be restricted. The amount of the reduction in blood flow through the vein can depend on a desired reduction of blood pressure. Pressure upstream and downstream of the single restriction member is monitored using suitable sensors, such as blood pressure sensors.

The catheter system having a single selectively deployable restrictor can be configured in many various ways and it can include components similar to any of the components described herein in connection with FIG. 1 through FIG. 47. However, the catheter system with a single selectively deployable restrictor differs from two-restrictor catheter systems. For example, it does not include a suction pump, and other components included in a two-restrictor catheter can be omitted or modified. The single selectively deployable restrictor can be configured in many various ways and using suitable materials, including the materials described hereinabove. Also, the catheter system with a single selectively deployable restrictor can be implanted in a vein using various techniques.

The single selectively deployable restrictor is configured to control a volume of fluid from an upstream side of the restrictor to a downstream side (towards the heart) of the restrictor member to cause a pumping force of the heart during diastole to be increased to thereby cause pressure at the downstream side to be decreased. The catheter system does not include a suction pump and the heart acts as such a pump.

In some embodiments, the catheter has a flexible membrane having a balloon coupled to at least a portion thereof and having a lumen or tunnel extending therethrough. When the balloon is activated to be expanded, this also causes the membrane to expand, e.g., the membrane is moved from a relaxed configuration to an activated configuration. In this way, the membrane in the activated configuration (e.g., as shown in FIG. 49) defines a lumen or tunnel formed in a controller manner. In the illustrated embodiments, the balloon can be configured so as to constrict the membrane in the activated configuration, which can cause a diameter of the tunnel of the membrane to be decreased. For example, when the balloon is expanded within a vein, the balloon becomes constricted by the inner wall of the vein. The balloon can be expanded until it is in an expanded configuration in which it constricts the membrane to thus decrease a size of the tunnel through the membrane to a desired size. The diameter of the tunnel can be much smaller than that of a vessel (e.g., a jugular vein or an innominate vein) in which the catheter is placed. For example, in at least some embodiments, the diameter of the tunnel can be in a range of from about 2 mm to about 4 mm. Also, in some embodiments, the diameter of the tunnel can be in a range of from about 1 to 4 mm.

When the catheter including a single selectively deployable restrictor is disposed in a vein and the restrictor is activated, the single restrictor provides, in combination with other components, occlusion within the vein. The catheter is configured such that, when its single restrictor at least partially occludes the vein, fluid is allowed to flow through the catheter so as to cause the heart during its diastolic phase to pump blood in harder in order to refill again. The catheter can include a lumen or tunnel extending through the restrictor (which can be a lumen extending through a flexible membrane to which the restrictor is coupled or a lumen formed in a catheter's shaft) that allows fluid to flow therethrough. The tunnel acts as a restrictor that forces the heart to pump in blood harder such that the diastolic suction forces of the heart are increased. This causes a decrease in the pressure in the heart during the diastolic phase when the heart is sucking blood in from the surrounding veins and thus the end diastolic volume of the right heart is preserved and the preload to the heart is lowered. In this way, the pressure can be reduced anywhere in the venous system (and the lymphatic outflow) by introducing a catheter with a balloon or any other type of an adjustable restrictor. Thus, a low pressure region can be created in parts of the patient's venous system except a part of the patient's venous system upstream of the single restrictor.

Accordingly, the restrictor placed distally towards the heart can be activated to greatly reduce the pressure as a function of the restrictor size (which can be adjustable) and the operation of the heart. The catheter can be configured to be used for a short time such, or the catheter can be implanted such that it remains implanted in a patient's body for several days or weeks.

In some embodiments, a diameter of the catheter shaft can be from about 4 Fr (French units) to about 9 Fr, and the catheter can include a compliant balloon and an internal membrane that has a lumen having a diameter in a range of from about 1 mm to about 4 mm. The operation of the catheter can be controlled and it can be placed at the left internal jugular vein or the right internal jugular vein, or at other locations in the venous system.

Referring back to FIG. 49, when the catheter with the restrictor is placed as shown, during the diastolic phase, pressure P2<pressure PI, and pressure P3<pressure P2. The pressure PI is measure upstream or proximally of the catheter, the pressure P2 is measured downstream or distally of the catheter and in other parts of the venous system, and the pressure P3 is measured at the heart. In these embodiments, a higher pressure zone is proximal to the proximal restrictor, and a low pressure zone is distal to the proximal restrictor. Moreover, as shown in FIG. 49, a higher pressure zone (PI) is proximal to the proximal restrictor and a low pressure zone (P2) includes other parts of the venous system, except the part that is upstream of the restrictor where the pressure is PI.

Figure 50:
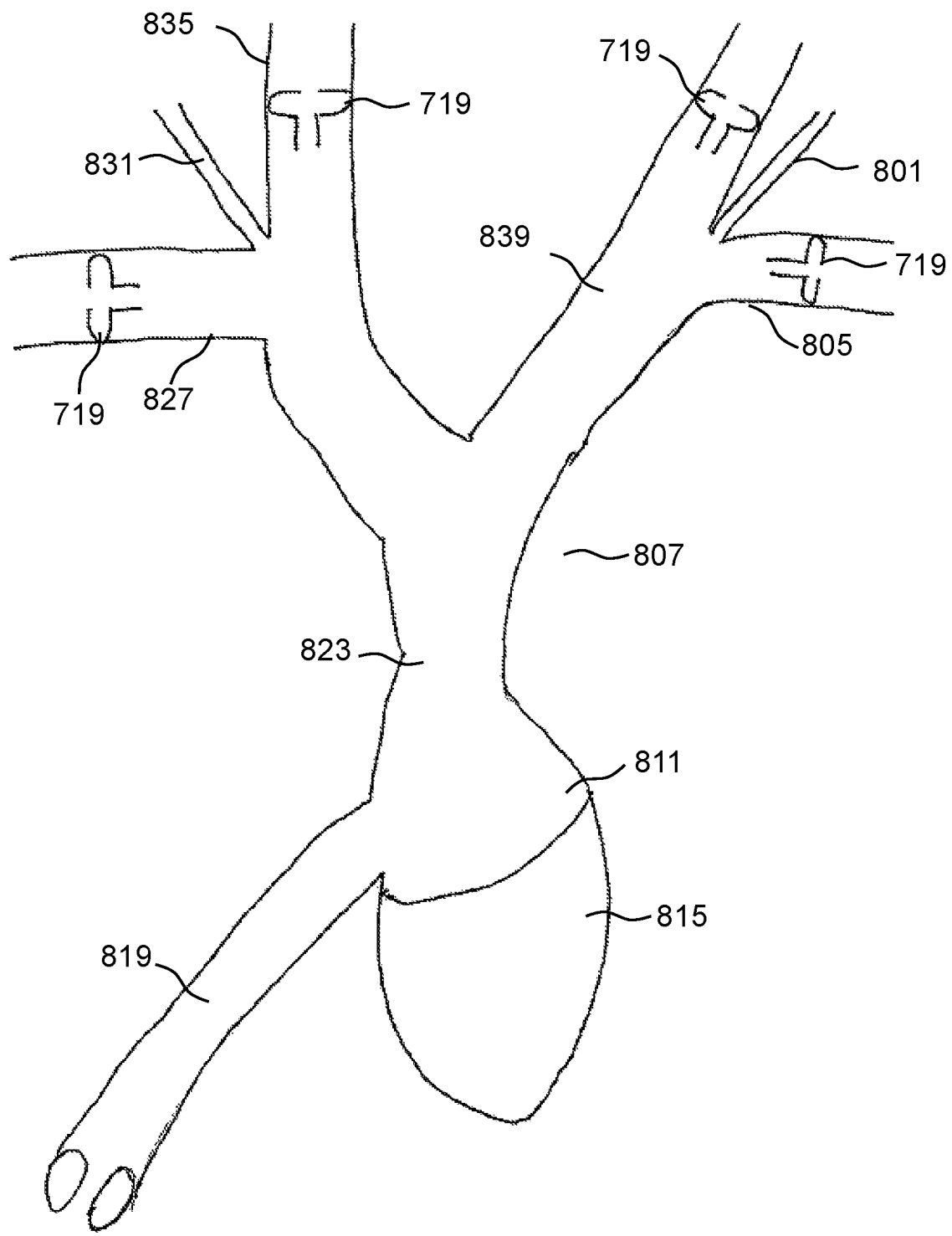
FIG. 50 is a schematic view of a portion of the venous system of a patient, illustrating locations at which a catheter having a single restriction member can be placed.

FIG. 50 illustrates schematically examples of possible locations of the catheter and restrictor 719 within a patient's body. For example, the catheter, which can be implantable, can be disposed in the right subclavian vein, left subclavian vein, right internal jugular vein, left internal jugular vein, and inferior vena cava. Also, in some embodiments, the catheter can be disposed at the femoral vein.

Figure 51:
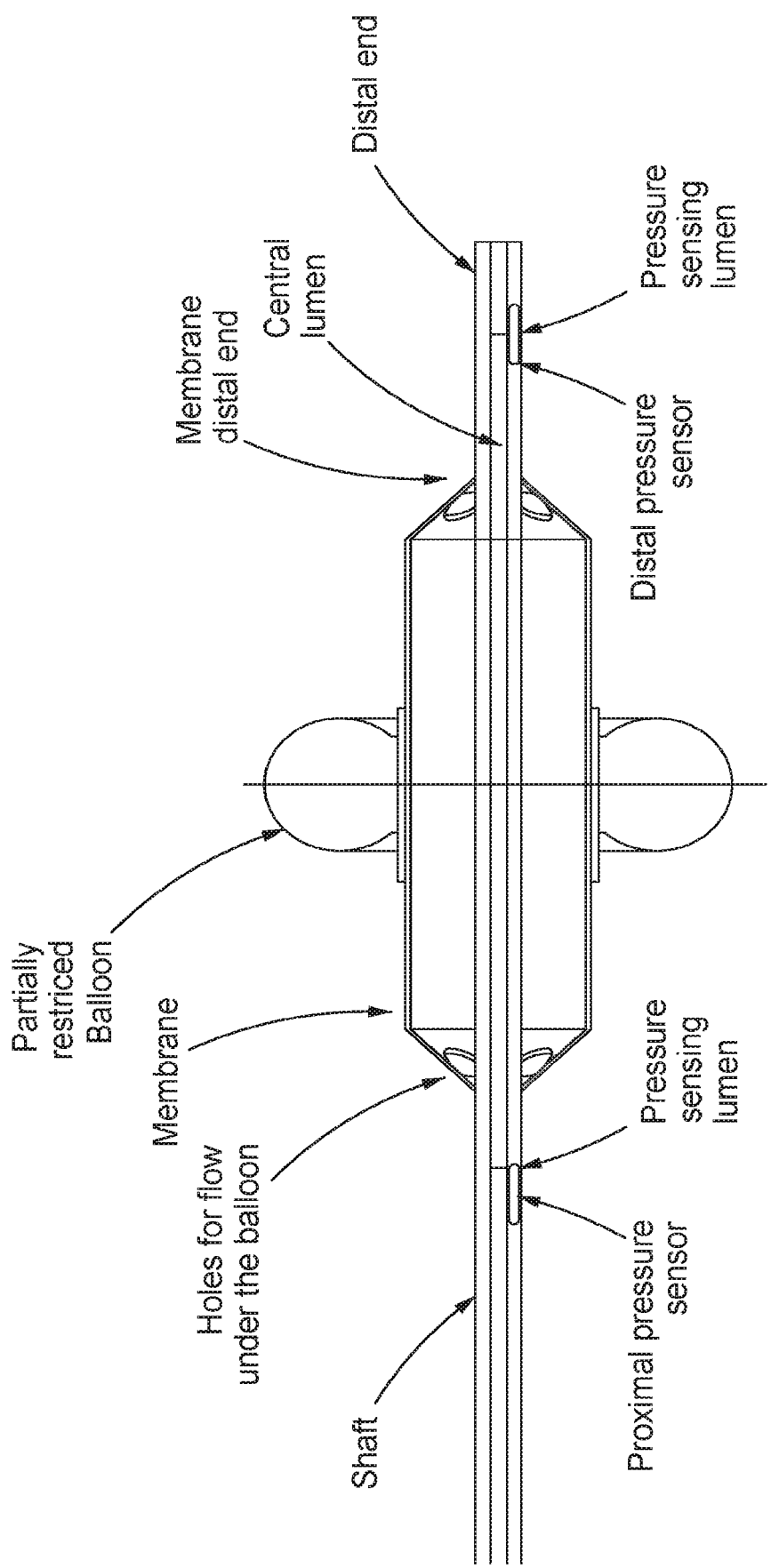
FIG. 51 is a schematic view of one embodiment of a catheter having a single restriction member.

The catheter can have any suitable configuration. In some embodiments, as shown in an embodiment of FIG. 51, a catheter includes a single selectively deployable restriction member or restrictor, a shaft, and a flexible membrane that is generally tubular in this illustrated embodiment. The shaft can have one or more lumens extending therethrough. For example, as shown in FIG. 51, it can have a central lumen and at least one pressure sensing lumen that can have proximal and distal pressure sensors. Also, in some embodiments, one or more pressure sensors can be associated with the central lumen.

The restrictor is attached to the membrane and surrounds the membrane and the shaft. In the example in FIG. 51, the single selectively deployable restriction member is formed over a portion of the flexible membrane at substantially a midpoint between a proximal end of the flexible membrane and a distal end of the flexible membrane. The flexible membrane can be assembled to the catheter (e.g., coupled to the shaft) in any of a number of ways to enable the flexible membrane to form an ovoid, kidney, or another shape upon expansion of the flexible membrane (as a result of activating the restrictors) so that blood can be transported from a position within the vein proximal to the restrictor to a point distal to the restrictor. The membrane can be attached, e.g., bonded or welded, around a partial portion (such as a non-zero portion that is less than 360° of the catheter shaft's circumference) or full portion (360° around the catheter shaft's circumference) of the circumference of the catheter's shaft, such as in a range of about 10° to 360° of the shaft's circumference.

In FIG. 51, the flexible membrane is attached to a portion of the catheter shaft circumference. The restrictor can be bonded or welded to an outer surface of the flexible membrane so that the restrictor surrounds the outer circumference of the catheter and the flexible membrane. As discussed above, the restrictor can have features that facilitate its attachment to the membrane.

The membrane can have many various configurations, including any of the membrane configurations described herein. As also shown in FIG. 51, the membrane can have holes or openings that allow fluid to flow under the restrictor. It should be appreciated that the openings are shown in the proximal and distal ends of the membrane by way of example only, as a suitable number of openings can be formed at any suitable locations in the membrane. The membrane can have any suitable size. For example, as shown in FIG. 51, the membrane can have a diameter in a range of from about 4 mm to about 10 mm.

The restrictor can also have various configurations. In the example illustrated, as shown in FIG. 51 through FIG. 32, the restrictor includes an inflatable balloon. The restrictor and the balloon can be configured similar to any of the restrictors and balloons described herein, though the described configurations can be modified. The balloon is configured to be inflated such that in a relaxed configuration the balloon is not inflated and in the activated configuration the balloon is inflated. The balloon can be inflated similar to the manner described above (e.g., using an inflation lumen, etc.), or in any other manner. For example, the catheter can include at least one inflation lumen through which an inflation fluid (e.g., air, liquid, etc.) can be introduced to inflate/deflate the balloon.

The diameter of the balloon can be from about 8 mm to about 20 mm. As indicated in FIG. 51, the balloon is shown in an activated or inflated configuration in which it partially restricts the blood flow through the membrane. As shown, in this example, the balloon is configured such that its portions surrounding the membrane have omega-like shapes, though the balloon can have other shapes that deviate from a circle. For example, in at least some embodiments, the balloon can be configured similar to restriction member 502 in FIG. 17. The balloon may not be mounted on the membrane as a full circle such that, when the balloon is inflated, some of its portions are irregularly shaped—e.g., it can at least partially bulge inwardly, towards the membrane, thus causing a diameter of the flexible membrane to reversibly decrease. The balloon can be configured to be able to bulge inwardly in many different ways. The inflation of the balloon can be controlled using one or more suitable sensors (e.g., pressure sensors) monitoring pressure upstream and downstream of the balloon. Because the amount of the blood flow allowed through the catheter (which affects the increase in the diastolic suction forces of the heart), depends on the degree of the inflation of the balloon, the degree of the inflation is controlled based on the blood pressure being monitored.

Figure 52:
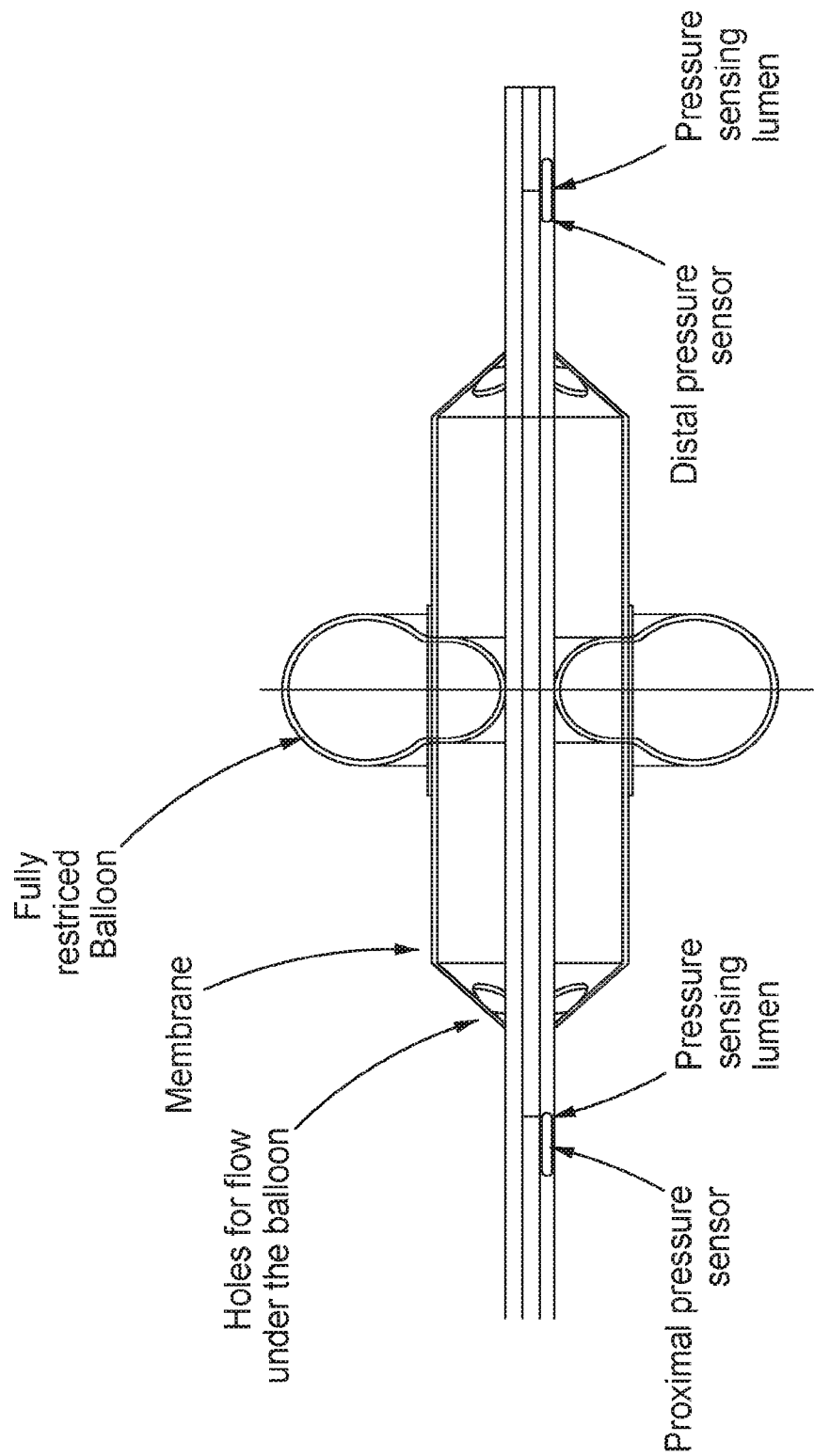
FIG. 52 is a schematic, partially transparent view of the catheter of FIG. 51.
Figure 53:
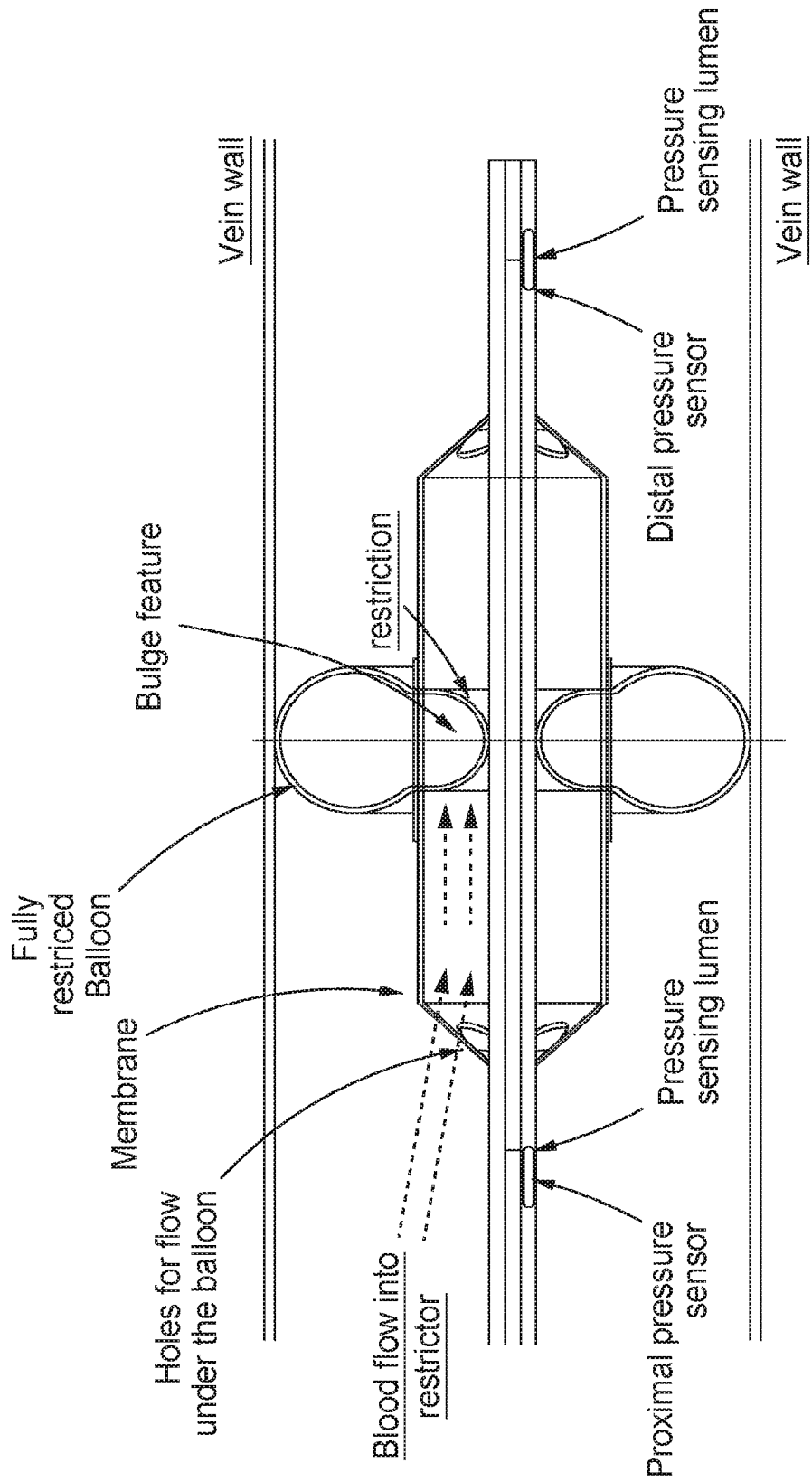
FIG. 53 is another schematic view of the catheter of FIG. 51, illustrating a blood flow into the single restriction member and a vein wall.

FIG. 52 and FIG. 31B illustrate the balloon when it fully restricts the membrane. In use, the balloon can be in any configuration that can be between the configuration in FIG. 51 in which the balloon partially restricts the membrane and the configuration in FIG. 52 and FIG. 31B in which the balloon fully restricts the membrane. The balloon can be controlled to be selectively expanded so as to at least partially constrict the membrane to form a tunnel therethrough that causes the heart to pump blood in harder. As a result, pressure in the area distal to the balloon is reduced.

FIG. 54 through FIG. 56 illustrate schematically a process of activation of a balloon and a flexible membrane coupled thereto which forms a lumen for blood flow. As discussed before, the balloon at least partially encompasses the flexible membrane coupled to a catheter shaft. The shaft with the membrane and the balloon is shown to be disposed within a vein. FIG. 54 illustrates the shaft, membrane, and balloon prior to activation or inflation of the balloon. In FIG. 55, the balloon is inflated to some degree such that it contacts the vein wall, and the membrane coupled to and at least partially surrounded by the balloon forms a blood flow lumen. As shown, the balloon can be inflated such that one or more bulges or other features are formed about an outer wall of the membrane. FIG. 56 shows that the balloon is inflated further so as to constrict the membrane further and to thus decrease a diameter of a blood flow lumen in the membrane. The balloon is inflated further so as to form at least one bulging feature compressing the membrane, as shown schematically in FIG. 56. Thus, the blood flow lumen in FIG. 56 is smaller than the blood flow lumen in FIG. 55. In some embodiments, a diameter of the blood flow lumen as shown in FIG. 56 (which can be an average diameter, since the lumen may not be uniformly shaped throughout its circumference) can be in a range of from about 1 mm to about 4 mm.

A distal portion of the catheter system, e.g., a distal end of the shaft (FIG. 51), which can have an atraumatic tip, in the initial configuration can be inserted into the jugular vein of the patient, which is the left internal jugular vein in this embodiment of FIG. 51. After positioning the catheter within the patient, the restrictor can be expanded, e.g., moved from its relaxed configuration to its activated configuration. The expansion of the restrictor also expands the flexible membrane, e.g., moves the flexible membrane from a relaxed configuration to an activated configuration. Moreover, because of the configuration of the restrictor (e.g., it has one or more bulging or other features), the expanded membrane is constricted so as to form a lumen or tunnel therethrough of a certain size. The size of the tunnel can be controlled by adjusting a degree of the inflation of the balloon, which can be done using a suitable controller. Pressure can be monitored using suitable sensors (e.g., blood pressure sensors), which can be associated with pressure sensor lumens, to determine when a desired decrease between the pressure proximal to the catheter and the pressure distal to the catheter is achieved. Pressure upstream and downstream of the restrictor can be monitored.

With reference to FIG. 51, blood now flows from the jugular vein into the flexible membrane and flows therethrough to the innominate vein. The expansion of the restrictor occludes a portion of the vein in which the catheter is deployed, and, thus, an area proximate to the catheter becomes a low pressure zone. No suction pump or a similar device may be required because the patient's heart itself functions as a pump during its normal operation. In particular, as mentioned above, the heart during the diastolic filling phase acts as a suction pump. The venous system acts as a filling reservoir for the right heart to pump blood in. Because part of the venous system is constricted by the catheter, the heart needs to pump in harder, which results in reduction of the pressure in the venous system, as shown by way of example in FIG. 49.

Figure 57:
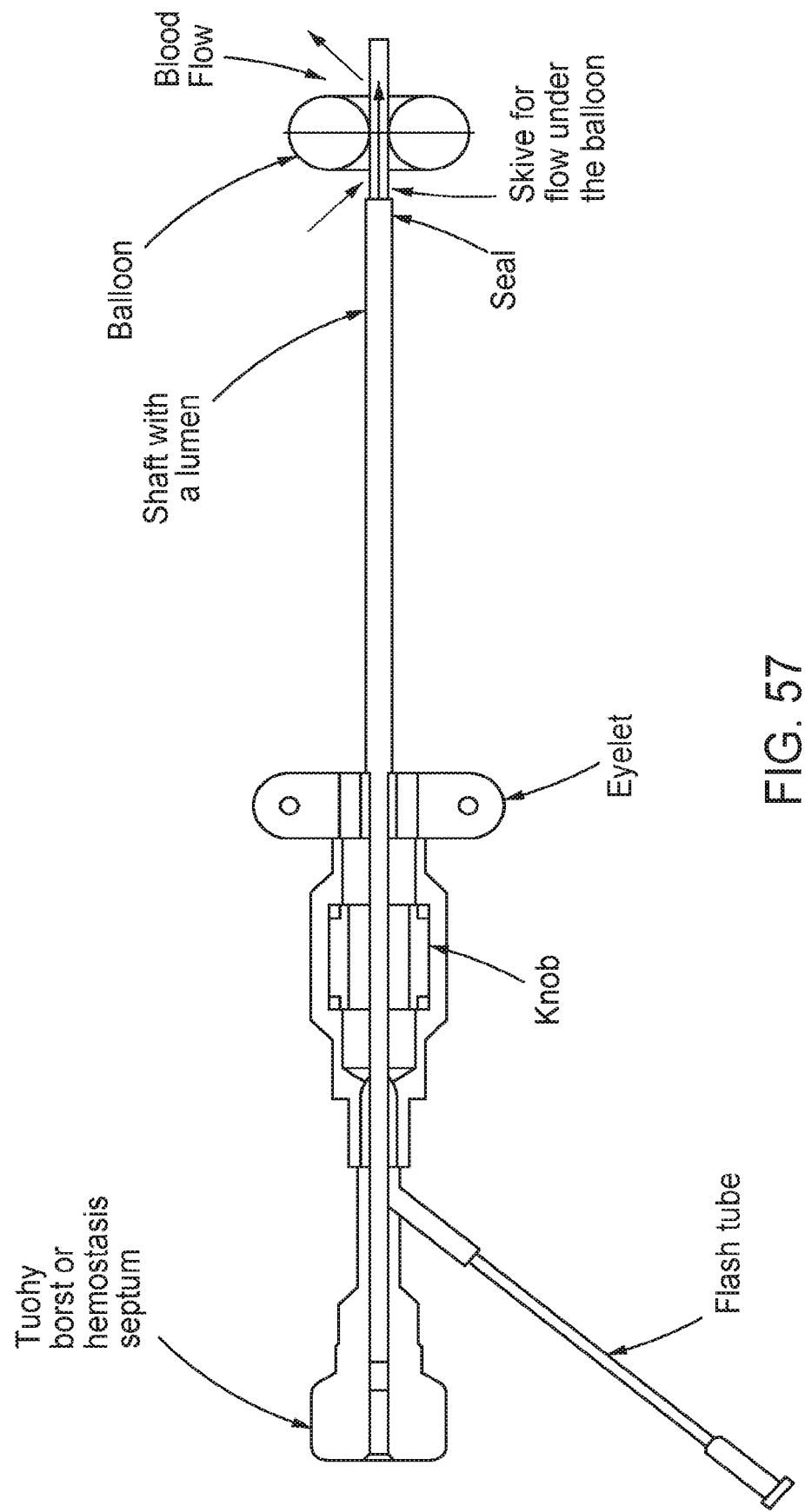
FIG. 57 is a cross-section view through a catheter system with a single restrictor, or balloon.

FIG. 57 illustrates another embodiment of a catheter system having a proximal restriction member or restrictor including an expandable balloon. The catheter system can be configured similarly to a portion of the catheter system with a proximal balloon shown in FIG. 33. In this example, blood can flow through a lumen formed in a catheter's shaft. Blood can flow through the balloon as shown schematically in FIG. 57. The balloon is configured to be activated to become expanded, and in an expanded configuration it at least partially occludes a vein in which the catheter system is placed. A shaft of the catheter system has a lumen extending therethrough and communicating with a lumen extending through the balloon. Fluid flow through the lumen of the catheter system of FIG. 57 can be regulated using a flow regulator component similar to that shown in FIG. 24, and/or other flow regulator component(s) (e.g., a plunger). Thus, the lumen can be controlled to thus control reduction in blood pressure that can be achieved by causing the heart to pump in blood harder during diastole.

In FIG. 57, a knob can be configured to be operated to move a plunger or other component configured to close and open the lumen extending through the balloon to regulate blood flow. An eyelet is configured to facilitate securement of the catheter system to a patient during use. The catheter shaft can be locked in position using, for example, a Tuohy Borst valve. The Tuohy Borst valve or hemostasis septum can be used to prevent blood from coming in the opposite direction. The catheter can have any other suitable components.

In use, the catheter is introduced into the vein (as shown, e.g., in FIG. 49), e.g., using a guidewire extending through the central lumen. In an initial configuration, the catheter's restrictor has the balloon is in a non-inflated configuration. The catheter can be delivered to the insertion site in a compressed configuration. For example, it can be releasably disposed within a sheath. Thus, the shaft of the catheter encircled by a compressed flexible membrane that is in turn surrounded by the compressed restriction member can be delivered to a desired location in a vein in a patient's body. The catheter can be advanced out of the sheath to position the catheter as shown in FIG. 49.

Figure 58:
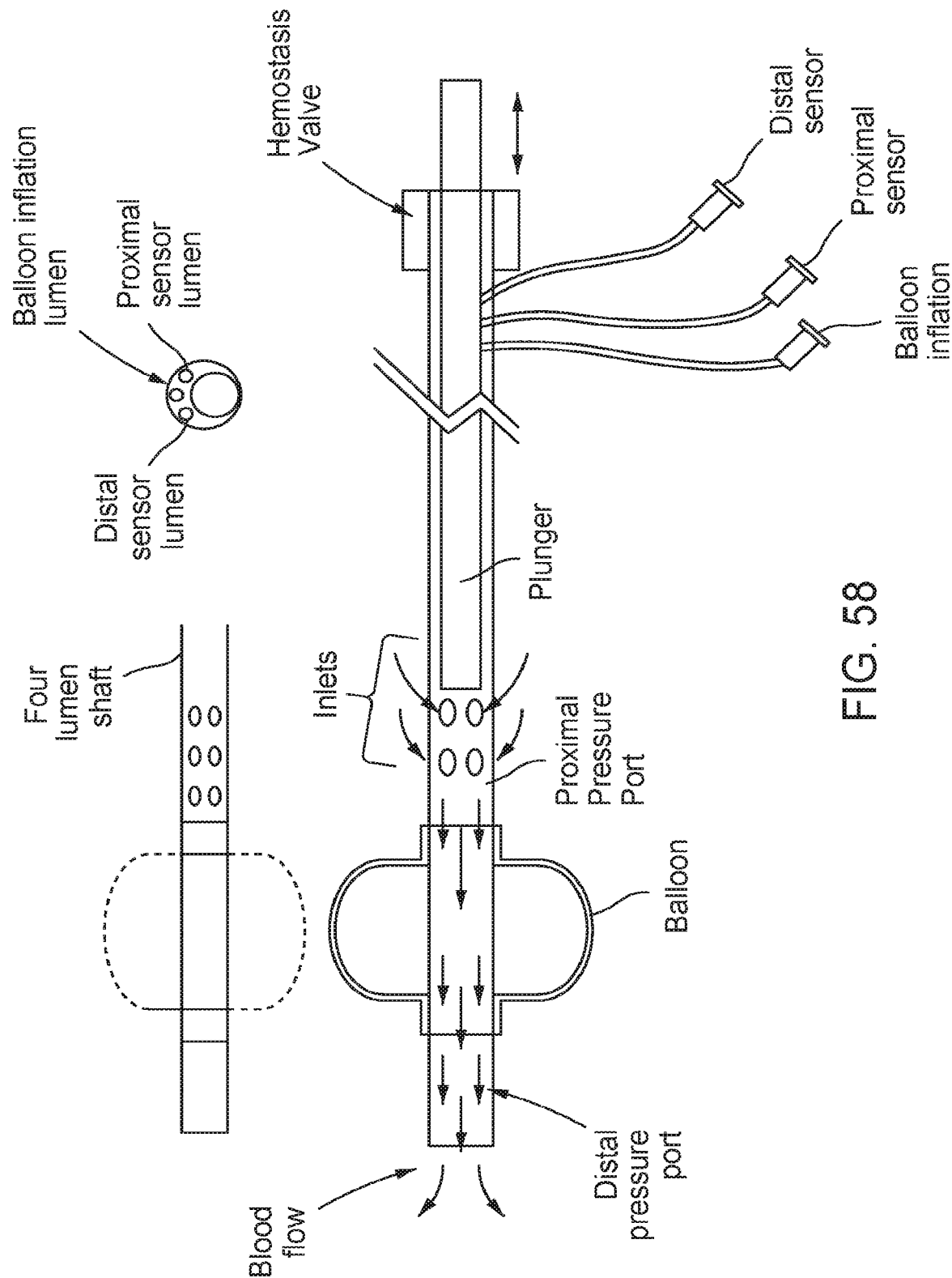
FIG. 58 is a schematic view of another embodiment of a catheter having a single restriction member.

FIG. 58 through FIG. 61 illustrate additional examples of a catheter having a single restriction member. In particular, FIG. 58 shows a catheter having a catheter shaft and an expandable balloon disposed at a distal end of the catheter. The catheter shaft can have four lumens, such as a central lumen for fluid flow, a distal sensor lumen, a balloon inflation lumen, and a proximal sensor lumen. The catheter shown in FIG. 58 has a plunger or other similar component configured to control an amount of fluid allowed to be transmitted through the central lumen, by reversibly occluding proximal (suction) inlets formed through the shaft's sidewall proximally to the balloon. The inlets are in communication with the lumen so as to allow fluid to enter the catheter's lumen therethrough, as shown in FIG. 58 by four arrows at the proximal suction inlet pointing inward toward the lumen catheter. The proximal inlets can include any number of openings formed through the shaft's sidewall. The openings can have any of a variety of configurations, e.g., slits, circular holes, ovular holes, rectangular slots, etc. The number, position, and configuration of the inlets and the configuration of the adjustable plunger enable the regulation of the flow which is directed into the catheter. As shown in FIG. 58, the fluid flow is directed into and through the catheter shaft and it leaves the catheter from a tip or one or more openings distal to the balloon.

Figure 59:
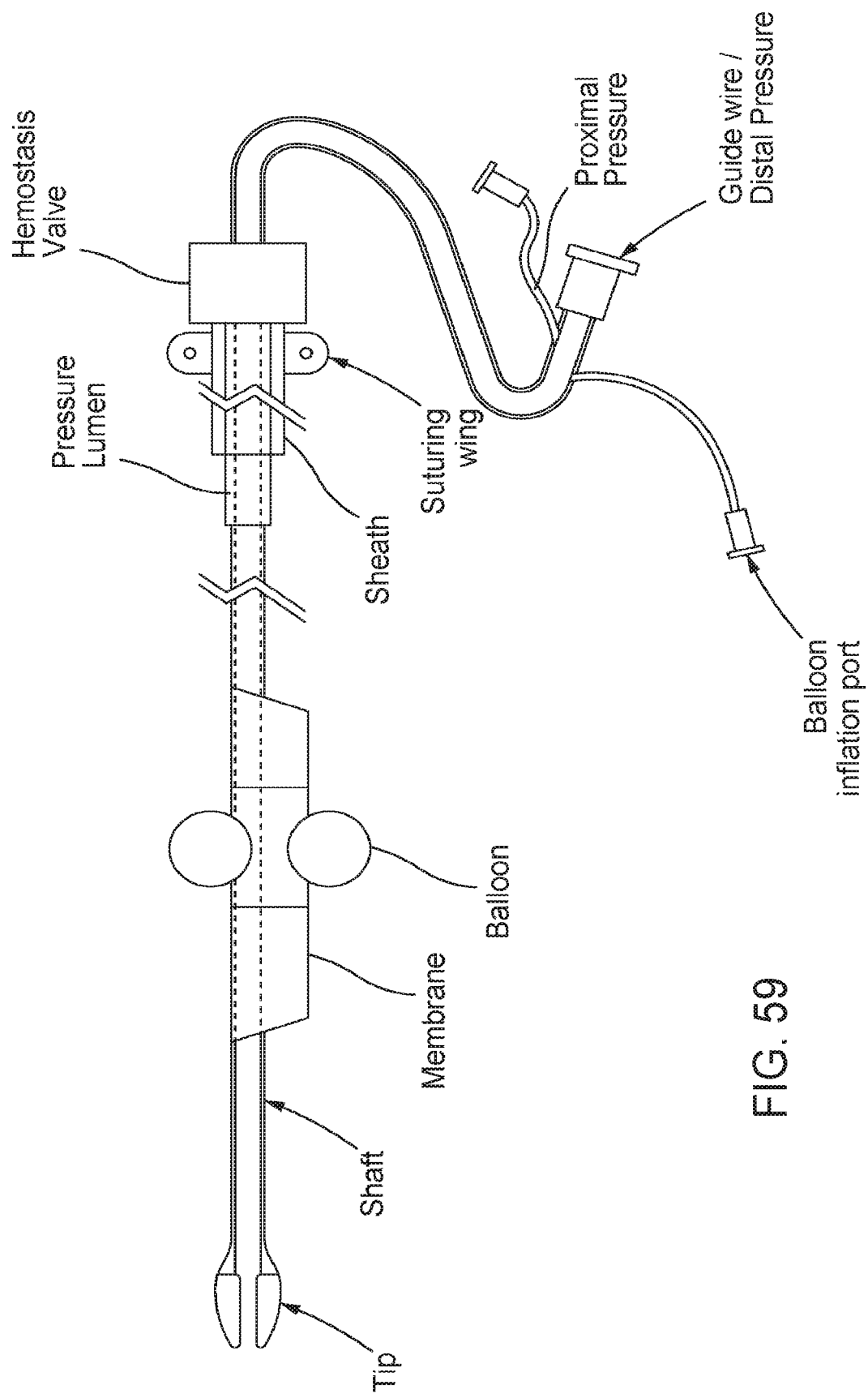
FIG. 59 is a schematic, partially transparent view of an embodiment of a catheter having a single restriction member.
Figure 60:
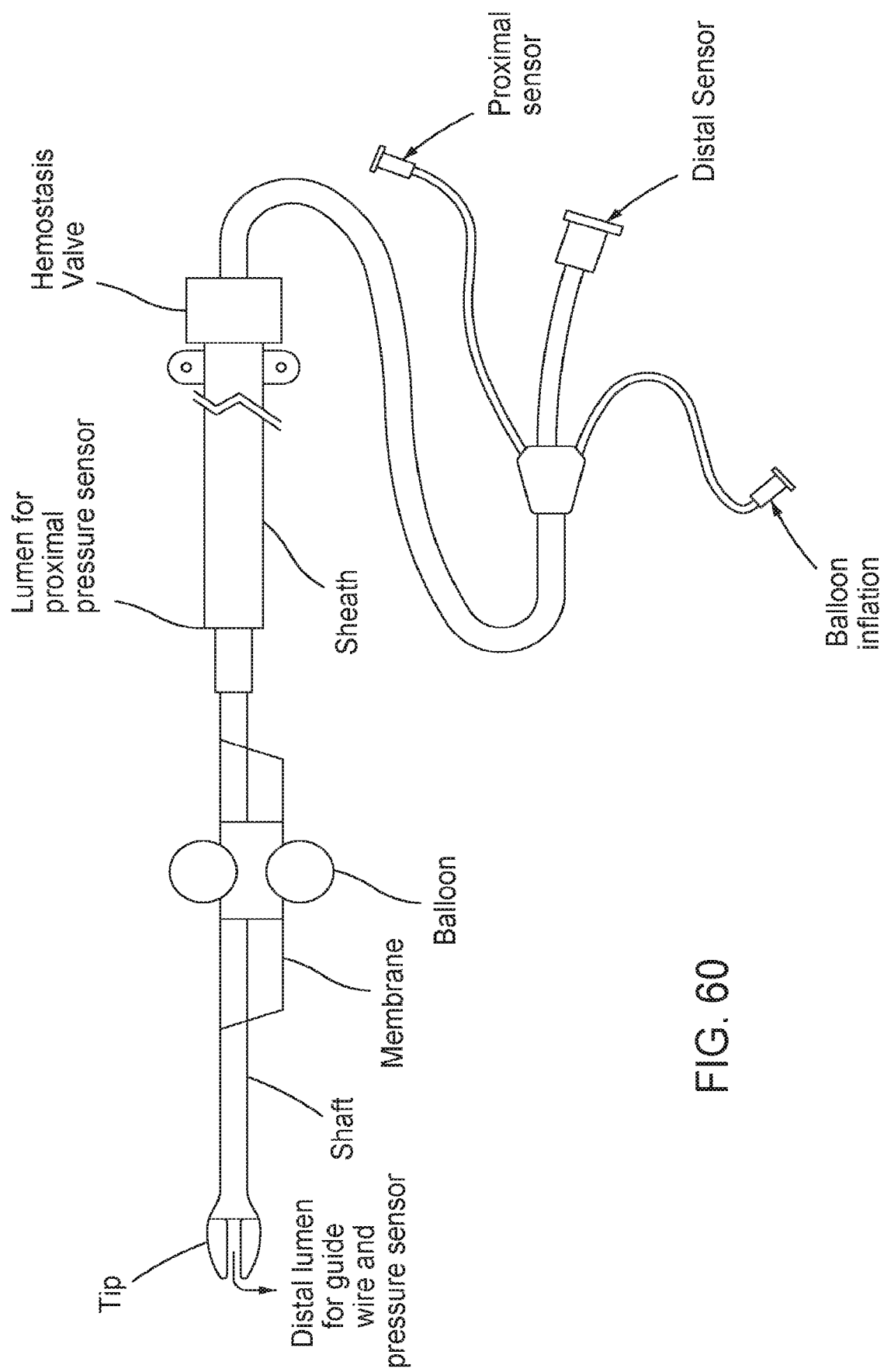
FIG. 60 is a schematic, partially transparent view of an embodiment of a catheter having a single restriction member and a flexible membrane.

FIG. 59 shows an embodiment of a catheter having a single selectively deployable restriction member and a flexible membrane. FIG. 60 illustrates another embodiment of a catheter having a single selectively deployable restriction member and a flexible membrane. The catheters in FIG. 59 and FIG. 60 can be similar to the catheters described above, for example, those shown in FIG. 51, FIG. 52, and FIG. 31B, though different components can be used additionally or alternatively. In the catheters shown in FIG. 59 and FIG. 60, the restriction member has an expandable balloon mounted over a collapsible membrane and a shaft. Once the catheter is positioned in a vein, the balloon is activated to be expanded. In the expanded or inflated configuration, the balloon can be pressed against the wall of the vein. The flexible membrane is also activated and defines a lumen for passage of blood therethrough. Further inflation of the balloon causes the balloon to be further constricted by the vein wall, which causes the lumen in the membrane to be decreased. A size of the lumen can be adjusted to cause the diastolic suction forces of the heart to be increased so as to create a low pressure zone in a downstream side of the restriction member.

Figure 61:
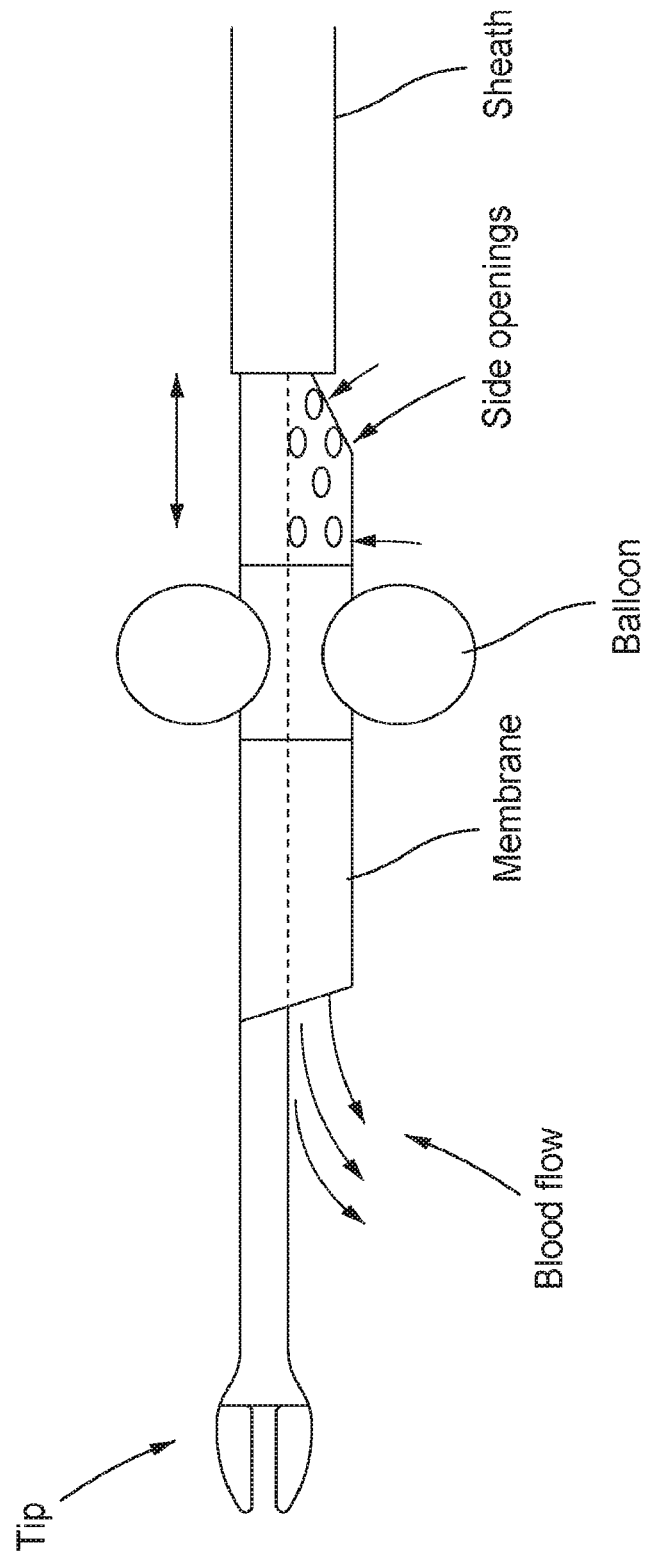
FIG. 61 is a schematic, partially transparent view of another embodiment of a catheter having a single restriction member and a flexible membrane.

FIG. 61 illustrates another embodiment of a catheter having a single selectively deployable restriction member and a flexible membrane. In this embodiment, the flexible membrane is coupled to a sheath such that the membrane remains coupled to the sheath when the catheter is positioned in a vein. The flexible membrane has inlet opening formed through a side wall thereof. The catheter is configured such that a blood flow through a lumen formed in the membrane is controlled by adjusting a number of the inlet openings that are open and closed.

This is done by advancing and retracting the catheter relative to the sheath, to vary a number of the inlet openings that are open and closed.

It should be appreciated that the catheters shown in FIG. 58 through FIG. 61 can include other suitable components not shown for the sake of simplicity. For example, the catheters can have components configured to measure pressure upstream and downstream of the balloon.

The catheter systems described in connection with FIG. 48 through FIG. 61 provide various advantages over existing systems. For example, the systems include a reduced number of components—a single selectively deployable restrictor is used, and the use of many components (e.g., suction pumps) included a two-restrictor catheter system can be avoided. This simplifies the catheter system, its operation, use, and maintenance. Also, a lumen having blood flowing therethrough is formed in a controlled manner, with the size of the lumen determining at least in part a magnitude of the pressure reduction in the venous system. The pressure reduction can be achieved not only downstream of the restrictor, but in other parts throughout the venous system by placing the catheter in a vein.

The catheter system with a single restriction member can be placed in a patient's body for a relatively short amount of time, e.g., several hours. Also, the catheter system can be configured to be implanted in a patient's body for a longer duration of time (e.g., several days) and the catheter can be controlled to be selectively activated and deactivated.

A person skilled in the art will appreciate that the systems and methods disclosed herein can be used with a variety of surgical devices, including measuring devices, sensing devices, locator devices, insertion devices, etc.

One skilled in the art will appreciate further features and advantages of the described subject matter based on the above-described embodiments. Accordingly, the present disclosure is not to be limited by what has been particularly shown and described, except as indicated by the appended claims. All publications and references cited herein are expressly incorporated herein by reference in their entirety.

What is claimed is:

1. A method of reducing pressure at an outflow of a duct, the method comprising:
   positioning a device comprising a catheter in a blood vessel near an output of a duct, the catheter comprising a distal portion having an inlet and an outlet, the device comprising a selectively deployable restrictor a portion of which defines a tapered lumen;
   deploying the restrictor; and
   pumping blood through the tapered lumen into an impeller assembly of the device to thereby lower pressure near the output of the duct;
   wherein the restrictor is mounted around the impeller assembly.

2. The method of claim 1, wherein the restrictor occludes the blood vessel but for the lumen therethrough.

3. The method of claim 1, wherein the vessel is an internal jugular vein, a subclavian vein, or an innominate vein.

4. The method of claim 1, wherein the device comprises a second restrictor attached to a distal end of said device and the method further comprises positioning the second restrictor inside the blood vessel.

5. The method of claim 4, wherein the restrictor and the second restrictor are positioned separately inside the blood vessel.

6. The method of claim 5, wherein the method further comprises deploying the second restrictor.

7. The method of claim 6, wherein the method comprises deploying the restrictor and second restrictor simultaneously.

8. The method of claim 6, wherein the method comprises deploying the restrictor and second restrictor separately.

9. The method of claim 6, wherein deploying the restrictor and second restrictor produces two occlusions within blood vessel.

10. The method of claim 9, wherein the two occlusions define a low pressure zone between the first and second restrictors within a portion of the blood vessel.

11. The method of claim 1, wherein the distal portion of the catheter comprises the impeller assembly with an impeller disposed therein.

12. The method of claim 11, wherein the impeller assembly comprises the inlet and the outlet.

13. The method of claim 12, wherein the device further comprises an elongate driveshaft extending proximally from the impeller, and wherein blood flows out of the impeller assembly via the outlet along the side of the impeller assembly.

14. The method of claim 1, wherein at least a portion of the impeller is distal to the restrictor.

15. The method of claim 1, further comprising activating the impeller inside the blood vessel thereby directing fluid by the tapered surface of the restrictor into the inlet, through the assembly and out the outlet.

16. The method of claim 1, wherein the catheter comprises a diameter of between 9 and 15 Fr.

17. The method of claim 1, wherein the restrictor comprises an inflatable balloon and the method further comprises inflating the balloon when the device is positioned in the blood vessel.

18. The method of claim 1, wherein, when the restrictor is deployed, a second portion of the restrictor is not tapered.

* * * * *